United States Patent [19]

Takaya et al.

[11] Patent Number: 4,698,340
[45] Date of Patent: Oct. 6, 1987

[54] PYRIMIDINE DERIVATIVES, PROCESSES FOR PREPARATION THEREOF AND COMPOSITION CONTAINING THE SAME

[75] Inventors: Takao Takaya, Kawanishi; Hisashi Takasugi, Osaka; Atsushi Kuno, Mino; Yoshie Sugiyama, Takarazuka, all of Japan

[73] Assignee: Fujisawa Pharmaceutical Co., Ltd., Osaka, Japan

[21] Appl. No.: 753,912

[22] Filed: Jul. 11, 1985

[30] Foreign Application Priority Data

Jul. 19, 1984 [GB] United Kingdom ............... 8418380
Oct. 1, 1984 [GB] United Kingdom ............... 8424711
Apr. 15, 1985 [GB] United Kingdom ............... 8509623

[51] Int. Cl.$^4$ .................. A61K 31/505; C07D 239/26
[52] U.S. Cl. .................. 514/222; 514/235; 514/256; 544/60; 544/122; 544/242; 544/295; 544/333; 544/335; 544/58.4
[58] Field of Search ............ 544/58.4, 60, 122, 242, 544/295, 333, 335; 514/222, 235, 256

[56] References Cited

U.S. PATENT DOCUMENTS 3,969,355  7/1976  Schwan .............................. 544/242
4,382,140  5/1983  Schwan .............................. 544/247

FOREIGN PATENT DOCUMENTS 0103796  3/1984  European Pat. Off. .

OTHER PUBLICATIONS

Menichi et al, Chemical Abstracts, vol. 74, (1971), 125626t.
J. Heterocyclic Chem., 18, 183 (1981); E. J. Breaux et al, An Improved General Synthesis of 4-Aryl-5-Pyrimidinecarboxylates, Jan. 1981.
Arch. Pharm. (Weinheim) 314, 938-949 (1981); Klaus Görlitzer et al, 2,4-Diaryl-6-Methyl-1,2,3,4-Tetrahydropyrimidine-5-Carbonsäureester.
Arch. Pharm. (Weinheim)312, 591-597(1979); Fritz Eiden et al, Über die Reaktion von 2,6-Dimethyl-4-Pyron-3,5-Dicarbonsäureethylester Mit Aminen.

Primary Examiner—Richard L. Raymond
Attorney, Agent, or Firm—Oblon, Fisher, Spivak, McClelland, & Maier

[57] ABSTRACT

The invention relates to pyrimidine derivatives and their pharmaceutically acceptable salts which are useful in the treatment of cerebrovascular diseases, to processes for preparation thereof and to the composition containing the same, said pyrimidine derivatives being represented by the following formula:

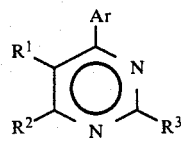

wherein Ar, $R^1$, $R^2$ and $R^3$ are as defined in the disclosure.

15 Claims, No Drawings

PYRIMIDINE DERIVATIVES, PROCESSES FOR PREPARATION THEREOF AND COMPOSITION CONTAINING THE SAME

This invention relates to new pyrimidine derivatives. More particularly, this invention relates to the pyrimidine derivatives and their pharmaceutically acceptable salts which are useful in the treatment of cerebrovascular diseases, to processes for preparation thereof and to the composition containing the same.

The pyrimidine derivatives of this invention are represented by the following general formula (I):

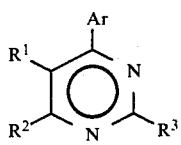
(I)

wherein
Ar is aryl substituted with 1 to 3 substituent(s) selected from the group consisting of nitro, amino, halogen, cyano, hydroxy, carbamoyl, halo(lower)alkyl, lower alkoxy, halo(lower)alkoxy, lower alkanoyloxy, lower alkylthio, lower alkanesulfinyl, lower alkanesulfonyl, esterified carboxy, optionally substituted N-containing heterocyclic group and a group of the formula:

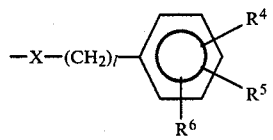

(in which X, l, $R^4$, $R^5$ and $R^6$ are each as defined in the below) or heterocyclic group containing one nitrogen and/or sulfur atom(s) and optionally substituted with nitro or halogen substituent(s);
$R^1$ is carboxy, esterified carboxy, lower alkanoyl, cyano, amino, carboxyamino, esterified carboxyamino, a group of the formula:

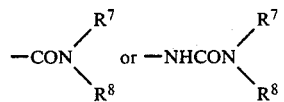

(in which $R^7$ and $R^8$ are each as defined in the below) or lower alkyl optionally substituted with 1 to 3 substituent(s) selected from the groups consisting of hydroxy, halogen, cyano, carboxy, esterified carboxy and a group of the formula:

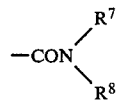

(in which $R^7$ and $R^8$ are each as defined in the below)
$R^2$ is hydrogen, aryl or lower alkyl optionally substituted with halogen, lower alkanoyloxy or lower alkoxy substituent(s); or
$R^1$ and $R^2$ are taken together to form a lactone ring with the adjacent carbon atoms;

$R^3$ is lower alkyl, aryl optionally substituted with halogen or optionally substituted N-containing heterocyclic group;
X is O or S;
l is an integer of 0, 1 to 6;
$R^4$, $R^5$ and $R^6$ are each hydrogen, nitro, lower alkyl, halogen or lower alkoxy;
$R^7$ and $R^8$ are each hydrogen, optionally substituted N-containing heterocyclic group or lower alkyl optionally substituted with 1 to 3 substituent(s) selected from the group consisting of hydroxy, halogen, amino, lower alkanoylamino, mono- or di(lower)alkylamino, tri(lower)alkylammonio and optionally substituted N-containing heterocyclic group; or
$R^7$ and $R^8$ are taken together to form optionally substituted N-containing heterocyclic group with the adjacent nitrogen atom;
provided that the substituent(s) on the aryl group for Ar is not halogen when $R^2$ is hydrogen.

Particulars of the various definitions mentioned in this specification and preferred examples thereof are explained in the following.

The term "lower" used in this specification is intended to mean a group having 1 to 6 carbon atoms, unless otherwise provided.

Suitable "aryl" may include phenyl, naphthyl and the like.

Suitable "halogen" may include bromo, fluoro, chloro and iodo.

Suitable "lower alkyl" may include straight or branched one such as methyl, ethyl, propyl, isopropyl, butyl, t-butyl, pentyl, hexyl and the like.

Suitable "halo(lower)alkyl" may include chloromethyl, trifluoromethyl, bromoethyl, dichloroethyl, iodopropyl, trichloro-t-butyl, fluoropentyl, chlorohexyl and the like.

Suitable "lower alkoxy" may include straight or branched one such as methoxy, ethoxy, propoxy, isopropoxy, butoxy, t-butoxy, pentyloxy, hexyloxy and the like.

Suitable "lower alkanoyloxy" may include straight or branched one such as formyloxy, acetyloxy, propionyloxy, isobutyryloxy, valeryloxy, pivaloyloxy and the like.

Suitable "lower alkylthio" may include methylthio, ethylthio, propylthio, t-butylthio, hexylthio and the like.

Suitable "lower alkanesulfinyl" may include methanesulfinyl, ethanesulfinyl, propane-2-sulfinyl, 2-methylpropane-2-sulfinyl, hexanesulfinyl and the like.

Suitable "lower alkanesulfonyl" may include methanesulfonyl, ethanesulfonyl, propane-2-sulfonyl, 2-methylpropane-2-sulfonyl, hexanesulfonyl and the like.

Suitable ester moiety in the "esterified carboxy", "esterified carboxy(lower)alkyl" and "esterified carboxyamino" may include lower alkyl ester (e.g. methyl ester, ethyl ester, propyl ester, isopropyl ester, butyl ester, t-butyl ester, pentyl ester, hexyl ester, etc.), mono(di or tri)halo(lower)alkyl ester (e.g. iodoethyl ester, dichloroethyl ester, trichloroethyl ester, trifluoromethyl ester, etc.), hydroxy(lower)alkyl ester (e.g. hydroxymethyl ester, hydroxyethyl ester, hydroxypropyl ester, hydroxybutyl ester, etc.) ar(lower)alkyl ester (e.g. benzyl ester, 4-nitrobenzyl ester, trityl ester, etc.), alkenyl ester (e.g. vinyl ester, allyl ester, etc.) and the like.
Suitable "halo(lower)alkoxy" may include chloromethoxy, difluoromethoxy, 2-fluoropropyloxy and the like.

Suitable "N-containing heterocyclic group" may include unsaturated 5- or 6-membered heteromonocyclic group containing 1 or 2 nitrogen atom(s), for example, pyrrolyl, imidazolyl, pyrazolyl, pyridyl, pyrimidinyl, 1,2,3,6-tetrahydropyridyl, etc.;

saturated 5- or 6-membered heteromonocyclic group containing 1 or 2 nitrogen atom(s) and/or 1 or 2 oxygen atom(s), for example, pyrrolidinyl, imidazolidinyl, piperidyl, piperazinyl, morpholinyl, etc.;

saturated 5- or 6-membered heteromonocyclic group containing 1 or 2 nitrogen atom(s) and 1 or 2 sulfur atom(s), for example, thiazolidinyl, thiomorpholinyl, etc., and the like. Said "N-containing heterocyclic group" may have 1 to 3 substituents such as lower alkyl as exemplified above, hydroxy(lower)alkyl (e.g., hydroxymethyl, hydroxyethyl, hydroxypropyl, hydroxyhexyl, etc.), lower alkoxy as exemplified above, and the like.

Preferable example of "substituted N-containing heterocyclic group" may include lower alkylpyrrolidinyl (e.g., 1-methylpyrrolidinyl, 2-ethylpyrrolidinyl, 3-isopropylpyrrolidinyl, 1-t-butylpyrrolidinyl, 1-hexylpyrrolidinyl, etc.), lower alkylimidazolidinyl (e.g., 3-methylimidazolidinyl etc.), lower alkylpiperidyl (e.g., 1-methylpiperidyl, 1-ethylpiperidyl, 2-t-butylpiperidyl, 3-hexylpiperidyl, etc.), lower alkylpiperazinyl (e.g., 1-methylpiperazinyl, 2-ethylpiperazinyl, 3-isopropylpiperazinyl, 1-hexylpiperazinyl, etc.), lower alkylpyridyl (e.g., 1-methylpyridyl, 2-ethylpyridyl, 3-t-butylpyridyl, 1-hexylpyridyl, etc.) and the like.

Preferable example of a group of the formula:

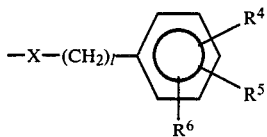

may include phenoxy, phenylthio, nitrophenoxy, phenyl(lower)alkoxy (e.g., benzyloxy, phenethyloxy, etc.), phenyl(lower)alkylthio (e.g., benzylthio, phenethylthio, etc.), halophenyl(lower)alkoxy (e.g., chlorobenzyloxy, dichlorophenethyloxy, fluorophenylbutoxy, bromophenylhexyloxy, etc.), halophenylthio (e.g., chlorophenylthio, fluorophenylthio, etc.), nitrophenyl(lower)alkoxy (e.g., nitrobenzyloxy, nitrophenethyloxy, nitrophenylbutoxy, etc.), lower alkylphenyl(lower)alkylthio (e.g., tolylmethylthio, xylylethylthio, etc.), lower alkoxyphenyl(lower)alkoxy (e.g., methoxyphenethyloxy, etc.) and the like.

Suitable "heterocyclic group containing one nitrogen and/or sulfur atom(s)" may include unsaturated 5- or 6-membered heteromonocyclic group containing one nitrogen and/or sulfur atoms, for example, pyrrolyl, pyridyl, thienyl, thiazolyl and the like.

Preferable example of "heterocyclic group containing one nitrogen and/or sulfur atom(s) substituted with nitro or halogen substituent(s)" may include nitropyridyl, halopyridyl (e.g. fluoropyridyl, chloropyridyl, bromopyridyl, etc.), nitrothienyl, halothienyl (e.g. fluorothienyl, chlorothienyl, bromothienyl, etc.), and the like.

Suitable "lower alkanoyl" and the "lower alkanoyl" moiety in the "lower alkanoylamino group" may include straight or branched one such as formyl, acetyl, propionyl, butyryl, valeryl, pivaloyl and the like.

Suitable "mono- or di-(lower)alkylamino" may include methylamino, ethylamino, isopropylamino, hexylamino, dimethylamino, diethylamino, dipropylamino, methylethylamino and the like.

Suitable "tri(lower)alkylammonio" may include trimethylammonio, triethylammonio, dimethylpropylammonio and the like.

Preferable example of the substituted lower alkyl group for $R^7$ and $R^8$ may include hydroxy(lower)alkyl (e.g., hydroxymethyl, hydroxyethyl, hydroxypropyl, hydroxyisopropyl, hydroxyhexyl, etc.), halo(lower)alkyl (e.g., chloromethyl, chloroethyl, fluoroethyl, bromoethyl, bromopropyl, chlorohexyl, etc.), amino(lower)alkyl (e.g., aminomethyl, aminoethyl, aminopropyl, etc.), lower alkanoylamino(lower)alkyl (e.g., acetylaminomethyl, acetylaminoethyl, acetylaminobutyl, isobutyrylaminoethyl, etc.), mono- or di(lower)alkylamino(lower)alkyl (e.g., methylaminomethyl, dimethylaminoethyl, diethylaminoethyl, dipropylaminoethyl, dimethylaminopropyl, diethylaminopropyl, dimethylaminobutyl, dimethylaminohexyl, etc.), tri(lower)alkylammonio(lower)alkyl (e.g., trimethylammoniomethyl, trimethylammonioethyl, triethylammonioethyl, dimethylethylammonioethyl, trimethylammoniopropyl, etc.), morpholinyl(lower)alkyl (e.g., morpholinylmethyl, morpholinylethyl, morpholinylpropyl, morpholinylbutyl, etc.), piperazinyl(lower)alkyl wherein piperazinyl is optionally substituted with lower alkyl (e.g., piperazinylmethyl, piperazinylethyl, piperazinylpropyl, methylpiperazinylethyl, ethylpiperazinylethyl, isopropylpiperazinylhexyl, etc.), piperidyl(lower)alkyl wherein piperidyl is optionally substituted with lower alkyl (e.g., piperidylmethyl, piperidylethyl, piperidylpropyl, ethylpiperidylethyl, ethylpiperidylhexyl, etc.), thiomorpholinyl(lower)alkyl (e.g, thiomorpholinylmethyl, thiomorpholinylethyl, thiomorpholinylpropyl, etc.), pyrrolidinyl(lower)alkyl wherein pyrrolidinyl is optionally substituted with lower alkyl (e.g., pyrrolidinylmethyl, pyrrolidinylethyl, ethylpyrrolidinylethyl, methylpyrrolidinylpropyl, isopropylpyrrolidinylhexyl, etc.), and the like.

Suitable "N-containing heterocyclic group which is formed by conjugation of $R^7$, $R^8$ and the adjacent nitrogen atom" may include 5- or 6-membered saturated or unsaturated N-containing heteromonocyclic group, for example, pyrrolidin-1-yl, imidazolidin-1-yl, piperidino, piperazin-1-yl, morpholino, thiomorpholin-4-yl, and the like. Said "N-containing heterocyclic group" may have 1 to 3 substituents such as lower alkyl as exemplified above, lower alkoxy as exemplified above, ar(lower)alkyl (e.g., benzyl, phenethyl, α-methylbenzyl, biphenylylmethyl, naphthylmethyl, etc.), lower alkoxy substituted ar(lower)alkyl (e.g., 4-methoxybenzyl, 3,4-dimethoxybenzyl, 3,4,5-trimethoxybenzyl, 4-isopropyloxybenzyl, etc.) or the like.

Preferable example of "optionally substituted N-containing heterocyclic group which is formed by conjugation of $R^7$, $R^8$ and the adjacent nitrogen atom" may include piperazin-1-yl, 4-methylpiperazin-1-yl, 4-benzylpiperazin-1-yl, 4-(3,4,5-trimethoxybenzyl)piperazin-1-yl, 3-methylpiperidino and the like.

Suitable "lactone ring" formed by $R^1$ and $R^2$ may include γ-lactone, δ-lactone and the like.

Suitable "lower alkylene" may include straight or branched one such as methylene, ethylene, trimethylene, pentamethylene, hexamethylene, ethylethylene, propylene and the like.

Suitable acid residue may include halogen as mentioned above, acyloxy (e.g., benzenesulfonyloxy, tosyloxy, etc.) and the like.

Suitable pharmaceutically acceptable salts of the object compound (I) are conventional non-toxic salts and may include a salt with an organic or inorganic acid such as maleic acid, fumaric acid, tartaric acid, citric acid, acetic acid, benzoic acid, hydrochloric acid, sulfuric acid, nitric acid, hydroiodic acid, phosphoric acid and the like.

The pyrimidine derivatives (I) can be prepared by various processes as illustrated in the following.

Process 1:

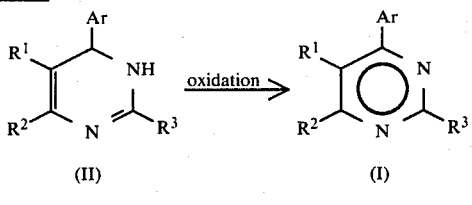

(II)       (I)

or a salt thereof    or a salt thereof

Process 2:

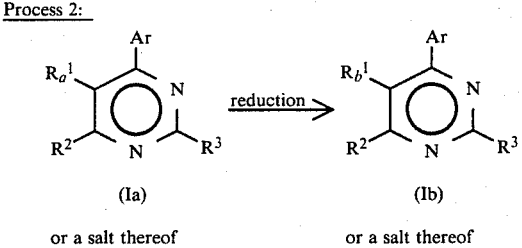

(Ia)       (Ib)

or a salt thereof    or a salt thereof

Process 3:

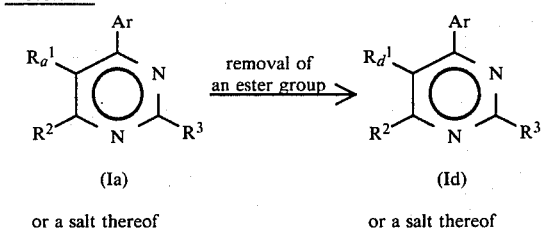

(Ia)       (Id)

or a salt thereof    or a salt thereof

Process 4:

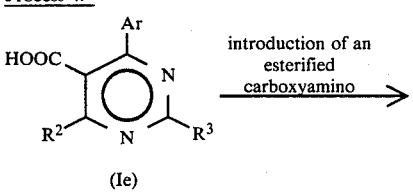

(Ie)

or its reactive derivative at the carboxy group or a salt thereof

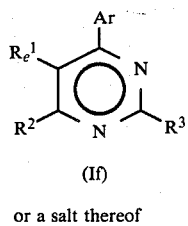

(If)

or a salt thereof

Process 5:

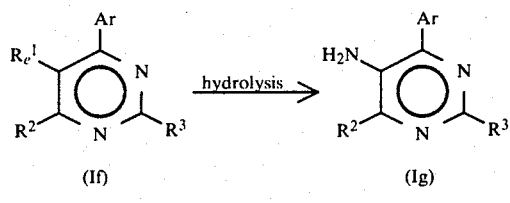

(If)       (Ig)

or a salt thereof    or a salt thereof

Process 6:

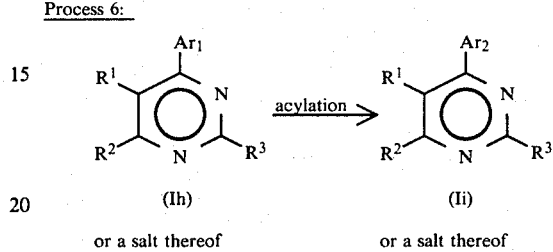

(Ih)       (Ii)

or a salt thereof    or a salt thereof

Process 7:

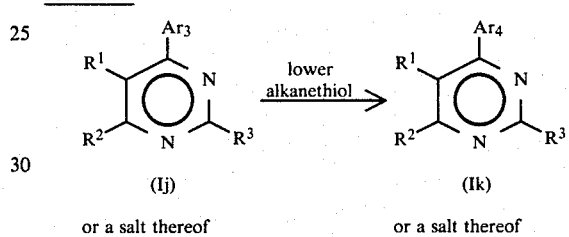

(Ij)       (Ik)

or a salt thereof    or a salt thereof

Process 8:

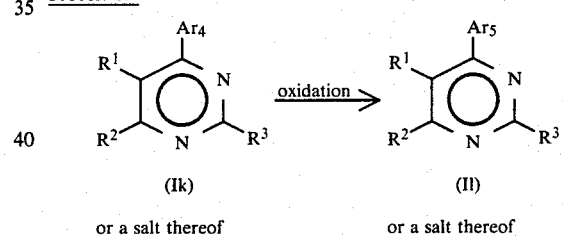

(Ik)       (Il)

or a salt thereof    or a salt thereof

Process 9:

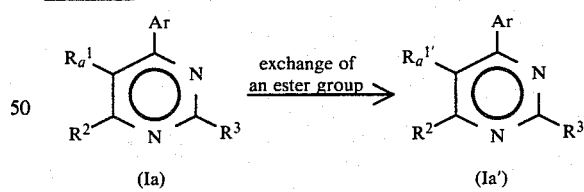

(Ia)       (Ia')

or a salt thereof    or a salt thereof

Process 10:

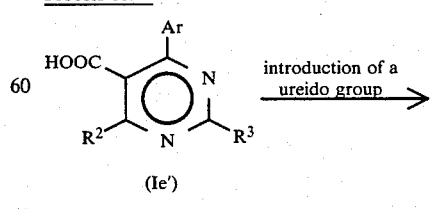

(Ie')

or its reactive derivative at the carboxy group or a salt thereof

-continued
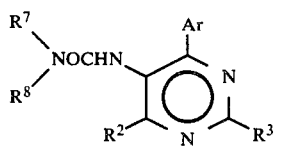
(Im)
or a salt thereof
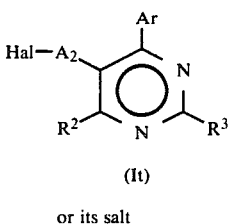
(It)
or its salt
Process 11:
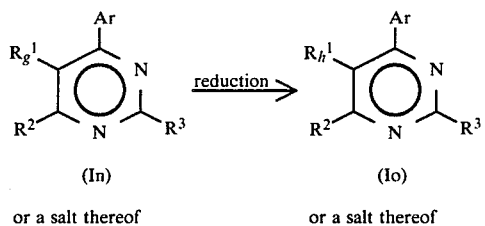
(In)                (Io)
or a salt thereof    or a salt thereof
Process 15:
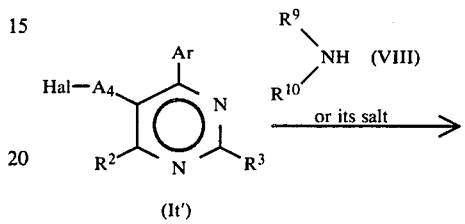
(It')
or its salt
Process 12:
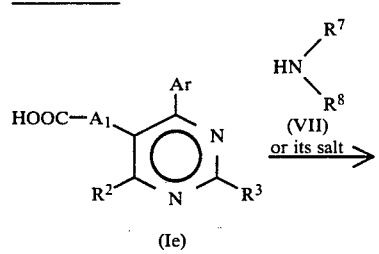 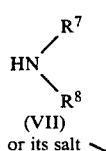
(Ie)
or its reactive derivatives
at the carboxy group
or a salt thereof
$$\xrightarrow{}$$
(Iu)
or its salt
Process 16:
(Ip)
or its salt
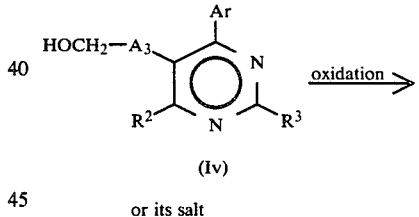
(Iv)
or its salt
Process 13:
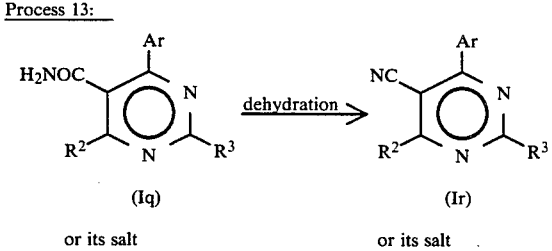
(Iq)              (Ir)
or its salt        or its salt
CHO—A₃ ...
(Iw)
or its salt
Process 14:
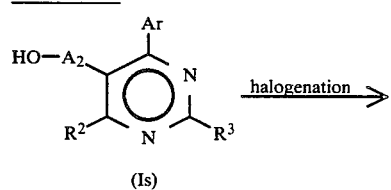
(Is)
or its salt
Process 17:
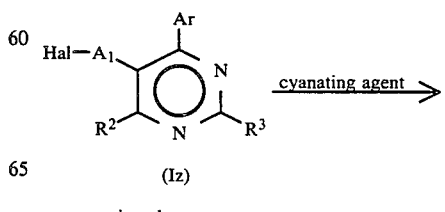
(Iz)
or its salt -continued Process 18:

(Iu) or its salt → (I₂) or its salt

Process 19:

(I₃) or its salt → (hydrolysis / esterification (optional)) → (I₄) or its salt

Process 20:

(Ij) or its salt → Introduction of N—containing heterocyclic group → (I₅) or its salt Process 21:

(I₁) or its salt (I₄′) or its salt → R¹¹—Y (IX) (alkylation) → (I₅′) or its salt Process 22:

(IVa) or its salt + (VI) or its salt → (I₆) or its salt

Process 23:

(X) or its salt + (VI) or its salt → (I₇) or its salt

Process 24:

(I₈) or a salt thereof → reduction → (I₉) or a salt thereof

Process 25:

(I₁₀) or a salt thereof + HCHO + (VII) or its salt → (I₁₁) or a salt thereof

Process 26:

-continued (I₁₂) or a salt thereof (I₁₃) or a salt thereof

Process 27:

(I_n) or a salt thereof (I₁₄) or a salt thereof wherein

Ar, $R^1$, $R^2$, $R^3$, $R^4$, $R^5$, $R^6$, $R^7$, $R^8$ and l are each as defined above;

$Ar_1$ is substituted aryl wherein at least one substituent is hydroxy, $Ar_2$ is substituted aryl wherein at least one substituent is lower alkanoyloxy, $Ar_3$ is substituted aryl wherein at least one substituent is halogen, $Ar_4$ is substituted aryl wherein at least one substituent is lower alkylthio, $Ar_5$ is substituted aryl wherein at least one substituent is lower alkanesulfinyl or lower alkanesulfonyl, $Ar_7$ is substituted aryl wherein at least one substituent is optionally substituted N-containing heterocyclic group, $Ar_8$ is substituted aryl wherein at least one substituent is nitro, $Ar_9$ is substituted aryl wherein at least one substituent is amino, $Ar_{10}$ is substituted aryl wherein at least one substituent is lower alkoxy, halo(lower)alkoxy or a group of the formula $$-O-(CH_2)_l-\underset{R^6}{\overset{R^4}{\bigcirc}}R^5$$

wherein $R^4$, $R^5$, $R^6$ and l are each as defined above, $R_a^1$ and $R_a^{1'}$ are each different esterified carboxy or esterified carboxy(lower)alkyl, $R_b^1$ is hydroxy(lower)alkyl, $R_c^1$ is lower alkyl, $R_d^1$ is carboxy or carboxy(lower)alkyl, $R_e^1$ is esterified carboxyamino, $R_g^1$ is lower alkanoyl, $R_h^1$ is hydroxy(lower)alkyl, $R_a^3$ is N-containing heterocyclic group, $R_b^3$ is N-containing heterocyclic group substituted with lower alkyl, $R^9$ and $R^{10}$ are each hydrogen or lower alkyl, or $R^9$ and $R^{10}$ are taken together to form optionally substituted N-containing heterocyclic group, $R^{11}$ is lower alkyl, $R^{12}$ is carboxy or esterified carboxy, $R^{13}$ and $R^{14}$ are each lower alkyl, $A_1$ and $A_3$ are each lower alkylene or a carbon to carbon bond, $A_2$ is a divalent radical of:
  lower alkylene-(pyrimidine ring side),
  lower alkylene-NHCO-(pyrimidine ring side),
  lower alkylene-NHCONH-(pyrimidine ring side) or
  lower alkylene-NHCO-lower alkylene-(pyrimidine ring side), $A_4$ is a divalent radical of:
  lower alkylene-NHCO-(pyrimidine ring side),
  lower alkylene-NHCONH-(pyrimidine ring side) or
  lower alkylene-NHCO-lower alkylene-(Pyrimidine ring side), Hal is halogen, and Y is an acid residue.

The methods for preparing the object compounds (I) of the present invention are explained in more details in the following.

PROCESS 1

The compound (I) and its salt can be prepared by oxidizing a compound (II) or its salt.

Suitable salts of the compound (II) are the same as the ones exemplified for the compound (I).

The oxidation reaction can be carried out by a conventional method which is applied for the transformation of a dihydropyrimidine ring to a pyrimidine ring, for example, by using an oxidizing agent such as manganese dioxide, nickel peroxide, sulfur powder, 2,3-dichloro-5,6-dicyano-1,4-benzoquinone, potassium permanganate, palladium on carbon or the like.

The present reaction is usually carried out in a solvent such as chloroform, pyridine, ethyl acetate, acetone, benzene, toluene or any other solvents which do not adversely affect the reaction.

The reaction temperature is not critical and the reaction is preferably carried out at ambient temperature or under warming or heating.

PROCESS 2

The compound (Ib) and its salt can be prepared by reducing a compound (Ia) or its salt.

The reduction can be carried out by a conventional method, for instance, by chemical reduction using a reducing agent.

Preferred examples of the reducing agents to be used in the chemical reduction may include lithium aluminum hydride, diisobutyl aluminum hydride, diborane, sodium borohydride and the like.

The reaction is usually carried out in a solvent such as water, diethyl ether, alcohol (e.g. methanol, ethanol, etc.) tetrahydrofuran, toluene, dichloromethane, or any other soluvents which do not adversely affect the reaction.

The reaction temperature is not critical, and the reaction is preferably carried out under cooling, at room temperature or under warming.

PROCESS 3

The compound (Id) and its salt can be prepared by subjecting a compound (Ia) or its salt to removal reaction of the ester group.

The removal reaction of this process can be conducted by a conventional method such as hydrolysis, reduction or the like.

The hydrolysis is preferably conducted in the presence of an acid (e.g. hydrochloric acid, sulfuric acid, acetic acid, trifluoroacetic acid, p-toluenesulfonic acid, etc.) or a base (e.g. sodium hydroxide, sodium ethoxide, triethylamine, etc.).

The reduction can be carried out by a conventional manner such as chemical reduction, catalytic reduction or the like.

The present invention is usually carried out in a solvent such as ethanol, benzene or any other solvents which do not adversely affect the reaction.

The reaction temperature is not critical and the reaction can be carried out at any temperature under cooling to heating.

PROCESS 4

The compound (If) and its salt can be prepared by subjecting a compound (Ie), its reactive derivative at the carboxy group or a salt thereof to introduction reaction of the esterified carboxyamino group.

Suitable reactive derivatives at the carboxy group of the compound (Ie) may include an acid halide, an acid anhydride, an activated ester and the like.

The present reaction is carried out by reacting a compound (Ie), its reactive derivative at the carboxy group or a salt thereof, with an azide compound (e.g., diphenylphosphoryl azide, sodium azide, etc.), and then by reacting the resultant compound with an alcohol for introducing an ester moiety.

The former reaction is preferably carried out in the presence of a base such as triethylamine, pyridine, or the like.

The present reactions are usually carried out successively in a solvent such as butanol, benzene, toluene, tetrahydrofuran or the like.

The reaction temperature is not critical, and the reactions are preferably carried out at ambient temperature or under warming or heating.

PROCESS 5

The compound (Ig) and its salt can be prepared by subjecting a compound (If) or its salt to removal reaction of the esterified carboxy group.

The reaction of this process can be conducted in substantially the same manner as that of Process 3.

Accordingly, the reaction mode and the reaction conditions of this process are to be referred thereto.

PROCESS 6

The compound (Ii) and its salt can be prepared by reacting a compound (Ih) or its salt with an acylating agent.

Suitable acylating agent may include lower alkanoic acid, its reaction derivative and the like.

The reaction derivatives may be an acid halide, an acid anhydride, an activated amide, an activated ester or the like. These reaction derivatives are selected according to the kind of the acid to be used.

In case a free acid is used as an acylating agent, the reaction may preferably be conducted in the presence of a conventional condensing agent.

The present reaction is usually carried out in a solvent such as tetrahydrofuran, or any other solvents which do not adversely affect the reaction.

The reaction temperature is not critical, and the reaction is preferably carried out under cooling, at room temperature or under warming.

PROCESS 7

The compound (Ik) and its salt can be prepared by reacting a compound (Ij) or its salt with a lower alkanethiol or its salt.

Suitable salts of the lower alkanethiol may include a metal salt such as an alkali metal salt (e.g., sodium salt, potassium salt, etc.), an alkaline earth metal salt (e.g., magnesium salt, etc.) and the like.

The present reaction may be conducted in the presence of an organic or inorganic base such as triethylamine, pyridine, sodium bicarbonate or the like.

The reaction is usually carried out in a solvent such as tetrahydrofuran, dimethylformamide, dimethylsulfoxide or any other solvents which do not adversely affect the reaction.

The reaction temperature is not critical, and the reaction is preferably carried out under cooling, at ambient temperature, or under warming.

PROCESS 8

The compound (Il) and its salt can be prepared by oxidizing a compound (Ik) or its salt.

The present oxidation reaction can be carried out by a conventional method which is applied for the transformation of —S— into —SO— or —SO$_2$—, for example by using an oxidizing agent such as m-chloroperbenzoic acid, perbenzoic acid, peracetic acid, ozone, hydrogen peroxide, periodic acid or the like.

The present reaction is usually carried out in a solvent such as water, acetone, dioxane, acetonitril, chloroform, methylene chloride, ethyl acetate or any other solvents which do not adversely affect the reaction.

The reaction temperature is not critical, and the reaction is preferably carried out under cooling or at ambient temperature.

PROCESS 9

The compound (Ia') and its salt can be prepared by subjecting a compound (Ia) or its salt to the exchange reaction of the ester group.

The present reaction can be conducted by reacting a compound (Ia) or its salt with an alcohol for introducing a different ester moiety from the one in the group of $R_a{}^1$.

The reaction may be carried out in the presence of an acid or base (e.g., methanesulfonic acid, hydrogen chloride, p-toluenesulfonic acid, sulfuric acid, sodium alkoxide, 1,8-diazabicyclo[5.4.0]undec-7-ene, triethylamine, etc.).

The reaction is usually carried out in a solvent such as alcohol, toluene, benzene, or any other solvents which do not adversely affect the reaction.

The reaction temperature is not critical, and the reaction is preferably carried out at ambient temperature or under warming or heating.

PROCESS 10

The compound (Im) and its salt can be prepared by subjecting a comound (Ie'), its reactive derivative at the carboxy group or a salt thereof to introduction reaction of the ureido group.

Suitable reactive derivatives at the carboxy group may include an acid halide, an acid anhydride, an activated ester and the like.

The present reaction can be conducted by reacting a compound (Ie'), its reactive derivative at the carboxy group or a salt thereof with an azide compound (e.g., diphenylphosphoryl azide, sodium azide, etc.), and then by reacting the resultant compound with ammonia or an amine compound having one or two groups mentioned above as substituents on the ureido group.

The reactions are usually carried out successively in a solvent such as benzene, toluene, tetrahydrofuran, or any other solvents which do not adversely affect the reaction.

The reaction temperature is not critical, and the reactions are preferably carried out at room temperature or under warming or heating.

The former present reaction is preferably carried out in the presence of a base such as triethylamine, pyridine, or the like.

PROCESS 11

The compound (Io) and its salt can be prepared by reducing a compound (In) or its salt.

The reaction of this process can be conducted in substantially the same manner as that of Process 2, and accordingly the particulars of this reaction are to be referred thereto.

PROCESS 12

The compound (Ip) and its salt can be prepared by reacting a compound (Ie) or its reactive derivative at the carboxy group or a salt thereof with a compound (VII) or its salt.

Suitable salts of the compound (VII) may be the same as those exemplified for the compound (I).

Suitable reactive derivatives at the carboxy group of the compound (Ie) may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

This reaction is usually carried out in a conventional solvent such as water, methanol, ethanol, propanol, tetralin, tetrahydrofuran, dioxane, chloroform, toluene, dimethylformamide, dimethylsulfoxide or any other organic solvent which does not adversely influence the reaction.

This reaction is preferably conducted in the presence of a conventional base such as an alkali metal hydride [e.g. sodium hydride, potassium hydride, etc.], an alkaline earth metal hydride [e.g. calcium hydride, magnesium hydride, etc.], an alkali metal hydroxide [e.g. sodium hydroxide, potassium hydroxide, etc.], an alkali metal carbonate or bicarbonate [e.g. sodium carbonate, potassium carbonate, sodium bicarbonate, potassium bicarbonate, etc.], or the like.

In case that the compound (Ie) is a free acid or its salt, the reaction is preferably conducted in the presence of a conventional condensing agent [e.g. N,N'-dicyclohexylcarbodiimide, etc.].

The reaction temperature is not critical, and the reaction can be carried out under cooling to heating.

PROCESS 13

The compound (Ir) and its salt can be prepared by dehydrating a compound (Iq) or its salt.

The reaction can be conducted by treating the compound (Iq) or its salt with a dehydrating agent such as phosphorus oxychloride, phosphorus pentoxide, phosphorus pentachloride, anhydrous titanium (IV) chloride or the like.

The reaction is usually carried out in a conventional solvent such as dichloroethane, dimethylformamide, pyridine, or any other solvent which does not adversely affect the reaction.

The reaction temperature is not critical, and the reaction is preferably carried out at room temperature, under warming or heating.

PROCESS 14

The object compound [It] and its salt can be prepared by halogenating a compound [Is] or its salt.

Suitable examples of the halogenating agent to be used in this process may include a conventional ones such as phosphorus oxyhalide [e.g. phosphorus oxybromide, phosphorus oxychloride, etc.), phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.], or the like.

This reaction is usually carried out in a conventional solvent such as methylene chloride, chloroform, carbon tetrachloride, benzene, tetrahydrofuran, dimethylformamide, dimethyl sulfoxide or any other organic solvent which does not adversely influence the reaction. In case that the halogenating agent is liquid, it can be used as a solvent.

The reaction temperature is not critical, and the reaction can be carried out under cooling to heating.

PROCESS 15

The object compound (Iu) and its salt can be prepared by reacting a compound (It) or its salt with a compound (VIII) or its salt. Suitable salts of the compound (VIII) may be the same as those exemplified for the compound (I).

This reaction is preferably conducted in the presence of an inorganic base such as an alkali metal hydride [e.g. sodium hydride, potassium hydride, etc.], an alkaline earth metal hydride [e.g. calcium hydride, magnesium hydride, etc.], an alkali metal hydroxide [e.g. sodium hydroxide, potassium hydroxide, etc.], an alkali metal carbonate or bicarbonate [e.g. sodium carbonate, potassium carbonate, sodium bicarbonate, potassium bicarbonate, etc.], or the like.

The present reaction is also preferably carried out in the presence of alkali metal halide (e.g., sodium iodide potassium iodide, etc.).

This reaction is usually carried out in a conventional solvent such as water, methanol, ethanol, isopropyl alcohol, dioxane, tetrahydrofuran, dimethylformamide, methylene chloride, chloroform or any other organic solvent which does not adversely influence the reaction.

The reaction temperature is not critical and the reaction can be carried out under cooling to heating.

PROCESS 16

The compound (Iw) and its salt can be prepared by oxidizing a compound (Iv) or its salt.

The present reaction can be conducted according to a conventional method oxidizing a hydroxymethyl group to give a formyl group, e.g., the oxidation using an oxidizing agent such as sodium metaperiodate, manganese dioxide, lead tetraacetate, potassium permanganate, chromium trioxide and the like. The reaction is usually conducted in a solvent such as water, methanol, ethanol, tetrahydrofuran, ethyl acetate, chloroform or any other solvent which does not adversely affect the reaction.

The reaction temperature is not critical and the reaction is preferably carried out under ice cooling, at room temperature or under warming.

PROCESS 17

The compound ($I_1$) and its salt can be prepared by reacting a compound (Iz) or its salt with a cyanating agent.

Preferred examples of the cyanating agent to be used in this process may include an alkalimetal cyanide (e.g., sodium cyanide, potassium cyanide, etc.), di-alkylalminum cyanide (e.g., diethylalminum cyanide, etc.) and the like.

The reaction is usually conducted in a solvent such as water, alcohol (e.g., methanol, ethanol, propanol, etc.), dimethylsulfoxide, methylene chloride, tetrahydrofuran or the like.

This reaction is preferably conducted under somewhat milder conditions such as under cooling, at room temperature or under warming.

PROCESS 18

The compound ($I_2$) and its salt can be prepared by reacting a compound (Iu) or its salt with an alkylating agent (IX).

The reaction of this process is usually conducted in a solvent such as water, alcohol (e.g., methanol, ethanol, propanol, etc.), dimethylsulfoxide, ethyl acetate, tetrahydrofuran or the like.

This reaction may preferably be conducted in the presence of an organic or inorganic base conventionally used in alkylation reaction.

The reaction is preferably conducted under somewhat milder conditions such as under cooling, at room temperature, or under warming.

PROCESS 19

The compound ($I_4$) and its salt can be prepared by hydrolyzing a compound ($I_3$) or its salt an then optionally esterifying the resultant compound.

The present reaction can be conducted in the presence of an acid or a base. Preferred examples of the acid may include an inorganic acid (e.g. hydrochloric acid, hydrobromic acid, sulfuric acid, etc.), an organic acid (e.g., formic acid, acetic acid, trifluoroacetic acid, propionic acid, benzenesulfonic acid, p-toluenesulfonic acid, etc.), and the like.

Preferred examples of the base may include an inorganic base such as alkali or alkaline earth metal hydroxide or the corresponding carbonate or bicarbonate (e.g. sodium hydroxide, potassium hydroxide, sodium carbonate, potassium carbonate, sodium bicarbonate, calcium hydroxide, etc.), ammonium hydroxide or the like; an organic base such as an alkoxide or phenoxide of the above metal (e.g. sodium ethoxide, sodium methoxide, etc.), an amine such as mono-, di- or tri-alkylamine (e.g. methylamine, ethylamine, N,N-dimethyl-1,3-propanediamine, trimethylamine, triethylamine, etc.) or the like.

The reaction is preferably conducted under somewhat milder conditions such as under cooling at ambient temperature or under warming in a solvent which does not adversely influence the reaction such as water, alcohol (e.g. methanol, ethanol, propanol, etc.), dimethylsulfoxide, methylene chloride, tetrahydrofuran or the like. In case the acid or the base is liquid, it can also be used as a solvent.

In case an alcohol is used as a solvent, the resultant carboxy compound is converted to an ester compound during the course of the reaction, and such a case is also included within the scope of this process.

PROCESS 20

The object compound [$I_5$] and its salt can be prepared by subjecting a compound [Ij] or its salt to the introduction reaction of the optionally substituted N-containing heterocyclic group.

This reaction can be carried out by reacting the compound [Ij] or its salt with the corresponding N-containing heterocyclic compound.

The reaction may be conducted in the presence of a conventional organic or inorganic base.

The reaction is usually carried out in a conventional solvent which does not adversely influence the reaction such as methanol, ethanol, dioxane, dimethylformamide, methylenechloride or the like. In case that the heterocyclic compound is liquid, it can also be used as a solvent.

The reaction temperature is not critical, and the reaction can be carried out under cooling to heating.

PROCESS 21

The compound ($I_5'$) and its salt can be prepared by reacting a compound ($I_4'$) or its salt with an alkylating agent (IX).

The reaction can be carried out substantially in the same manner as that of Process 18. Accordingly, the reaction mode and conditions can be referred thereto.

PROCESS 22

The compound ($I_6$) and its salt can be prepared by reacting a compound (IVa) or its salt with a compound (VI) or its salt.

Suitable salts of the compound (VI) may be the same as those exemplified for the compound (I).

The reaction may be conducted in the presence of a base such as triethylamine, pyridine, piperazine piperidine or the like.

The reaction is usually carried out in a solvent such as benzene, methanol, ethanol, n-butanol or any other solvent which does not adversely affect the reaction.

The reaction mixture is not critical and the reaction is preferably carried out at ambient temperature or under warming.

PROCESS 23

The compound ($I_7$) and its salt can be prepared by reacting a compound (X) or its salt with a compound (VI) or its salt.

Suitable salts of the compounds (VI) and (X) may be the same as those exemplified for the compound (I).

The reaction may be conducted in the presence of a base such as triethylamine, pyridine, piperazine piperidine or the like.

The reaction is usually carried out in a solvent such as benzene, methanol, ethanol, n-butanol or any other solvent which does not adversely affect the reaction.

The reaction temperature is not critical and the reaction is preferably carried out at ambient temperature or under warming.

PROCESS 24

The compound ($I_9$) and its salt can be prepared by reducing a compound ($I_8$) or its salt.

The reduction can be carried out by a conventional method, for example, by using a reducing agent such as lithium borohydride, sodium borohydride, potassium borohydride, sodium cyanoborohydride or lithium aluminum, hydride etc.; by chemical reduction using metal (e.g., zinc, iron, copper, etc.) and acid (e.g., hydrochloric acid, sulfuric acid, etc.), or metal (e.g., sodium, lithium, zinc, etc.) and base (e.g. ammonium, sodium hydroxide, etc.); or by catalytic reduction. The catalytic reduction is usually carried out in the presence of a conventional catalyst, such as Raney nickel, palladium, platinum, rhodium, copper, etc. preferably at ambient temperature under atmospheric pressure and in a conventional solvent. The reduction using a reducing agent is usually carried out in a conventional solvent, preferably a polar solvent, such as water, alcohol, and the like.

The present reaction can be conducted under cooling or slightly elevated temperature.

PROCESS 25

The compound ($I_{11}$) and its salt can be prepared by reacting a compound ($I_{10}$) or its salt with a compound (VII) or its salt in the presence of formaldehyde.

Suitable salts of the compound (VII) may be the same as those exemplified for the compound (I).

This reaction can be conducted according to a similar manner to that of the Mannich Reaction.

More specifically, this reaction can be carried out by warming or heating in the presence or absence of a conventional solvent such as alcohol (e.g. methanol, ethanol, propanol, etc.), halogenated hydrocarbon (e.g. dichloroethane, chloroform, carbon tetrachloride, etc.), or any other organic solvent which does not adversely influence the reaction.

PROCESS 26

The compound ($I_{13}$) and its salt can be prepared by reacting a compound ($I_{12}$) or its salt with a compound of the formula $$Y-Q \quad (XI)$$

wherein
Y is as defined above, and
Q is lower alkyl, halo(lower)alkyl or a group of the formula —(CH$_2$)$_l$—[phenyl ring with substituents R$^4$, R$^5$, R$^6$]

in which $R^4$, $R^5$, $R^6$ and l are each as defined above.

This reaction can be carried out according to a similar manner to that of the Process 15.

PROCESS 27

The compoud ($I_{14}$) and its salt can be prepared by reacting a compound ($I_n$) or its salt with a metal hypobromite.

This reaction is usually carried out in a conventional solvent such as water, methanol, ethanol, isopropyl alcohol, dioxane, tetrahydrofuran, dimethylformamide, methylene chloride, chloroform or any other organic solvent which does not adversely influence the reaction.

Suitable examples of metal of the metal hypobromite may be sodium, potassium, lithium or the like.

This reaction can optionally be conducted in the presence of an inorganic base such as an alkali metal hydride [e.g. sodium hydride, potassium hydride, etc.], an alkaline earth metal hydride [e.g. calcium hydride, magnesium hydride, etc.], an alkali metal hydroxide [e.g. sodium hydroxide, potassium hydroxide, etc.], an alkali metal carbonate or bicarbonate [e.g. sodium carbonate, potassium carbonate, sodium bicarbonate, potassium bicarbonate, etc.9 , or the like.

The present reaction is also preferably carried out in the presence of alkali metal halide (e.g. sodium iodide potassium iodide, etc.).

The reaction temperature is not critical, and the reaction can be carried out at room temperature, under warming to heating.

The object compound (Ia) to (Iz), ($I_1$) to ($I_{14}$), (Ia') and (I) and their salts prepared in the above processes can be isolated from the reaction mixture and purified by a conventional manner.

All of the compounds (Ia) to (Iz), ($I_1$) to ($I_{14}$), and (Ia') are included in the scope of the compound (I), and accordingly the salts of the compounds (Ia) to (Iz), ($I_1$) to ($I_{14}$) and (Ia') are to be referred to the salts of the compounds (I).

Among the starting compounds in the above processes, some of the compounds (II) are novel and can be prepared by the processes as illustrated in the following.

Process A $$\underset{(III)}{\overset{Ar_6}{\underset{|}{CHO}}} \quad \xrightarrow{\text{(i) } R^1-CH_2-CO-R^2 \text{ (V)}}$$

$$\underset{(IV)}{\overset{Ar_6}{\underset{|}{CH=C}}\diagdown\overset{CO-R^2}{\underset{R^1}{}}} \quad \xrightarrow[\text{(ii) or its salt}]{R^3-C\diagup\overset{NH}{\diagdown NH_2} \text{ (VI)}} \quad \underset{(IIa)}{\overset{Ar_6}{\underset{R^2\diagup\underset{N}{}\diagdown R^3}{R^1\diagup\diagdown NH}}}$$

or its salt

Process B $$\underset{(IIIa)}{\overset{Ar}{\underset{|}{CHO}}} \quad \xrightarrow{\text{(i) } R_i^1-CH_2-CO-R^2 \text{ (Va)}}$$

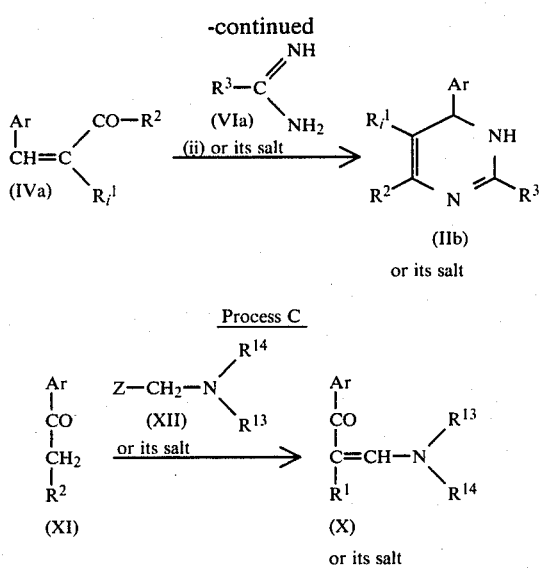

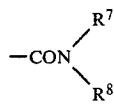

wherein
Ar, $R^1$, $R^2$, $R^3$ are each as defined above;
$Ar_6$ is optionally substituted heterocyclic group containing one nitrogen atom and/or sulfur atom(s); and
$R_j{}^1$ is lower alkanoyl, carbamoyl, esterified carboxy or a group of the formula:

$$-CON\begin{matrix}R^7\\R^8\end{matrix}$$

(wherein $R^7$ and $R^8$ are each as defined above)
Z is lower alkoxy or halogen.

The methods for preparing the starting compounds (II) of the present invention are explained in more details in the following.

PROCESSES A AND B (1) The compounds (IV) and (IVa) can be prepared by reacting a compound (III) or (IIIa) with a compound (V) or (Va), respectively.

The reaction may be conducted in the presence of a base such as triethylamine, pyridine, piperazine, piperidine or the like.

The reaction is usually carried out in a solvent such as benzene, toluene or the like, preferably at room temperature or under warming or heating.

(2) The compounds (IIa) and (IIb) and their salts can be prepared by reacting a compound (IV) or (IVa) with a compound (VI) or (VIa) or a salt thereof, respectively.

The reaction may be conducted in the presence of a base (e.g., triethylamine, pyridine, piperidine, etc.).

The reaction is usually carried out in a solvent such as benzene, alcohol (e.g. methanol, ethanol, etc.) or the like, preferably at room temperature or under warming or heating.

PROCESS C

The compound (X) and its salt can be prepared by reacting a compound (XI) with a compound (XII) or its salt.

The reaction is usually carried out in a solvent such as benzene, toluene or the like, preferably under cooling, at ambient temperature or under warming.

The starting compound (II) include tautomeric isomers represented by the formulae:

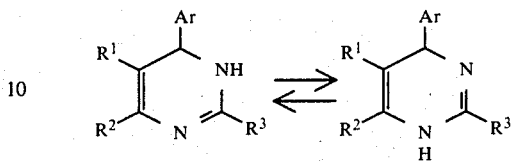

wherein Ar, $R^1$, $R^2$ and $R^3$ are as defined above, and it is to be noted that both of the tautomeric forms of the starting compounds (II) are included within the scope of the present invention.

And further, it is to be noted that the starting compounds (II) are also useful in the treatment of cerebrovascular disease.

The pyrimidine derivative (I) and their pharmaceutically acceptable salts have been found to be useful in the treatment of cerebrovascular diseases such as cerebral apoplexy (e.g. cerebral hemorrhage, cerebral infarction, transient cerebral ischemic attack) or the like.

For the purpose of showing utility of the Compound (I), pharmacological test data thereof are illustrated in the following.

TEST 1

Effect on Lipid Peroxide Production in Rat Brain Mitochondria

Method

Brain mitochondria from male Wistar rat was incubated with 100 $\mu$M ascorbic acid, 20 $\mu$M $FeSO_4$ and test drug for 1 hr at 37° C. Malondialdehyde formed in the incubation mixture was measured by the thiobarbituric acid method according to Shimada et al (Biochem. Biophys. Acta, 489; 163–172. 1977)

Test compound

Test compounds were dissolved in water

Results

| Compounds | Inhibition % at $10^{-4}$ g/ml | at $10^{-5}$ g/ml |
|---|---|---|
| Example 26 | 90.9 | — |
| Example 21 | — | 72.8 |
| Example 36 | — | 70.2 |

The compounds listed in the table inhibited significantly the malondialdehyde formation in rat brain mitochondria at the dose of $10^{-4}$ g/ml.

TEST 2

Effect on Survival Time of Mice Subjected to Anoxia (100% $N_2$)

Method

A pair of male ICR mice with the same age was maintained in a close glass chamber in which circulated a current of nitrogen gas, and measured survival time. One mouse was pretreated intraperitoneally with the test compound, and another with the vehicle 30 min before the experiment.

Test compound

Test compounds were dissolved in saline.

Result

| Com- | | Survival time (sec) | | | |
|---|---|---|---|---|---|
| pounds | n | Control | 10 mg/kg | Control | 100 mg/kg |
| Example 32 | 10 | 30.5 ± 0.5 | 37.0 ± 1.5** | 39.0 ± 1.2 | 50.0 ± 1.1** |

Compared with control
*P < 0.05
**P < 0.01

Pretreatment of mice with test compounds resulted in a statistically significant increase of survival time of animals subjected to anoxia in a dose of 10 mg/kg and more.

TEST 3

Effect on Arachidonic Acid-Induced Cerebral Edema in Rat

Method

Male wistar rats were anesthetized with ethyl ether. The right lingual and occipital arteries were ligated. Retrograde cannulation was performed at the bifurcation of the external and internal carotid arteries via the upper part of the right external artery. Arachidonic acid dissolved in 10% ethyl alcohol and 0.4% $Na_2CO_3$ was injected into the internal carotid artery in a dose of 2 mg/0.2 ml/kg at a speed of 0.08 ml/min. Two hours after the injection of arachidonic acid, the animals were decapitated and water content in the infarcted and contralatelal hemisphere was measured. The test drug was administered intraperitoneally 30 min before the injection of arachidonic acid.

Test compound

Test compounds were dissolved in saline.

Result

| | | Dose | Water content (%) | |
|---|---|---|---|---|
| Compounds | N | mg/kg | Infarcted hemisphere | Contralatelal hemisphere |
| (1) Vehicle | 10 | 0 | 81.9 ± 0.4 | 78.7 ± 0.4 |
| Example 32 | 6 | 10 | 80.2 ± 0.1** | 79.0 ± 0.3 |
| Example 32 | 6 | 32 | 79.9 ± 0.1** | 79.3 ± 0.2 |
| (2) Vehicle | 10 | 0 | 81.5 ± 0.4 | 79.4 ± 0.2 |
| Example 21 | 6 | 32 | 79.7 ± 0.3** | 78.6 ± 0.1 |
| (3) Vehicle | 10 | 0 | 81.5 ± 0.4 | 79.4 ± 0.2 |
| Example 36 | 6 | 32 | 79.5 ± 0.2** | 78.9 ± 0.1 | compared with control
*P < 0.05
**P < 0.01

Arachidonic acid injection into internal carotid artery caused increase of water content of the ipsilatelal hemisphere. The test compounds suppressed significantly the increase of water content in the ipsilatelal hemisphere in a dose of 10 and 32 mg/kg.

The object compounds (I) and pharmaceutically acceptable salts of this invention can be used in a form of a conventional pharmaceutical preparation, for example, in solid, semisolid or liquid form, which contains an active substance of this invention in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing thickening and coloring agents and perfumes may be used. The pharmaceutical compositions can also contain preservative or bacteriostatic agents to keep the active ingredient in the desired preparations stable in activity. The active object compound is included in the pharmaceutical composition in the amount sufficient to produce the desired therapeutic effect upon the process or condition of diseases.

While a dosage or therapeutically effective amount of the object compound (I) of this invention varies according to the age and conditions of each individual patient to be treated, a daily dose of about 0.1-100 mg/kg of the active ingredient is generally given for treating diseases.

The following Preparations and Examples are given for the purpose of illustrating this invention.

PREPARATION 1

A mixture of ethyl 2-[2-(4-chlorobenzyloxy)-benzylidene]acetoacetate (10 g), acetamidine hydrochloride (3.16 g), and triethylamine (4.23 g) in n-butanol (100 ml) was refluxed for 3.5 hours. The reaction mixture, added ethyl acetate (100 ml), was washed with water (100 ml) and 5% hydrochloric acid (100 ml) successively. The solvent was evaporated and the residual crystalline was stirred with ethyl acetate (50 ml) for 1 hour. The crystals were collected by filtration dried in vacuo to afford ethyl 2,4-dimethyl-6-[2-(4-chlorobenzyloxy)phenyl]-1,6-dihydro-5-pyrimidinecarboxylate hydrochloride (2.45 g).

mp: 212°-215° C.

IR (Nujol): 3175, 1710, 1695, 1270, 1240, 1005 $cm^{-1}$.

NMR (DMSO-$d_6$, δ): 1.00 (3H, t, J=7 Hz), 2.25 (3H, s), 2.28 (3H, s), 3.95 (2H, q, J=7 Hz), 5.20 (2H, s), 5.87 (1H, br s), 6.8-7.8 (8H, m), 11.60 (1H, s), 11.97 (1H, s).

PREPARATION 2

A mixture of 2-(4-hydroxy-3-nitrobenzylidene)acetylacetone (40 g), benzamidine hydrochloride (30.2 g) and triethylamine (31.2 ml) in n-butanol (400 ml) was refluxed for 2 hours. The reaction mixture, added ethyl acetate (100 ml), was washed with water (200 ml) and 5% hydrochloric acid (200 ml) successively. The solvent was evaporated and the residue was stirred with ethyl acetate (200 ml) for 1 hour. The crystals were collected by filtration, added a mixture of chloroform (200 ml) and water (200 ml) and adjusted to pH 8.5 by saturated potassium carbonate. The organic layer was evaporated in vacuo to give crude 5-acetyl-1,6-dihydro-6-(4-hydroxy-3-nitrophenyl)-4-methyl-2-phenylpyrmidine (45.5 g).

mp: 191°-192° C.

IR (Nujol): 1665, 1595, 1530 $cm^{-1}$.

NMR (DMSO-$d_6$, δ): 2.18 (3H, s), 2.42 (3H, s), 5.7 (1H, s), 6.97-8.0 (8H, m).

Mass: 351.

PREPARATION 3

A mixture of N-(2-dimethylaminoethyl)-2-(3-nitrobenzylidene)acetoacetamide (4 g), n-butanol (40 ml), benzamidine hydrochloride (2.26 g) and triethylamine (2.4 ml) was refluxed for 2.5 hours.

After evaporating the solvent, the residue was dissolved in a suspension of water (100 ml) and chloroform (100 ml), adjusted to pH 5.0 with 10% aqueous hydrochloric acid. Then the separated aqueous layer was adjusted to pH 9.0 with 10% aqueous sodium carbonate and extracted with chloroform (100 ml). The organic layer was washed with saturated aqueous sodium chloride, dried over magnesium sulfate and evaporated in vacuo. The residue was subjected to column chromatography on alumina (100 g) and eluted with chloroform. The fractions containing the object compound were combined and concentrated under reduced pressure. The residue was recrystallized from diethyl ether to give N-(2-dimethylaminoethyl)-1,6-dihydro-4-methyl-6-(3-nitrophenyl)-2-phenyl-5-pyrimidinecarboxamide.

mp: 131°–133° C.
IR (Nujol): 1670, 1620 cm$^{-1}$.
NMR (CDCl$_3$, δ): 2.10 (6H, s), 2.26 (2H, t, J=6 Hz), 2.30 (3H, s), 3.23 (2H, t, d, J=6 Hz J=6 Hz), 5.72 (1H, s), 6.17 (1H, t, J=6 Hz), 7.1–8.3 (10H, m).
Mass (E/Z): 407 (M+).

PREPARATION 4

The following compounds were prepared according to a similar manner to that of Preparation 1, 2 or 3.

(1) Ethyl 4-methyl-2-phenyl-6-(4-pyridyl)-1,6-dihydro-5-pyrimidinecarboxylate.
mp: 147°–150° C.
Elemental Analysis Calcd. C, 71.01; H, 5.96; N, 13.07.
Anal. C, 70.94; H, 5.98; N, 13.01.
IR (Nujol): 3150, 1690, 1645, 1590, 1240, 1090 cm$^{-1}$.
NMR (DMSO-d$_6$, δ): 1.15 (3H, t, J=7 Hz), 2.40 (3H, s), 4.05 (2H, q, J=7 Hz), 5.70 (1H, s), 7.1–7.6 (5H, m), 7.7–8.1 (2H, m), 8.2–8.8 (2H, m), 9.57 (1H, br s).
Mass (M+) 321.

(2) Ethyl 4-methyl-2-phenyl-6-(3-pyridyl)-1,6-dihydro-5-pyrimidinecarboxylate.
mp: 138°–139° C.
IR (Nujol): 1695, 1680, 1580, 1240, 1085 cm$^{-1}$.
NMR (DMSO-d$_6$, δ): 1.13 (3H, t, J=7 Hz), 2.40 (3H, s), 4.03 (2H, q, J=7 Hz), 5.67 (1H, s), 7.2–8.1 (7H, m), 8.3–8.7 (2H, m), 9.60 (1H, br).
Mass (M+) 321.

(3) Ethyl 4-methyl-2-phenyl-6-(2-pyridyl)-1,6-dihydro-5-pyrimidinecarboxylate.

(4) Ethyl 6-(4-cyanophenyl)-4-methyl-2-phenyl-1,6-dihydro-5-pyrimidinecarboxylate.
mp: 148°–149° C.
IR (Nujol): 2250, 1680 cm$^{-1}$.
NMR (DMSO-d$_6$, δ): 1.13 (3H, t, J=7 Hz), 2.4 (3H, s), 4.07 (2H, q, J=7 Hz), 5.73 (1H, s), 7.73–8.0 (9H, m), 9.53 (1H, br).
Mass (M) 345.

(5) Ethyl 6-(3-cyanophenyl)-4-methyl-2-phenyl-1,6-dihydro-5-pyrimidinecarboxylate.
mp: 135°–136° C.
IR (Nujol): 3480, 2250, 1700, 1660 cm$^{-1}$.
NMR (DMSO-d$_6$, δ): 1.13 (3H, t, J=7 Hz), 2.4 (3H, s), 4.08 (2H, q, J=7 Hz), 5.73 (1H, s), 7.3–8.0 (9H, m), 9.53 (1H, br).

(6) Ethyl 6-[2-(4-chlorobenzyloxy)phenyl]-4-methyl-2-phenyl-1,6-dihydro-5-pyrimidinecarboxylate.
IR (CHCl$_3$): 3505, 1670, 1590 cm$^{-1}$.
NMR (DMSO-d$_6$, δ): 1.0 (3H, t, 7 Hz), 2.37 (3H, s), 3.93 (2H, q, 7 Hz), 5.17 (2H, s), 6.07 (1H, s), 6.73–7.9 (13H, m), 9.17 (1H, br).

(7) Ethyl 4-methyl-6-[2-(4-chlorobenzyloxy)phenyl]-2-phenyl-1,6-dihydro-5-pyrimidinecarboxylate hydrochloride.
mp: 134°–136° C.
IR (Nujol): 1718, 1680, 1635, 1100, 995 cm$^{-1}$.
NMR (DMSO-d$_6$, δ): 1.03 (3H, t, J=7 Hz), 2.58 (3H, s), 4.03 (2H, q, J=7 Hz), 5.20 (2H, s), 5.97 (1H, s), 6.8–8.0 (13H, m), 11.87 (2H, br).

(8) Ethyl 2,4-dimethyl-6-(3-pyridyl)-1,6-dihydro-5-pyrimidinecarboxylate.
mp: 139°–140° C.
IR (Nujol): 1690, 1680, 1635, 1295, 1225, 1100 cm$^{-1}$.
NMR (DMSO-d$_6$, δ): 1.03 (3H, t, J=7 Hz), 1.88 (3H, s), 2.23 (3H, s), 4.00 (2H, q, J=7 Hz), 5.40 (1H, s), 7.1–7.7 (2H, m), 8.2–8.7 (2H, m).
Mass (M+) 259.

(9) Ethyl 6-[2-(4-chlorobenzyloxy)phenyl]-2,4-dimethyl-1,6-dihydro-5-pyrimidinecarboxylate.
mp: 171°–173° C.
IR (Nujol): 1690, 1515 cm$^{-1}$.
NMR (DMSO-d$_6$, δ): 1.3 (3H, t, 7 Hz), 1.77 (3H, s), 2.23 (3H, s), 3.9 (2H, q, 7 Hz), 5.17 (2H, s), 5.9 (1H, s), 6.73–7.23 (8H, m), 8.97 (1H, m).

(10) 5-Acetyl-4-methyl-2-phenyl-6-(4-pyridyl)-1,6-dihydropyrimidine.
IR (Nujol): 1600, 1245, 690 cm$^{-1}$.
NMR (DMSO-d$_6$, δ): 2.20 (3H, s), 2.47 (3H, s), 5.82 (1H, s), 7.2–7.7 (5H, m), 7.8–8.1 (2H, m) 8.3–8.7 (2H, m).
Mass (M+) 291.

(11) 5-Acetyl-4-methyl-6-(3-nitrophenyl)-2-phenyl-1,6-dihydropyrimidine.
mp: 154°–155° C.
IR (Nujol): 1655, 1590, 1530, 1340, 1245 cm$^{-1}$.
NMR (DMSO-d$_6$, δ): 2.23 (3H, s), 2.50 (3H, s), 5.93 (1H, s), 7.3–8.2 (9H, m), 9.60 (1H, s).
Mass (M+) 335.

(12) 2-Phenyl-4-(4-pyridyl)-5-oxo-3,4,5,7-tetrahydrofuro[3,4-d]pyrimidine.

(13) 4-(3-Nitrophenyl)-2-phenyl-5-oxo-3,4,5,7-tetrahydrofuro[3,4-d]pyrimidine.
NMR (DMSO-d$_6$, δ): 4.77 (2H, s), 5.87 (1H, s), 7.4–8.37 (9H, m).

(14) Ethyl 2-methyl-4-phenyl-6-(4-pryridyl)-1,6-dihydro-5-pyrimidinecarboxylate.
mp: 173°–175° C.
Elemental Analysis Calcd. C, 71.01; H, 5.96; N, 13.07.
Found C, 71.37; H, 5.92; N, 13.12.
NMR (DMSO-d$_6$, δ): 0.73 (3H, t, J=7 Hz), 1.95 (3H, s), 3.73 (2H, q, J=7 Hz), 5.46 (1H, s), 7.2–7.52 (7H, m), 8.4–8.63 (2H, m), 9.48 (1H, s).
Mass 321.

(15) Ethyl 6-[2-(4-chlorophenylthio)phenyl]-4-methyl-2-phenyl-1,6-dihydro-5-pyrimidinecarboxylate hydrochloride.
mp: 186°–189° C.
IR (Nujol): 1720, 1670, 1635, 1540, 1235, 1095 cm$^{-1}$.
NMR (DMSO-d$_6$, δ): 1.07 (3H, t, J=7 Hz), 2.47 (3H, s), 4.00 (2H, q, J=7 Hz), 6.27 (1H, s), 7.0–8.0 (13H, m).

(16) Ethyl 6-(3,4-dimethoxyphenyl)-4-methyl-2-phenyl-1,6-dihydro-5-pyrimidinecarboxylate hydrochloride.
mp: 223°–227° C.
IR (Nujol): 1715, 1670, 1625, 1260, 1240, 1100, 1020, 690 cm$^{-1}$.
NMR (DMSO-d$_6$, δ): 1.16 (3H, t, J=7 Hz), 2.60 (3H, s), 3.75 (3H, s), 3.79 (3H, s), 4.15 (2H, q, J=7 Hz), 5.73 (1H, s), 6.8–7.3 (3H, m), 7.5–8.2 (5H, m), 12.50 (2H, br).

(17) Ethyl 6-(3,4-dimethoxyphenyl)-4-methyl-2-phenyl-1,6-dihydro-5-pyrimidinecarboxylate.
IR (CHCl$_3$): 1690, 1600, 1100.

NMR (DMSO-d$_6$, δ): 1.16 (3H, t, J=7 Hz), 2.37 (3H, s), 3.7 (6H, s), 4.06 (2H, q, J=7 Hz), 5.53 (1H, s), 6.7-6.96 (3H, m), 7.36-7.5 (3H, m), 7.76-7.86 (2H, m), 9.0-9.5 (1H, br).
Mass (M+) 380.
(18) Ethyl 4-methyl-6-(4-hydroxy-3-nitrophenyl)-2-phenyl-1,6-dihydro-5-pyrimidinecarboxylate.
mp.: 179°-180° C.
IR (Nujol): 1720, 1675, 1610, 1545, 1505 cm$^{-1}$.
NMR (DMSO-d$_6$, δ): 1.17 (3H, t, J=7 Hz), 2.4 (3H, s), 4.07 (2H, q, 7 Hz), 5.63 (1H, s), 7.03-7.27 (8H, m).
Mass 381.
(19) Ethyl 6-[2-(4-chlorobenzyloxy)-3-nitrophenyl]-4-methyl-2-phenyl-1,6-dihydro-5-pyrimidinecarboxylate.
mp: 168°-169° C.
IR (Nujol): 1705, 1665, 1600, 1530, 805 cm$^{-1}$.
NMR (DMSO-d$_6$, δ): 1.00 (3H, t, J=7 Hz), 2.52 (3H, s), 4.00 (2H, q, J=7 Hz), 5.50 (2H, q-like, J=10 Hz), 6.20 (1H, s), 7.3-8.1 (12H, m), 9.60 (1H, s).
(20) Ethyl 6-(4-chloro-3-nitrophenyl)-4-methyl-2-phenyl-1,6-dihydro-5-pyrimidinecarboxylate.
IR (Film): 1710, 1605, 1175 cm$^{-1}$.
NMR (DMSO-d$_6$, δ): 1.17 (3H, t, J=7 Hz), 2.45 (3H, s), 4.13 (2H, t, J=7 Hz), 5.87 (1H, s), 7.47-7.68 (3H, m), 7.7-7.87 (2H, m), 7.87-8.07 (3H, m), 9.77 (1H, s).
(21) Ethyl 6-[2-(4-chlorobenzyloxy)-5-nitrophenyl]-4-methyl-2-phenyl-1,6-dihydro-5-pyrimidinecarboxylate.
mp: 167°-169° C.
IR (Nujol): 1690, 1660, 1335 cm$^{-1}$.
NMR (DMSO-d$_6$, δ): 1.00 (3H, t, J=7 Hz), 2.43 (3H, s), 4.95 (2H, q, J=7 Hz), 5.37 (2H, s), 6.13 (1H, s), 7.0-8.3 (12H, m), 9.37 (1H, s).
(22) Ethyl 6-(2-chloro-5-nitrophenyl)-4-methyl-2-phenyl-1,6-dihydro-5-pyrimidinecarboxylate.
mp: 169°-170° C.
IR (Nujol): 1740, 1710, 1660, 1610, 1580, 1530 cm$^{-1}$.
NMR (DMSO-d$_6$, δ): 1.03 (3H, t, J=7 Hz), 2.53 (3H, s), 3.97 (2H, q, J=7 Hz), 6.13 (1H, s), 7.37-7.56 (3H, m), 7.67-7.9 (3H, m), 8.0-8.17 (2H, m), 9.63 (1H, br)
Mass 399.
(23) Ethyl 6-(3-methoxy-5-nitro-4-hydroxyphenyl)-4-methyl-2-phenyl-1,6-dihydro-5-pyrimidinecarboxylate.
IR (Nujol): 1670 cm$^{-1}$.
NMR (DMSO-d$_6$, δ): 1.17 (3H, t, J=7 Hz), 2.4 (3H, s), 3.8 (3H, s), 4.07 (2H, q, J=7 Hz), 5.58 (1H, s), 7.13-8.0 (7H, m).
Mass 411.
(24) Ethyl 6-(3-methoxyphenyl)-4-methyl-2-phenyl-1,6-dihydro-5-pyrimidinecarboxylate.
IR (Film): 1665, 1605, 1590 cm$^{-1}$.
NMR (DMSO-d$_6$, δ): 1.17 (3H, t, J=7 Hz), 2.43 (3H, s), 3.75 (3H, s), 4.1 (2H, q, J=7 Hz), 5.63 (1H, s), 6.67-7.0 (3H, m), 7.0-7.27 (1H, m), 7.28-7.62 (3H, m), 7.67-8.0 (2H, m), 9.4 (1H, br)
Mass 350.
(25) Ethyl 6-(4-methoxycarbonylphenyl)-4-methyl-2-phenyl-1,6-dihydro-5-pyrimidinecarboxylate.
IR (Film): 2930, 1585 cm$^{-1}$.
NMR (DMSO-d$_6$, δ): 1.13 (3H, t), 2.4 (3H, s), 3.82 (3H, s), 4.08 (2H, q, J=7 Hz), 5.73 (1H, s), 7.33-8.37 (9H, m), 9.48 (1H, s).
Mass 378.

(26) 5-Acetyl-4-methyl-6-(4-nitrophenyl)-2-phenylpyrimidine.
IR (CHCl$_3$): 3325, 1655, 1600, 1350 cm$^{-1}$.
NMR (DMSO-d$_6$, δ): 2.23 (3H, s), 2.45 (3H, s), 5.87 (1H, s), 7.3-7.7 (5H, m), 7.7-8.0 (2H, m), 8.17 (2H, dd, J=9 Hz), 2 Hz), 9.57 (1H, s).
Mass (M+) 335.
(27) 1,6-Dihydro-4-methyl-6-(3-nitrophenyl)-2-phenyl-5-pyrimidinecarboxamide.
mp: 204°-206° C.
IR (Nujol): 3350, 1678, 1598 cm$^{-1}$.
NMR (DMSO-d$_6$, δ): 2.28 (3H, s), 5.77 (1H, s), 7.00 (2H, br.), 7.2-8.2 (9H, m), 9.07 (1H, br.).
(28) 5-Acetyl-1,6-dihydro-6-(4-chloro-3-nitrophenyl)-4-methyl-2-phenylpyrimidine.
IR (CHCl$_3$): 1650, 1595 cm$^{-1}$.
NMR (DMSO-d$_6$, δ): 2.25 (3H, s), 2.47 (3H, s), 5.83 (1H, s), 7.33-7.67 (5H, m), 7.73-8.0 (3H, m), 9.6 (1H, br.).
Mass: 369.
(29) Ethyl 1,6-dihydro-6-(3-hydroxy-4-nitrophenyl)-4-methyl-2-phenyl-5-pyrimidinecarboxylate.
mp: 174°-175° C.
IR (Nujol): 3350, 1719, 1675, 1615 cm$^{-1}$.
NMR (DMSO-d$_6$, δ): 1.17 (3H, t, J=7 Hz), 2.4 (3H, s), 4.08 (2H, q, J=7 Hz), 5.62 (1H, s), 6.83-7.12 (2H, m), 7.33-7.62 (3H, m), 7.67-8.0 (3H, m).
Mass: 381.
(30) Ethyl 1,6-dihydro-4-methyl-6-(3-nitrophenyl)-2-(3-pyridyl)-5-pyrimidinecarboxylate.
IR (CHCl$_3$): 2950, 1690 cm$^{-1}$.
NMR (DMSO-d$_6$, δ): 1.18 (3H, t, J=7 Hz), 2.45 (3H, s), 4.17 (2H, q, J=7 Hz), 5.73 (1H, s), 7.23-7.83 (3H, m), 7.9-8.3 (3H, m), 8.58 (1H, dd, J=2, 6 Hz), 8.95 (1H, d, J=2 Hz), 9.67 (1H, br.).
Mass: 366.
(31) Ethyl 1,6-dihydro-4-methyl-2-phenyl-6-(3-trifluoromethylphenyl)-5-pyrimidinecarboxylate.
mp: 136°-138° C.
IR (Nujol): 1695, 1655, 1505 cm$^{-1}$.
NMR (DMSO-d$_6$, δ): 1.13 (3H, t, J=7 Hz), 2.4 (3H, s), 4.05 (2H, q, J=7 Hz), 5.57, 5.93 (total 1H, each s), 7.37-7.67 (7H, m), 7.7-8.0 (2H, m), 9.33, 9.5 (total 1H, each br.).
Mass: 388.
(32) 2-Methyl-4-[2-(4-chlorobenzyloxy)phenyl]-5-oxo-3,4,5,7-tetrahydrofuro[3,4-d]pyrimidine. hydrochloride.
mp: 198°-200° C.
IR (Nujol): 1760, 1720, 1600, 1245, 1000 cm$^{-1}$.
NMR (DMSO-d$_6$, δ): 2.27 (3H, s), 4.90 (2H, s), 5.13 (2H, s), 5.97 (1H, s), 6.8-7.8 (4H, m), 7.17 (4H, s).
(33) 2-Methyl-4-[2-(4-nitrobenzyloxy)phenyl]-5-oxo-3,4,5,7-tetrahydrofuro[3,4-d]pyrimidine hydrochloride.
mp: 281°-282° C.
IR (Nujol): 1765, 1720, 1600, 1350, 1020 cm$^{-1}$.
NMR (DMSO-d$_6$, δ): 2.30 (3H, s), 4.97 (2H, s), 5.33 (2H, s), 6.00 (1H, s), 6.8-7.8 (4H, m), $$\begin{pmatrix} 7.80 \\ 8.30 \end{pmatrix} \begin{pmatrix} 4H, ABq, \\ J=8Hz \end{pmatrix}$$

(34) 4-(2,3-Dimethoxyphenyl)-2-methyl-5-oxo-3,4,5,7-tetrahydrofuro[3,4-d]pyrimidine.
mp: 188°-190° C.

IR (Nujol): 1750, 1660, 1280, 990 cm$^{-1}$.
NMR (DMSO-d$_6$, δ): 1.93 (3H, s), 3.76 (3H, s), 3.87 (3H, s), 4.70 (2H, s), 5.73 (1H, s), 6.8–7.3 (3H, s).

(35) 2-Methyl-4-(3-nitrophenyl)-5-oxo-3,4,5,7-tetrahydrofuro[3,4-d]pyrimidine.
mp: 219°–220° C. (dec.)
IR (Nujol): 3325, 1725, 1640, 1530, 1350, 1215 cm$^{-1}$.
NMR (DMSO-d$_6$, δ): 2.07 (3H, s), 4.77 (2H, s), 5.80 (1H, s), 7.5–8.3 (4H, m).
Mass: 273 (M$^+$).

(36) 2-Methyl-5-oxo-4-(2-trifluoromethylphenyl)-3,4,5,7-tetrahydrofuro[3,4d]pyrimidine.
mp: 211°–213° C.
IR (Nujol): 3300, 1720, 1650, 1315, 1090 cm$^{-1}$.
NMR (DMSO-d$_6$, δ): 2.0 (3H, s), 4.73 (2H, s), 5.76 (1H, s), 7.3–8.0 (4H, m), 8.96 (1H, br. s).
Mass: 296 (M$^+$).

(37) 2-Methyl-4-(2-nitrophenyl)-5-oxo-3,4,5,7-tetrahydrofuro[3,4-d]pyrimidine.
mp: 172°–174° C. (dec.).
IR (Nujol): 3275, 1720, 1640, 1520, 1070 cm$^{-1}$.
NMR (DMSO-d$_6$, δ): 2.0 (3H, s), 4.77 (2H, s), 6.23 (1H, s), 7.4–8.2 (4H, m), 9.03 (1H, br.).

(38) 4-(3,4-Dimethoxyphenyl)-2-methyl-5-oxo-3,4,5,7-tetrahydrofuro[3,4-d]pyrimidine.
mp: 168°–171° C.
IR (Nujol): 3250, 1710, 1645, 1210, 1010, 850 cm$^{-1}$.
NMR (DMSO-d$_6$, δ): 2.0 (3H, s), 3.73 (6H, s), 4.70 (2H, s), 5.45 (1H, s), 6.6–7.1 (3H, m), 9.0 (1H, br.).
Mass: 288 (M$^+$).

(39) 2-Methyl-4-[2,(2-methylbenzyloxy)]phenyl-5-oxo-3,4,5,7-tetrahydrofuro[3,4-d]pyrimidine hydrochloride.
mp: 242°–243° C.
IR (Nujol): 1760, 1715, 1600, 980 cm$^{-1}$.
NMR (DMSO-d$_6$, δ): 2.17 (3H, s), 2.28 (3H, s), $\begin{smallmatrix}4.67\\4.90\end{smallmatrix}\left(\begin{smallmatrix}2H, ABq,\\J=18Hz\end{smallmatrix}\right)$, 5.13 (2H, s), 5.90 (1H, s), 6.67–7.67 (8H, m), 11.0–12.5 (2H, br.)

(40) Ethyl 1,6-dihydro-6-(4,5-dimethoxyphenyl-2-nitro)-4-methyl-2-phenyl-5-pyrimidinecarboxylate.
mp: 166°–168° C.
IR (CHCl$_3$): 3430, 2970, 1680, 1600, 1580, 1050, 860 cm$^{-1}$.
NMR (CDCl$_3$, δ): 1.03 (3H, t, J=7 Hz), 2.60 (3H, s), 3.83 (3H, s), 3.90 (3H, s), 4.02 (2H, g, J=7 Hz), 6.23 (1H, s), 6.97 (1H, s), 7.53 (1H, s), 7.2–7.9 (5H, m).
Mass: (EI) M$^+$ 425.

(41) Ethyl 1,6-dihydro-6-(2-methoxyphenyl)-4-methyl-2-phenyl-5-pyrimidinecarboxylate.
mp: 243–244° C.
IR (Nujol): 1705, 1685, 1630, 1600, 1585, 1540, 1265, 1235, 1025, 870 cm$^{-1}$.
NMR (DMOS-d$_6$, δ): 1.13 (3H, t, J=7 Hz), 2.57 (3H, s), 3.87 (3H, s), 4.10 (2H, q, J=7 Hz), 5.90 (1H, s), 6.9–8.1 (9H, m), 12.0–12.5 (2H, br.).

(42) Ethyl 1,6-dihydro-2,4-dimethyl-6-(3,4-dimethoxy-6-nitrophenyl)-5-pyrimidinecarboxylate.
mp: 156°–160° C.
IR (Nujol): 1690, 1670 (shoulder), 1610, 1100, 1050, 720 cm$^{-1}$.
NMR (DMOS-d$_6$, δ): 1.00 (3H, t, J=7 Hz), 1.87 (3H, s), 2.30 (3H, s), 3.77 (3H, s), 3.83 (3H, s), 6.07 (1H, s), 6.87 (1H , s), 7.43 (1H, s).

(43) Ethyl 1,6-dihydro-6-(2-methoxyphenyl)-2,4-dimethyl-5-pyrimidinecarboxylate hydrochloride.
mp: 180°–182° C.
IR (Nujol): 3150, 1700, 1675, 1550, 1240, 1100, 750 cm$^{-1}$.
NMR (DMSO-d$_6$, δ): 1.03 (3H, t, J=7 Hz), 2.33 (3H, s), 2.38 (3H, s), 3.83 (3H, s), 4.00 (2H, q, J=7 Hz), 5.78 (1H, s), 6.8–7.6 (4H, m), 11.57 (1H, br. s), 12.37 (1H, br. s).

(44) Ethyl 1,6-dihydro-2,4-dimethyl-6-[2-(4-nitrobenzyloxy)phenyl]-5-pyrimidinecarboxylate hydrochloride.
mp: 232°–233° C. (dec.).
IR (Nujol): 3375, 3150, 1750, 1680, 1600, 1520, 1240 cm$^{-1}$.
NMR (DMSO-d$_6$, δ): 1.00 (3H, t, J=7 Hz), 2.27 (6H, s), 3.98 (2H, q, J=7 Hz), 5.35 (2H, s), 5.90 (1H, s), 6.8–7.5 (4H, m), $\begin{smallmatrix}7.80\\8.27\end{smallmatrix}\left(\begin{smallmatrix}4H, ABq,\\J=9Hz\end{smallmatrix}\right)$

(45) Ethyl 1,6-dihydro-6-(3,4-dimethoxyphenyl)-2,4-dimethyl-5-pyrimidinecarboxylate hydrochloride.
mp: 173°–176° C.
IR (Nujol): 1700, 1655, 1260, 1240, 860, 800 cm$^{-1}$.
NMR (DMSO-d$_6$, δ): 1.10 (3H, t, J=7 Hz), 2.36 (3H, s), 2.43 (3H, s), 3.77 (3H , s), 3.78 (3H, s), 4.07 (2H, q, J=7 Hz), 5.57 (1H, s), 6.7–7.2 (3H, m).

(46) Ethyl 1,6-dihydro-2,4-dimethyl-6-[4-(4-chlorobenzyloxy)phenyl]-5-pyrimidinecarboxylate hydrochloride.
mp: 166°–168° C.
IR (Nujol): 1715, 1620, 1525, 1240, 1180, 808, 723 cm$^{-1}$.
NMR (DMSO-d$_6$, δ): 1.08 (3H, t, J=7 Hz), 2.40 (3H, s), 2.43 (3H, s), 4.07 (2H, q, J=7 Hz), 5.17 (2H, s), 5.57 (1H, s), $\begin{smallmatrix}7.07\\7.35\end{smallmatrix}\left(\begin{smallmatrix}4H, ABq,\\J=8Hz\end{smallmatrix}\right)$, 7.50 (4H, s), 12.0–12.5 (2H, br.).

(47) Ethyl 1,6-dihydro-2,4-dimethyl-6-[3,(4-chlorobenzyloxy)phenyl]-5-pyrimidinecarboxylate hydrochloride.
mp: 198°–200° C.
IR (Nujol): 3160, 1705, 1675, 1600, 1240, 1040, 800 cm$^{-1}$.
NMR (DMSO-d$_6$, δ): 1.06 (3H, t, J=7 Hz), 2.41 (3H, s), 2.44 (3H, s), 4.03 (2H, q, J=7 Hz), 5.13 (2H, s), 5.57 (1H, s), 6.8–7.6 (8H, m), 12.30 (2H, s).

(48) Ethyl 1,6-dihydro-6-[2-(2,4-dichlorobenzyloxy)phenyl]-2,4-dimethyl-5-pyrimidinecarboxylate hydrochloride.
mp: 165°–168° C.
IR (Nujol): 3150, 1715, 1680, 1555, 1230, 1100, 1005, 810 cm$^{-1}$.
NMR (DMSO-d$_6$, δ): 0.97 (3H, t, J=7 Hz), 2.16 (6H, s), 3.85 (2H, q, J=7 Hz), 5.10 (2H, s), 5.70 (1H, s), 6.7–7.6 (7H, m), 11.16 (2H, br. s, W ½ 15 Hz)

(49) Ethyl 1,6-dihydro-2,4-dimethyl-6-[2-(4-methoxybenzyloxy)phenyl]-5-pyrimidinecarboxylate hydrochloride.

mp: 135°–139° C.

IR (Nujol): 3150, 1705, 1680, 1610, 1560, 1510, 1240, 1030, 820, 760 cm$^{-1}$.

NMR (DMSO-$d_6$, δ): 1.00 (3H, t, J=7 Hz), 2.23 (3H, s), 2.30 (3H, s), 3.77 (3H, s), 3.97 (2H, q, J=7 Hz), 5.12 (2H, s), 5.82 (1H, s), 6.6–7.6 (8H, m), 11.53 (1H, br.), 11.93 (1H, br.)

(50) Ethyl 1,6-dihydro-4-methyl-6-[2-(4-nitrobenzyloxy)phenyl]-2-phenyl-5-pyrimidinecarboxylate.

NMR (DMSO-$d_6$, δ): 1.03 (3H, t, J=7 Hz), 2.45 (3H, s), 3.96 (3H, q, J=7 Hz), 5.4 (2H, s), 6.2 (1H, s), 6.98–8.4 (13H, m), 7.23 (1H, s).

Mass: 471.

(51) Ethyl 6-(2-chloro-5-nitrophenyl-1,6-dihydro-4-methyl-2-(3-pyridyl)-5-pyrimidinecarboxylate mp: 101°–102° C.

NMR (DMSO-$d_6$, δ): 1.03 (3H, t, J=7 Hz), 2.5 (3H, s), 3.97 (2H, q, J=7 Hz), 6.15 (1H, s), 7.33–8.25 (5H, m), 8.55–9.0 (2H, m), 9.75 (1H, br.).

Mass (M/Z): 400, 402.

(52) Methyl 1,6-dihydro-4-ethyl-6-(3-nitrophenyl)-2-phenyl-5-pyrimidinecarboxylate.

mp: 135°–136° C.

IR (Film): 3350, 2970, 1740, 1710, 1663, 1585, 1535, 1485, 1355 cm$^{-1}$.

NMR (DMSO-$d_6$, δ): 1.19 (3H, t, J=7 Hz), 2.83 (2H, q, J=7 Hz), 3.58 (3H, s), 5.76 (1H, s), 7.3–8.2 (9H, m), 9.6 (1H, br.)

Mass: 365.

(53) 1,6-Dihydro-N-(2-hydroxyethyl)-4-methyl-6-(3-nitrophenyl)-2-phenyl-5-pyrimidinecarboxamide.

mp: 148°–150° C.

IR (Nujol): 1670, 1635, 1605, 1530, 1350.

NMR (DMSO-$d_6$, δ) : 2.16 (3H, s), 3.0–3.6 (4H, m), 5.75 (1H, s), 7.25–8.25 (11H, m).

Mass (M/Z): 380(M+).

(54) Methyl 6-(2-chloro-5-nitrophenyl)-1,6-dihydro-4-methyl-2-phenyl-5-pyrimidinecarboxylate.

IR (Nujol): 1710, 1660, 1525, 1345 cm$^{-1}$.

NMR (DMSO-$d_6$, δ): 2.51 (3H, s), 3.52 (3H, s), 6.11 (1H, s), 7.25–8.3 (9H, m).

Mass (M/Z): 385, 387 (M+).

(55) 1,6-Dihydro-4-methyl-5-(4-methylpiprazin-1-ylcarbonyl)-2-phenyl-6-(3-trifluoromethylphenyl)pyrimidine.

IR (CHCl$_3$): 3400, 1610 cm$^{-1}$.

NMR (CDCl$_3$, δ): 0.7–1.1 (2H, m), 1.4–1.7 (2H, m), 1.85 (3H, s), 2.1 (3H, s), 2.0–3.3 (4H, m), 5.73 (1H, s), 7.3–7.9 (10H, m).

Mass (M/Z): 442 (M+).

(56) Methyl 1,6-dihydro-2-(4-chlorophenyl)-4-methyl-6-(3-nitrophenyl)-5-pyrimidinecarboxylate.

NMR (CDCl$_3$, δ): 2.46 (3H, s), 3.67 (3H, s), 5.86 (1H, s), 7.3–8.2 (9H, m).

(57) Methyl 1,6-dihydro-6-(3-hydroxyphenyl)-4-methyl-2-phenyl-5-pyrimidinecarboxylate.

Mass (M/Z): 322 (M+).

(58) Methyl 1,6-dihydro-4-methyl-6-(3-nitrophenyl)-2-(4-pyridyl)-5-pyrimidinecarboxylate.

NMR (DMSO-$d_6$, δ): 2.4 (3H, s), 3.55 (3H, s), 5.8 (1H, s), 7.5–8.9 (9H, m).

(59) 1,6-Dihydro-4-methyl-5-(4-methylpiperazin-1-ylcarbonyl)-6-(4-nitrophenyl)-2-phenylpyrimidine.

(60) Ethyl 1,6-dihydro-4-diethoxymethyl-6-(3-nitrophenyl)-2-phenyl-5-pyrimidinecarboxylate.

(61) 1,6-Dihydro-4-methyl-5-(4-methylpiperazin-1-ylcarbonyl)-6-(3-nitrophenyl)-2-phenylpyrimidine.

(62) 1,6-Dihydro-4-methyl-5-(4-methylpiperazin-1-ylcarbonyl)-6-(2-nitrophenyl)-2-phenylpyrimidine.

PREPARATION 5

A mixture of 3-nitrobenzaldehyde (20 g), acetylacetone (13.25 g), acetic acid (1.58 g), and piperidine (0.45 g) in benzene (20 ml) was refluxed for 1 hr under azeotropic dehydration. To the reaction mixture was added diethyl ether (100 ml). The mixture was washed with water (50 ml) and a saturated aqueous solution of sodium chloride (50 ml) successively, dried over magnesium sulfate, and evaporated in vacuo. The residual substance was recrystallized from ether to afford 3-(3-nitrobenzylidene)acetylacetone.

mp: 92°–95° C.

IR (Nujol): 1705, 1665, 1620, 915, 810 cm$^{-1}$.

NMR (DMSO-$d_6$, δ): 2.25 (3H, s), 2.47 (3H, s), 7.5–8.0 (3H, m), 8.1–8.5 (2H, m).

PREPARATION 6

A mixture of 4-hydroxy-3-nitrobenzaldehyde (43.5 g), acetylacetone (26 g), acetic acid (3.12 g) and piperidine (1.03 ml) in benzene (26 ml) was refluxed for 1 hours under azeotropic dehydration. To the reaction mixture was added 100 ml of diethyl ether. The mixture was washed with water (100 ml) and a saturated aqueous solution of sodium chloride (50 ml), dried over magnesium sulfate and evaporated in vacuo to afford 2-(4-hydroxy-3-nitrobenzylidene)acetylacetone (55.0 g).

IR (Nujol): 1690, 1650, 1605, 1540 cm$^{-1}$.

NMR (DMSO-$d_6$, δ): 2.25 (3H, s), 2.4 (3H, s), 7.22 (1H, d, J=8 Hz), 7.58 (1H, dd, J=2, 8 Hz), 7.67 (1H, s), 8.08 (1H, d, J=2 Hz).

Mass: 249.

PREPARATION 7

The following compounds were prepared according to the similar manners to that of Preparation 5 or 6.

(1) 3-(4-Pyridylidene)acetylacetone.

IR (Film): 1715, 1670, 1600, 815 cm$^{-1}$.

NMR (DMSO-$d_6$, δ): 2.25 (3H, s), 2.45 (3H, s), 7.2–7.5 (2H, m), 7.67 (1H, s), 8.5–8.8 (2H, m).

(2) Ethyl 2-(2-pyridylidene)acetoacetate.

(3) Ethyl 2-(4-pyridylidene)benzoylacetate.

NMR (DMSO-$d_6$, δ): 1.15 (3H, t, J=7 Hz), 4.25 (2H, q, J=7 Hz), 7.32 (2H, dd, J=2, 4 Hz), 7.5–8.07 (6H, m), 8.55 (2H, dd, J=2, 4 Hz)

(4) Ethyl 4-acetoxy-2-(4-pyridylidene)acetoacetate.

Mass: 278.

(5) Ethyl 2-(4-pyridylidene)acetoacetate.

IR (Film): 1725, 1600, 815 cm$^{-1}$.

NMR (DMSO-$d_6$, δ) 1.17 (3H, t, J=7 Hz, 2.36 (total 3H),
2.47 (each s), 4.28 (2H, q, J=7 Hz), 7.2–7.6 (2H, m), 7.67 (total 1H),
7.83 (each s), 8.5–8.8 (2H, m).

(6) Ethyl 2-(3-pylidylidene)acetoacetate.
IR (Film): 1700, 1620, 800 cm$^{-1}$.
NMR (DMSO-d$_6$, δ): 1.10 (3H, t, J=7 Hz), $\begin{matrix} 2.20 \\ 2.30 \end{matrix} \left( \begin{matrix} \text{total 3H} \\ \text{each s} \end{matrix} \right)$, 4.30 (2H, q, J=7 Hz), 7.2–8.1 (3H, m), 8.3–9.0 (2H, m)

(7) 3-(4-Nitrobenzylidene)acetylacetone.
mp: 80°–81° C.
IR (Nujol): 1710, 1660, 1600, 1345 cm$^{-1}$.
NMR (DMSO-d$_6$, δ): 2.29 (3H, s), 2.49 (3H, s), 7.67 (2H, dd, J=9 Hz, 2 Hz), 7.80 (1H, s), 8.25 (2H, dd, J=9 Hz, 2 Hz).

(8) Ethyl 2-(3-hydroxy-4-nitrobenzyliden)-acetoacetate
IR (CHCl$_3$): 1730, 1630, 1595 cm$^{-1}$.
NMR (DMSO-d$_6$, δ): 1.13, 1.16 (total 3H, each t, J=7 Hz), 2.30, 2.33 (total 3H, each s), 4.1, 4.25 (total 2H, each q, J=7 Hz), 6.86–8.0 (4H, m).

(9) Ethyl 2-(3-trifluoromethylbenzilidene)-acetoacetate.
NMR (DMSO-d$_6$, δ): 1.18 (3H, t, J=7 Hz), 2.45 (3H, s), 4.25 (2H, q, J=7 Hz), 7.67–7.97 (4H, m).
Mass: 286.

(10) Ethyl 2-[2-(4-chlorobenzyloxy)benzylidene]acetoacetate.
IR (Nujol): 1720, 1650, 800, 720 cm$^{-1}$.
NMR (DMSO-d$_6$, δ): 1.17 (3H, t, J=7 Hz), $\begin{matrix} 2.28 \\ 2.38 \end{matrix} \left( \begin{matrix} \text{total} \\ \text{3H} \end{matrix} \text{ each s} \right)$, 4.22 (2H, q, J=7 Hz), 5.23 (2H, s), 6.8–7.8 (8H, m), $\begin{matrix} 7.90 \\ 7.97 \end{matrix} \left( \begin{matrix} \text{total} \\ \text{1H,} \end{matrix} \text{ each s} \right)$

(11) Ethyl 2-[2-(4-nitrobenzyloxy)benzylidene]acetoacetate.
IR (Nujol): 1735, 1660, 1630, 1600, 1520, 1350, 755 cm$^{-1}$.
NMR (DMSO-d$_6$, δ): 1.17 (3H, t, J=7 Hz), 2.43 (3H, s), 4.23 (2H, q, J=7 Hz), 5.42 (2H, s), 6.8–8.5 (8H, m), 8.03 (1H, s).

(12) Ethyl 2-(4-hydroxy-3-nitrobenzylidene)acetoacetate.
IR (Nujol): 1730, 1660, 1620, 1045 cm$^{-1}$.
NMR (DMSO-d$_6$, δ): 1.27 (3H, t, J=7 Hz), 2.47 (3H, s), 4.33 (2H, q, J=7 Hz), 7.0–8.5 (4H, m).
Mass: 280.

(13) Ethyl 2-(3,4-dimethoxybenzylidene)acetoacetate.
IR (Nujol): 1720, 1660, 1625, 1600, 1150, 1020 cm$^{-1}$.
NMR (CDCl$_3$, δ): 1.33 (3H, t, 7 Hz), 2.40 (3H, s), 3.87 (3H, s), 3.90 (3H, s), 4.37 (2H, q, 7 Hz), 6.6–7.3 (3H, m), 7.50 (1H, s).

(14) Ethyl 2-[2-(4-methoxybenzyloxy)benzylidene]acetoacetate.
IR (Film): 2980, 1720, 1660, 1515, 1375, 1240, 1030, 820, 750 cm$^{-1}$.
NMR (DMSO-d$_6$, δ):

$\begin{matrix} 1.17 \\ 1.23 \end{matrix} \left( \begin{matrix} \text{total 3H,} \\ \text{each t, J = 7Hz} \end{matrix} \right)$, $\begin{matrix} 2.27 \\ 2.37 \end{matrix} \left( \begin{matrix} \text{total 3H,} \\ \text{each s} \end{matrix} \right)$, $\begin{matrix} 3.77 \\ 3.87 \end{matrix} \left( \begin{matrix} \text{total 3H,} \\ \text{each s} \end{matrix} \right)$, 4.33 (2H, q, J=7 Hz), 5.27 (2H, s), 7.0–7.9 (8H, m), $\begin{matrix} 8.10 \\ 8.13 \end{matrix} \left( \begin{matrix} \text{total 1H,} \\ \text{each s} \end{matrix} \right)$ Mass: 354 (M$^+$).

(15) Ethyl 2-[2-(2,4-dichlorobenzyloxy)benzylidene]-acetoacetate.
IR (Nujol): 1730, 1655, 1615, 1600, 1205, 1035 740 cm$^{-1}$.
NMR (DMSO-d$_6$, δ):

$\begin{matrix} 1.17 \\ 1.27 \end{matrix} \left( \begin{matrix} \text{total 3H,} \\ \text{each t,} \end{matrix} \text{ J = 7Hz} \right)$, $\begin{matrix} 2.27 \\ 2.37 \end{matrix} \left( \begin{matrix} \text{total 3H,} \\ \text{each s} \end{matrix} \right)$, 4.23 (2H, q, J=7 Hz), 5.30 (2H, s), 7.0–7.9 (7H, m), $\begin{matrix} 7.93 \\ 7.98 \end{matrix} \left( \begin{matrix} \text{total 1H} \\ \text{each s} \end{matrix} \right)$

(16) Ethyl 2-[3-(4-chlorobenzyloxy)benzylidene]acetoacetate.
IR (Film): 3980, 1720, 1660, 1620, 1490, 1010, 810 cm$^{-1}$.
NMR (DMSO-d$_6$, δ): 1.20 (3H, t, J=7 Hz), $\begin{matrix} 2.30 \\ 2.43 \end{matrix} \left( \begin{matrix} \text{total 3H,} \\ \text{each s} \end{matrix} \right)$, 4.25 (2H, q, J=7 Hz), 5.12 (2H, s), 7.0–7.7 (8H, m), $\begin{matrix} 7.60 \\ 7.73 \end{matrix} \left( \begin{matrix} \text{total 1H,} \\ \text{each s} \end{matrix} \right)$

(17) Ethyl 2-[4-(4-chlorobenzyloxy)benzylidene]acetoacetate.
IR (Nujol): 2980, 1720, 1600, 1505, 1245, 1170, 1010, 825 cm$^{-1}$.
NMR (DMSO-d$_6$, δ): 1.23 (3H, t, J=7 Hz), 2.36 (total 3H,
2.40 (each s), 4.30 (2H, q, J=7 Hz), 5.17 (total 2H,
5.23 (each s), 7.0-8.0 (9H, m).
(18) Ethyl 2-[2-(4-chlorophenylthio)benzylidene]acetoacetate.
IR (Film): 3000, 1725, 1480, 1245, 1098, 820 cm⁻¹
NMR (DMSO-d₆, δ):

1.07 (total 3H,
1.20 (each t, J=7Hz), 2.13 (total 3H,
2.33 (each s), 4.13 (2H, q, J=7 Hz), 7.1-7.7 (8H, m), 7.92 (total 1H,
7.98 (each s)

(19) Ethyl 2-[2-(4-chlorobenzyloxy)3-nitrobenzylidene]acetoacetate.
mp: 108°-110° C.
IR (Nujol): 1730, 1670, 1630, 1600, 1530, 805 cm⁻¹.
NMR (DMSO-d₆, δ): 1.10 (3H, t, J=7 Hz), 2.37 (3H, s), 4.23 (2H, q, J=7 Hz), 5.10 (2H, s), 7.3-8.3 (8H, m).
(20) Ethyl 2-[2-(4-chlorobenzyloxy)-5-nitrobenzylidene]acetoacetate.
mp: 122°-124° C.
IR (Nujol): 1740, 1668, 1515, 810 cm⁻¹.
NMR (DMSO-d₆, δ): 1.17 (3H, t, J=7 Hz), 2.33 (total 3H,
2.43 (each s), 4.27 (2H, q, J=7 Hz), 5.47 (2H, s), 7.4-7.8 (5H, m), 7.90 (total 1H,
8.00 (each s), 8.2-8.6 (2H, m)
(21) Ethyl 2-(3-methoxybenzylidene)acetoacetate
IR (Nujol): 1725, 1700, 1670, 1625, 1600, 1580 cm⁻¹.
NMR (DMSO-d₆, δ): 1.22 (3H, t, J=7 Hz), 2.47 (3H, s), 3.8 (3H, s), 4.27 (2H, q, J=7 Hz), 6.93-7.83 (5H, m).
(22) Ethyl 2-(2-chloro-5-nitrobenzylidene)acetoacetate.
IR (Nujol): 3100, 1730, 1610, 1575, 1530 cm⁻¹.
NMR (DMSO-d₆, δ): 1.12, 1.32 (total 3H, each t, J=7 Hz), 2.35, 2.53 (total, 3H, each s), 4.18, 4.32 (total 2H, each q, J=7 Hz), 7.7-8.57 (4H, m).
Mass: 297.

(23) Ethyl 2-(3,4-dimethoxybenzylidene)acetoacetate.
IR (Nujol): 1720, 1660, 1625, 1600, 1150, 1020 cm⁻¹.
NMR (CDCl₃, δ): 1.33 (3H, t, J=7 Hz), 2.40 (3H, s), 3.87 (3H, s), 3.90 (3H, s), 4.37 (2H, q, J=7 Hz), 6.6-7.3 (3H, m), 7.50 (1H, s).
(24) Ethyl 2-(3-cyanobenzilidene)acetoacetate.
NMR (DMSO-d₆, δ): 1.22 (3H, t, J=7 Hz), 2.48 (3H, s), 4.33 (2H, q, J=7 Hz), 7.6-8.13 (5H, m).
Mass: 243.
(25) Ethyl 2-(4-hydroxy-3-methoxy-5-nitrobenzilidene)acetoacetate.
IR (Nujol): 1740, 1660, 1615 cm⁻¹.
NMR (DMSO-d₆, δ): 1.23 (3H, t, J=7 Hz), 2.43 (3H, s), 3.88 (3H, s), 4.32 (2H, q, J=7 Hz), 7.4 (1H, d, J=2 Hz), 7.72 (1H, d, J=2 Hz), 7.7 (1H, s).
Mass: 309.
(26) Ethyl 2-(4-cyanobenzilidene)acetoacetate.
IR (CHCl₃): 2240, 1720 cm⁻¹.
NMR (DMSO-d₆, δ): 1.17 (3H, t, J=7 Hz), 2.35, 2.43 (total 3H, each s), 4.25 (2H, q, J=7 Hz), 7.43-8.07 (5H, m)
Mass: 243.
(27) Ethyl 2-(4-methoxycarbonylbenzilidene)-acetoacetate.
IR (Film): 3010, 2950, 1670, 1615, 1570, 1440 cm⁻¹.
NMR (DMSO-d₆, δ): 1.18, 1.28 (total 3H, each t J=7 Hz), 2.38, 2.47 (total 3H, each s), 3.87 (3H, s), 4.28 (2H, q, J=7 Hz), 7.47-8.17 (5H, m).
Mass: 276.
(28) Ethyl 2-(4-chloro-5-nitrobenzilidene)acetoacetate.
IR (Nujol): 1732, 1660, 1630, 1605, 1542 cm⁻¹.
NMR (DMSO-d₆, δ): 1.22 (3H, t, J=7 Hz), 2.5 (3H, s), 4.32 (2H, q, J=7 Hz), 7.67-8.0 (3H, m), 8.17-8.33 (1H, m).
Mass: 297.
(29) Ethyl 4-acetoxy-2-(2-trifluoromethylbenzylidene)-acetoacetate.
IR (Film): 1745, 1720, 1630, 1375, 1230 cm⁻¹.
NMR (DMSO-d₆, δ): 0.93, 1.28 (total 3H, each t, J=7 Hz), 2.03, 2.13 (total 3H, each s), 4.07, 4.3 (total 2H, each q, J=7 Hz), 4.87, 5.20 (total 2H, each s), 7.2-8.2 (5H, m).
(30) Ethyl 4-acetoxy-2-(3-nitrobenzylidene)acetoacetate
(31) Ethyl 4-acetoxy-2-[2-(4-nitrobenzyloxy)benzylidene]acetoacetate
IR (Nujol): 1760, 1730, 1690, 1600, 1520, 1350, 840 cm⁻¹.
NMR (DMSO-d₆, δ): 1.27 (3H, t, J=7 Hz), 2.08 (3H, s), 4.27 (2H, q, J=7 Hz), 4.93 (2H, s), 5.43 (2H, s), 6.8-8.5 (9H, m).
(32) Ethyl 4-acetoxy-2-(2-nitrobenzylidene)acetoacetate.
IR (Film): 3000, 2950, 1745, 1720, 1600, 1520, 1345 cm⁻¹.
NMR (DMSO-d₆, δ): 0.90, 1.30 (total 3H, each t, J=7 Hz), 2.0, 2.13 (total 3H, each s), 4.03, 4.32 (total 2H, each q, J=7 Hz), 4.82, 5.20 (total 2H, each s), 7.2-8.5 (5H, m).
(33) Ethyl 4-acetoxy-2-(3,4-dimethoxybenzylidene)-acetoacetate.
IR (Film): 2980, 2950, 1745, 1720, 1595, 1220, 1020 cm⁻¹.
NMR (DMSO-d₆, δ): 1.23, 1.27 (total 3H, each t, J=7 Hz), 2.13 (3H, s), 3.77 (3H, s), 3.83 (3H, s), 4.23, 4.30 (total 2H, each q, J=7 Hz), 5.0, 5.26 (total 2H, each s), 7.0-7.5 (3H, m), 7.73, 7.77 (total 1H, each s).

(34) Ethyl 4-acetoxy-2-[2-(2-methylbenzyloxy)benzylidene]acetoacetate

IR (Film): 2980, 2940, 1740, 1720, 1595, 1200, 740 cm$^{-1}$.

NMR (DMSO-d$_6$, δ): 1.00, 1.33 (total 3H, each t, J=7 Hz), 2.07 (3H, s), 2.33 (3H, s), 4.02 (2H, q, J=7 Hz), 4.73, 4.87 (total 2H, each s), 5.10, 5.20 (total 2H, each s), 7.0–7.7 (8H, m), 8.00, 8.08 (total 1H, each s).

(35) Ethyl 4-acetoxy-2-(3-nitrobenzilidene)acetoacetate.

(36) Methyl 2-(3-nitrobenzilidene)propioacetate.

IR (Film): 1725, 1615, 1535, 1440, 1355 cm$^{-1}$.

NMR (DMSO-d$_6$, δ): 1.03 (3H, t, J=7 Hz), 2.9 (2H, q, J=7 Hz), 3.76 (3H, s), 7.7–8.0 (3H, m), 8.15–8.43 (2H, m).

Mass: 263.

(37) N-(2-Hydroxyethyl)-2-(3-nitrobenzilidene)acetoacetamide mp: 117°–120° C.

IR (Film): 3250, 1670, 1625, 1565, 1525 cm$^{-1}$.

NMR (DMSO-d$_6$, δ): 2.4 (3H, s), 3.16–3.6 (4H, m), 4.3–4.7 (1H, br.), 7.60–8.60 (5H, m).

Mass: 278.

PREPARATION 8

To a solution of ethyl 4-nitrobenzoylacetate (11.9 g) in benzene (100 ml) was dropwise added N,N-dimethylformamide dimethylacetal (9.5 g) dissolved in benzene (50 ml) during a period of 0.5 hour, under stirring at room temperature. The mixture was refluxed for 4 hours. The reaction mixture was evaporated under reduced pressure. The resulting oil was recrystallized from ether-hexane to give 12.5 g of ethyl 2-(4-nitrobenzoyl)-3-dimethylaminopropenoate.

mp: 105°–107° C.

IR (Nujol): 1690, 1630, 1610, 1590, 1528, 1220, 1025 cm$^{-1}$.

NMR (CDCl$_3$, δ): 0.93 (3H, t, J=7 Hz), 3.1 (6H, s), 3.95 (2H, q, J=7 Hz), 7.7 (2H, dd, J=3, 8 Hz) 7.75 (1H, s), 8.16 (2H, dd, J=3, 8 Hz).

EXAMPLE 1

To a solution of ethyl 4-methyl-2-phenyl-6-(4-pyridyl)-1,6-dihydro-5-pyrimidinecarboxylate (13.4 g) in chloroform (300 ml) was added activated manganese dioxide (53.6 g) and the mixture was refluxed for two hours with stirring vigorously. After allowing to cool to room temperature, manganese dioxide was filtered off. The filtrate was evaporated in vacuo and the residual precipitate was recrystallized from a mixture of ether (80 ml) and petroleum ether (40 ml). The crystal was filtered off, washed with ether and dried in vacuo to give ethyl 6-methyl-2-phenyl-4-(4-pyridyl)-5-pyrimidinecarboxylate (7.5 g).

mp: 95°–96° C.

|  |  | C | H | N |
|---|---|---|---|---|
| Elemental Analysis | Calcd | 71.46 | 5.37 | 13.16 |
|  | Found | 71.28 | 5.52 | 12.94 |

IR (Nujol): 1715, 1600, 1530, 1265, 775, 690 cm$^{-1}$.

NMR (DMSO-d$_6$, δ): 1.05 (3H, t, J=7 Hz), 2.63 (3H, s), 4.15 (2H, q, J=7 Hz), 7.3–7.6 (5H, m), 8.2–8.4 (2H, m).

Mass (M$^+$) 319.

EXAMPLE 2

A mixture of methyl 1,6-dihydro-4-methyl-6-(3-nitrophenyl)-2-phenyl-5-pyrimidinecarboxylate (0.5 g) and sulfur powder (0.046 g) was heated at 150° C. for 1 hour. After cooling, the mixture was dissolved in chloroform and filtered. The filtrate was evaporated under reduced pressure to give a crystal of methyl 6-methyl-4-(3-nitrophenyl)-2-phenyl-5-pyrimidinecarboxylate (0.2 g).

mp: 127°–129° C. (recrystallized from diethyl ether).

IR (Nujol): 1723, 1538 cm$^{-1}$.

EXAMPLE 3

The following compounds were prepared according to the similar manner to that of Example 1 or 2.

(1) Ethyl 6-methyl-4-(3-nitrophenyl)-2-phenyl-5-pyrimidinecarboxylate.

mp: 97°–98° C.

|  |  | C | H | N |
|---|---|---|---|---|
| Elemental Analysis | Calcd. | 66.11 | 4.72 | 11.56 |
|  | Found | 66.34 | 4.87 | 11.65 |

IR (Nujol): 1720 cm$^{-1}$.

NMR (DMSO-d$_6$, δ): 1.12 (3H, t), 2.67 (3H, s), 4.28 (2H, q), 7.45–8.62 (9H, m).

Mass (M$^+$) 363.

(2) Ethyl 6-methyl-4-(4-nitrophenyl)-2-phenyl-5-pyrimidinecarboxylate.

mp: 138°–140° C.

IR (Nujol): 1715, 1605 cm$^{-1}$.

NMR (DMSO-d$_6$, δ): 1.06 (3H, t, J=7 Hz), 2.66 (3H, s), 4.23 (2H, q, J=7 Hz), 7.4–7.63 (3H, m), 7.8–8.0 (2H, m), 8.26–8.53 (4H, m)

Mass (M+1) 364.

(3) 5-Acetyl-6-methyl-4-(3-nitrophenyl)-2-phenylpyrimidine.

mp: 131°–132° C.

IR (Nujol): 1700, 1530, 1348, 1245 cm$^{-1}$.

NMR (DMSO-d$_6$, δ): 2.28 (3H, s), 2.60 (3H, s), 7.50–8.70 (9H, m).

Mass (M+1) 334.

(4) Ethyl 4-[2-(4-chlorobenzyloxy)phenyl]-6-methyl-2-phenyl-5-pyrimidinecarboxylate.

mp: 112°–113° c.

|  |  | C | H | N | Cl |
|---|---|---|---|---|---|
| Elemental Analysis | Calcd. | 70.66 | 5.05 | 6.10 | 7.72 |
|  | Found | 70.81 | 5.31 | 6.06 | 7.62 |

NMR (DMSO-d$_6$, δ): 0.83 (3H, t, 7 Hz), 2.67 (3H, s), 4.03 (2H, q, 7 Hz), 5.1 (2H, s), 7.03–7.67 (11H, m), 8.33–8.57 (2H, m).

Mass 458,460.

(5) Ethyl 2,4-dimethyl-6-(3-nitrophenyl)-5-pyrimidinecarboxylate hydrochloride.

mp: 153°–155° C.

IR (Nujol): 1730, 1620, 1590 cm$^{-1}$.

NMR (DMSO-d$_6$, δ): 1.06 (3H, t, J=7 Hz), 2.55 (3H, s), 2.7 (3H, s), 4.06–4.35 (2H, q, J=7 Hz), 7.76–8.1 (3H, m), 8.26–8.46 (2H, m).

(6) Ethyl 6-methyl-4-(4-hydroxy-3-nitrophenyl)-2-phenyl-5-pyrimidinecarboxylate.

mp: 97°–98° C.

IR (Nujol): 1715, 1630 cm$^{-1}$.

NMR (DMSO-d$_6$, δ): 1.13 (3H, t, J=7 Hz), 2.57 (3H, s), 4.3 (2H, q, J=7 Hz), 7.33 (1H, d, J=9 Hz), 7.3–7.8 (3H, m), 7.97 (1H, dd, J=2, 9 Hz), 8.23 (1H, d, J=2 Hz), 8.33–8.67 (2H, m).
Mass 379.

(7) Ethyl 4-(2-chlorophenyl)-6-methyl-2-phenyl-5-pyrimidinecarboxylate.
mp: 105°–106° C.

|  |  | C | H | N | Cl |
|---|---|---|---|---|---|
| Elemental Analysis | Calcd. | 68.09 | 4.86 | 7.94 | 10.05 |
|  | Found | 68.16 | 4.92 | 7.92 | 9.84 |

NMR (DMSO-d$_6$, δ): 0.86 (3H, t, 7 Hz), 2.66 (3H, s), 3.97 (2H, q, J=7 Hz), 7.2–7.5 (7H, m), 8.16–8.33 (2H, m).
Mass 353.

(8) Ethyl 6-methyl-4-(2-nitrophenyl)-2-phenyl-5-pyrimidinecarboxylate.
mp: 115°–116° C.
IR (Nujol): 1715 cm$^{-1}$.
NMR (DMSO-d$_6$, δ): 0.93 (3H, t, J=7 Hz), 2.7 (3H, s), 4.1 (2H, q, J=7 Hz), 7.47–8.0 (6H, m), 8.17–8.53 (3H, m).
Mass 363.

(9) Ethyl 4-(3,4-dimethoxyphenyl)-6-methyl-2-phenyl-5-pyrimidinecarboxylate.
mp: 85°–86° C.

|  |  | C | H | N |
|---|---|---|---|---|
| Elemental Analysis | Calcd. | 69.83 | 5.86 | 7.40 |
|  | Found | 69.91 | 5.89 | 7.38 |

IR (Nujol): 1720 cm$^{-1}$.
NMR (DMSO-d$_6$, δ): 1.14 (3H, t, J=6 Hz), 2.58 (3H, s), 3.82 (6H, s), 4.26 (2H, q, J=6 Hz), 7.03–7.65 (6H, m), 8.36–8.56 (2H, m).
Mass (M+) 378.

(10) Ethyl 4-(3-chlorophenyl)-6-methyl-2-phenyl-5-pyrimidinecarboxylate.
mp: 80°–82° C.
IR (Nujol): 1720, 1540 cm$^{-1}$.
NMR (DMSO-d$_6$, δ): 1.1 (3H, t, J=7 Hz), 2.63 (3H, s), 4.27 (2H, q, J=7 Hz), 7.4–7.83 (7H, m), 8.3–8.67 (2H, m)
Mass 352.

(11) Ethyl 4-(2-chloro-5-nitrophenyl)-6-methyl-2-phenyl-5-pyrimidinecarboxylate.
IR (Nujol): 1715, 1610, 1575, 1530 cm$^{-1}$.
NMR (DMSO-d$_6$, δ): 0.97 (3H, t, J=7 Hz), 2.78 (3H, s), 4.1 (2H, q, J=7 Hz), 7.43–7.67 (3H, m), 7.8–8.03 (1H, m), 8.3–8.6 (4H, m).
Mass 397.

(12) Ethyl 4-(3-methoxyphenyl)-6-methyl-2-phenyl-5-pyrimidinecarboxylate.
mp: 53°–55° C.
IR (Nujol): 1715, 1605, 1590, 1540 cm$^{-1}$.
NMR (DMSO-d$_6$, δ): 1.1 (3H, t, J=7 Hz), 2.67 (3H, s), 3.9 (3H, s), 4.32 (2H, q, J=7 Hz), 7.13–7.77 (7H, m), 8.4–8.7 (2H, m).
Mass 348.

(13) Ethyl 4-[2-(4-chlorobenzyloxy)-5-nitrophenyl]-2-phenyl-6-methyl-5-pyrimidinecarboxylate.
mp: 156°–158° C.
IR (Nujol): 1712, 1590, 1535 cm$^{-1}$.
NMR (DMSO-d$_6$, δ): 0.90 (3H, t, J=7 Hz), 2.70 (3H, s), 4.05 (2H, q, J=7 Hz), 5.29 (2H, s), 7.2–7.7 (8H, m), 8.2–8.5 (4H, m).

(14) Ethyl 4-[2-(4-chlorobenzyloxy)-3-nitrophenyl]-2-phenyl-6-methyl-5-pyrimidinecarboxylate.
mp: 104°–105° C.
IR (Nujol): 1730, 1600, 1260, 930 cm$^{-1}$.
NMR (DMSO-d$_6$, δ): 0.93 (3H, t, J=7 Hz), 2.73 (3H, s), 4.12 (2H, q, J=7 Hz), 4.83 (2H, s), 6.95–8.30 (10H, m), 8.4–8.7 (2H, m).

(15) Ethyl 4-[2-(4-chlorophenylthio)phenyl]-6-methyl-2-phenyl-5-pyrimidinecarboxylate.
mp: 128°–130° C.
IR (Nujol): 1728, 1540, 1258, 1078 cm$^{-1}$.
NMR (DMSO-d$_6$, δ): 0.91 (3H, t, J=7 Hz), 2.67 (3H, s), 4.07 (2H, t, J=7 Hz), $7.16 \begin{pmatrix} 4H, ABq \\ J=9Hz \end{pmatrix}$,
$7.33$ 7.4–7.6 (7H, m), 8.1–8.4 (2H, m)

(16) Ethyl 6-methyl-2-phenyl-4-(3-pyridyl)-5-pyrimidinecarboxylate.
mp: 63°–64° C.
IR (Nujol): 1725 cm$^{-1}$.
NMR (DMSO-d$_6$, δ): 1.08 (3H, t, 7 Hz), 2.73 (3H, s), 4.32 (2H, q, J=7 Hz), 7.53–7.83 (5H, m) 8.07–9.0 (4H, m).
Mass 319.

(17) Ethyl 6-methyl-2-phenyl-4-(2-pyridyl)-5-pyrimidinecarboxylate.
IR (Nujol): 1730, 1540 cm$^{-1}$.
NMR (DMSO-d$_6$, δ): 1.2 (3H, t, J=7 Hz), 2.63 (3H, s), 4.32 (2H, q, J=7 Hz), 7.46–7.66 (4H, m), 7.93–8.16 (1H, m), 8.43–8.7 (4H, m).
Mass 319.

(18) 5-Acetyl-6-methyl-2-phenyl-4-(4-pyridyl)-pyrimidine.
mp: 121°–123° C.
IR (Nujol): 1700, 1600, 1535, 1250, 775 cm$^{-1}$.
NMR (DMSO-d$_6$, δ): 2.30 (3H, s), 2.60 (3H, s), 7.4–7.8 (5H, m), 8.2–8.6 (2H, m), 8.6–8.9 (2H, m).
Mass (M+) 289.

(19) Ethyl 2-methyl-4-(4-pyridyl)-6-phenyl-5-pyrimidinecarboxylate.
mp: 77°–79° C.

|  |  | C | H | N |
|---|---|---|---|---|
| Elemental Analysis | Calcd. | 71.46 | 5.37 | 13.2 |
|  | Found | 71.82 | 5.55 | 13.2 |

IR (Nujol): 1730 cm$^{-1}$.
NMR (DMSO-d$_6$, δ): 0.87 (3H, t, J=7 Hz), 2.77 (3H, s), 4.03 (2H, q, J=7 Hz), 7.4–7.7 (7H, m), 8.6–8.8 (2H, dd, J=2, 5 Hz).

(20) 4-(3-Nitrophenyl)-2-phenyl-5-oxo-5,7-dihydrofuro[3,4-d]pyrimidine.
mp: 218°–220° C.
IR (Nujol): 1785 cm$^{-1}$.
NMR (DMSO-d$_6$): 5.53–5.7 (2H, s), 7.55–8.1 (4H, m), 8.33–8.97 (3H, m), 9.1–9.63 (1H, m).
Mass 333.

(21) 2-Phenyl-4-(4-pyridiyl)-5-oxo-5,7-dyhydrofuro[3,4-d]pyrimidine.
mp: 191°–192° C.

NMR (DMSO-d$_6$, δ): 5.53 (2H, s), 7.43–7.73 (3H, m), 8.07–8.33 (2H, m), 8.4–8.93 (4H, m).
Mass 289.

(22) Ethyl 4-[2-(4-chlorobenzyloxy)phenyl-2,6-dimethyl-5-pyrimidinecarboxylate].
mp: 103°–105° C.

|  |  | C | H | N |
|---|---|---|---|---|
| Elemental Analysis | Calcd. | 66.58 | 5.33 | 7.06 |
|  | Found | 66.70 | 5.81 | 6.92 |

IR (Nujol): 1715 cm$^{-1}$.
NMR (DMSO-d$_6$, δ): 0.83 (3H, t, J=7 Hz), 2.53 (3H, s), 2.65 (3H, s), 4.0 (2H, q, J=7 Hz), 5.1 (2H, s), 6.96–7.6 (8H, m).
Mass 396, 398.

(23) Ethyl 2,6-dimethyl-4-(3-pyridyl)-5-pyrimidinecarboxylate dihydrochloride.
mp: 166°–170° C.
IR (Nujol): 1720, 1595, 863 cm$^{-1}$.
NMR (DMSO-d$_6$, δ): 1.07 (3H, t, J=7 Hz), 2.63 (3H, s), 2.73 (3H, s), 4.23 (2H, q, J=7 Hz), 7.97–8.26 (1H, m), 8.46–8.7 (1H, m), 8.9–9.2 (2H, m)
Mass 330.

(24) Ethyl 2,6-dimethyl-4-(4-pyridyl)-5-pyrimidinecarboxylate dihydrochloride.
mp: 198°–199° C.
IR (Nujol): 1730, 1620, 1275, 1010 cm$^{-1}$.
NMR (DMSO-d$_6$, δ): 1.03 (3H, t, J=7 Hz), 2.06 (3H, s), 2.70 (3H, s), 4.20 (2H, q, J=7 Hz), 8.0–8.20 (2H, m), 8.7–8.9 (2H, m).

(25) Iso-propyl 6-methyl-4-(3-nitrophenyl)-2-phenyl-5-pyrimidinecarboxylate.
IR (Nujol): 1715, 1590, 1353 cm$^{-1}$.
NMR (DMSO-d$_6$, δ): 1.17 (6H, d, J32 7 Hz), 2.67 (3H, s), 5.10 (1H, m), 7.3–8.7 (9H, m)
Mass (M+) 377.

(26) Methyl 6-methyl-4-(3-nitrophenyl)-2-phenyl-5-pyrimidinecarboxylate.
mp: 128°–130° C.
IR (Nujol): 1725, 1590, 1270 cm$^{-1}$.
NMR (DMSO-d$_6$, δ): 2.63 (3H, s), 3.77 (3H, s), 7.4–8.7 (9H, m).
Mass (M+) 349.

(27) 5-Acetyl-6-methyl-4-(4-nitrophenyl)-2-phenylpyrimidine.
mp: 138°–140° C.
IR (Nujol): 1695, 1608, 1350 cm$^{-1}$.
NMR (DMSO-d$_6$, δ): 2.27 (3H, s), 2.60 (3H, s), 7.4–7.7 (3H, m), 7.93 (2H, dd, J=9 Hz, 2 Hz), 8.38 (2H, dd, J=9 Hz, 2 Hz), 8.3–8.6 (2H, m).
Mass (M+) 333.

(28) Ethyl 4-(3-methoxy-5-nitro-4-hydroxyphenyl)-6-methyl-2-phenyl-5-pyrimidinecarboxylate.
mp: 159°–161° C.
IR (Nujol): 1725, 1625, 1555, 1525 cm$^{-1}$.
NMR (DMSO-d$_6$, δ): 1.15 (3H, t, J=7 Hz), 2.58 (3H, s), 3.92 (3H, s), 4.28 (2H, q, J=7 Hz), 7.23–7.93 (5H, m), 8.33–8.52 (2H, m)
Mass 409.

(29) Ethyl 4-(3-cyanophenyl)-6-methyl-2-phenyl-5-pyrimidinecarboxylate.
mp: 88°–90° C. IR (Nujol): 1725, 1540, 1270 cm$^{-1}$.
NMR (DMSO-d$_6$, δ): 1.07 (3H, t, J=7 Hz), 2.63 (3H, s), 4.22 (2H, q, J=7 Hz), 7.33–7.7. (3H, m), 7.7–8.2 (4H, m), 8.27–8.6 (2H, m)
Mass 343.

(30) Ethyl 4-(4-cyanophenyl)-6-methyl-2-phenyl-5-pyrimidinecarboxylate.
mp: 86°–87° C.
IR (Nujol): 2250, 1715 cm$^{-1}$.
NMR (DMSO-d$_6$, δ): 1.07 (3H, t, J=7 Hz), 2.67 (3H, s), 4.23 (2H, q, J=7 Hz), 7.4–7.73 (3H, m), 7.73–8.23 (4H, m), 8.33–8.67 (2H, m).

(31) Ethyl 4-(4-chloro-3-nitrophenyl)-6-methyl-2-phenyl-5-pyrimidinecarboxylate.
mp: 81°–82° C.
IR (Nujol): 1720, 1605, 1575, 1530 cm$^{-1}$.
NMR (DMSO-d$_6$, δ): 1.12 (3H, t, J=7 Hz), 2.67 (3H, s), 4.33 (2H, q, J=7 Hz). 7.5–7.77 (3H, m), 7.97–8.13 (2H, m), 8.4–8.7 (3H, m)
Mass 397.

(32) 5-Hydroxymethyl-6-methyl-2-phenyl-4-(4-pyridyl)pyrimidine.
mp: 175°–176° C.
IR (Nujol): 3200, 1610, 1550, 1030, 1005, 820, 735, 690 cm$^{-1}$.

(33) 5,6-Dimethyl-2-phenyl-4-(4-pyridyl)pyrimidine.
mp: 152°–153° C.
IR (Nujol): 1540, 840, 763, 695 cm$^{-1}$.

(34) 6-Methyl-2-phenyl-4-(4-pyridyl)-5-pyrimidinecarboxylic acid.
mp: 270°–271° C.
IR (Nujol): 1710, 1615, 1535, 1025, 765 cm$^{-1}$.

(35) 5-tert-Butyloxycarbonylamino-6-methyl-2-phenyl-4-(4-pyridyl)pyrimidine.
mp: 166°–167° C.
IR (Nujol): 3210, 1690, 1605, 1162, 1055, 1030, 768, 700 cm$^{-1}$.

(36) 5-Amino-6-methyl-2-phenyl-4-(4-pyridyl)pyrimidine.
mp: 208°–209° C.
IR (Nujol): 1635, 1545, 1225, 765, 703 cm$^{-1}$.

(37) Ethyl 4-(4-acetoxy-5-nitrophenyl)-6-methyl-2-phenyl-5-pyrimidinecarboxylate.
mp: 147°–148° C.
IR (Nujol): 1780, 1725, 1620, 1585, 1535 cm$^{-1}$.

(38) Ethyl 6-methyl-4-(2-methylthio-5-nitrophenyl)-2-phenyl-5-pyrimidinecarboxylate.
mp: 125°–126° C.
IR (Nujol): 1730, 1605, 1580, 1520 cm$^{-1}$.

(39) Ethyl 6-methyl-4-(2-methylsulfinyl-5-nitrophenyl)-2-phenyl-5-pyrimidinecarboxylate.
mp: 130°–132° C.
IR (Nujol): 1725, 1530 cm$^{-1}$.

(40) 2-Hydroxyethyl 6-methyl-4-(3-nitrophenyl)-2-phenyl-5-pyrimidinecarboxylate.
mp: 84°–86° C.
IR (Nujol): 1705, 1530 cm$^{-1}$.

(41) Ethyl 4-(4-methoxycarbonylphenyl)-6-methyl-2-phenyl-5-pyrimidinecarboxylate.
mp: 126°–127° C.
IR (Nujol): 1715, 1530 cm$^{-1}$.
NMR (DMSO-d$_6$, δ): 1.07 (3H, t, J=7 Hz), 2.65 (3H, s), 3.9 (3H, s), 4.23 (2H, q, J=7 Hz), 7.37–8.23 (7H, m), 8.23–8.57 (2H, m).
Mass 376.

(42) 5-[3-(2-dimethylaminoethyl)ureido]-6-methyl-4-(3-nitrophenyl)-2-phenylpyrimidine hydrochloride.
mp: 83°–84° C.
IR (Nujol): 1700, 1620, 1600, 740 cm$^{-1}$.

(43) 5-(1-Hydroxyethyl)-6-methyl-4-(4-nitrophenyl)-2-phenylpyrimidine.
mp: 146°–148° C.
IR (Nujol): 1608, 1550, 1353, 700 cm$^{-1}$.

(44) 6-Methyl-4-(3-nitrophenyl)-2-phenyl-5-pyrimidinecarboxylic acid.
mp: 208°–209° C.
IR (Nujol): 1715, 1590, 1360 cm$^{-1}$.

(45) 5-tert-Butyloxycarbonylamino-6-methyl-4-(3-nitrophenyl)-2-phenylpyrimidine.
mp: 187°–189° C.
IR (Nujol): 3350, 1695, 1530, 1160 cm$^{-1}$.

(46) 5-Amino-6-methyl-4-(3-nitrophenyl)-2-phenylpyrimidine.
mp: 179°–181° C.
IR (Nujol): 1630, 1538, 1350 cm$^{-1}$.

(47) 5-Acetyl-6-methyl-4-(4-chloro-3-nitrophenyl)-2-phenyl-pyrimidine.

(48) 5-(2-Dimethylaminoethylcarbamoyl)-6-methyl-2-phenyl-4-(3-nitrophenyl)pyrimidine.
mp: 122°–124° C.
IR (Nujol): 1630, 1565, 1530 cm$^{-1}$.
Mass (M/Z): 405 (M+).
NMR (CDCl$_3$, δ): 2.01 (6H, s), 2.26 (2H, t, J=6 Hz), 2.71 (3H, s), 3.38 (2H, t, d, J=6 Hz, 6Hz), 6.35 (1H, t, J=6 Hz), 7.38–7.73 (4H, m), 8.13–8.60 (4H, m), 8.75–8.83 (1H, m).

EXAMPLE 4

To a suspension of lithium aluminum hydride (0.24 g) in dry tetrahydrofuran (40 ml) was dropwise added a solution of ethyl 6-methyl-2-phenyl-4-(4-pyridyl)-5-pyrimidinecarboxylate (2.0 g) in the same solvent (20 ml) under cooling at 7°–9° C. After the addition was completed, the mixture was stirred for 2 hours at room temperature. The excess lithium aluminum hydride was decomposed by a careful addition of water and the dried solution was concentrated in vacuo to an oil. The oil was column chromatographed on silica gel eluting with chloroform and the fractions containing a produce were collected and concentrated in vacuo. The residual crystals were recrystallized from n-hexane to give 5,6-dimethyl-2-phenyl-4-(4-pyridyl)pyrimidine (0.03 g), mp 152°–153° C.
IR (Nujol): 1540, 840, 763, 695 cm$^{-1}$
NMR (DMSO-d$_6$, δ): 2.29 (3H, s), 2.62 (3H, s), 7.4–7.6 (3H, m), 7.55–7.75 (2H, m), 8.2–8.5 (2H, m), 8.65–8.9 (2H, m)
Mass (M+) 261.

The fractions eluted further with a mixture of chloroform and Methanol (50:1) was combined and concentrated in vacuo. The residue was recrystallized from ethyl ether to afford 5-hydroxymethyl-6-methyl-2-phenyl-4-(4-pyridyl)pyrimidine (0.28 g), mp 175°–176° C.
IR (Nujol): 3200, 1610, 1550, 1030, 1005, 820, 735, 690 cm$^{-1}$.
NMR (DMSO-d$_6$, δ): 2.73 (3H, s), 4.50 (2H, d, J=5 Hz), 5.45 (1H, t, J=5 Hz), 7.4–7.6 (3H, m), 7.7–7.9 (2H, m), 8.3–8.6 (2H, m), 8.7–8.9 (2H, m).
Mass (M+) 277.

EXAMPLE 5

A solution of ethyl 6-methyl-2-phenyl-4-(4-pyridyl)-5-pyrimidinecarboxylate (15 g) and aqueous potassium hydroxide (3.48 g, in 30 ml H$_2$O) in ethanol (150 ml) was refluxed for 4.5 hours. After evaporating the solvent, the residue was dissolved in a suspension of water (150 ml) and chloroform (150 ml) under stirring. The separated aqueous layer was adjusted to pH 5.5 with 10% aqueous hydrochloride. The resulting precipitate was collected by filtration, washed with water and dried in vacuo to give 6-methyl-2-phenyl-4-(4-pyridyl)-5-pyrimidinecarboxylic acid (12.3 g).
mp 270°–271° C.
IR (Nujol): 1710, 1615, 1535, 1025, 765 cm$^{-1}$.
NMR (CF$_3$cooD δ): 3.33 (3H, s), 7.6–8.1 (3H, m), 8.3–8.8 (4H, m), 9.0–9.4 (2H, m)
Mass (M+) 291.

EXAMPLE 6

The following compound was prepared according to the similar manner to that of Example 5.
6-Methyl-4-(3-nitrophenyl)-2-phenyl-5-pyridimidinecarboxylic acid.
mp: 208°–209° C.
IR (Nujol): 1715, 1590, 1360 cm$^{-1}$.
NMR (CF$_3$COOH, δ): 3.22 (3H, s), 7.6–9.2 (9H, m).
Mass (M+) 335.

EXAMPLE 7

A mixture of 6-methyl-2-phenyl-4-(4-pyridyl)-5-pyrimidinecarboxylic acid (5 g), triethylamine (1.75 g) and diphenylphosphorylazide (4.7 g) intbutanol (50 ml) was refluxed for 7 hours. After removal of the solvent, by evaporation the residue was dissolved in a suspension of ethylacetate (100 ml) and water (100 ml) under stirring. The separated organic layer was washed with 10% aqueous hydrochloric acid, saturated aqueous sodium bicarbonate, and saturated aqueous sodium chloride successively, and dried over magnesium sulfate. The solvent was evaporated in vacuo, and the residual substance was recrystallized from ether to give 5-tert-Butyloxycarbonylamino-6-methyl-2-phenyl-4-(4-pyridyl)pyrimidine, mp 166°–167° C.
IR (Nujol): 3210, 1690, 1605, 1162, 1055, 1030, 768, 700 cm$^{-1}$.
NMR (DMSO-d$_6$, δ): 1.33 (9H, s), 2.57 (3H, s), 7.4–7.6 (3H, m), 7.6–7.9 (2H, m), 8.2–8.55 (2H, m), 8.6–8.85 (2H, m), 9.05 (1H, br).
Mass (M+) 362.

EXAMPLE 8

The following compound was prepared according to the similar manner to that of Example 7.
5-tert-Butyloxycarbonylamino-6-methyl-4-(3-nitrophenyl)-2-phenylpyrimidine.
mp: 187°–189° C.
IR (Nujol): 3350, 1695, 1530, 1160 cm$^{-1}$.
NMR (DMSO-d$_6$, δ): 1.30 (9H, s), 2.59 (3H, s), 7.3–7.65 (3H, s), 7.7–8.0 (1H, m), 8.2–8.7 (5H, m), 9.10 (1H, br)
Mass (M+1) 407.

EXAMPLE 9

A mixture of 5-tert-butyloxycarbonylamino-6-methyl-2-phenyl-4-(4-pyridyl)pyrimidine (1.5 g) and an isopropanol solution of hydrogen chloride (4 ml, HCl 5 mMol/ml) in ethanol (15 ml) was stirred for 1 hour at 40° C. After cooling to room temperature, the reaction mixture was poured into a suspension of ethyl acetate (100 ml) and water (50 ml) under stirring, and the mixture was adjusted to pH 9.0. The separated organic layer was washed with saturated aqueous sodium chloride and dried over magnesium sulfate. The solvent was evaporated in vacuo, and the residual crystal was recrystallized from ether to give 5-amino-6-methyl-2-phenyl-4-(4-pyridyl)pyrimidine, mp 208°–209° C.
IR (Nujol): 1635, 1545, 1225, 765, 703 cm$^{-1}$.

NMR (DMSO-d$_6$, δ): 2.53 (3H, s), 5.41 (2H, s), 7.3–7.6 (3H, m), 7.7–7.9 (2H, m), 8.2–8.4 (2H, m), 8.6–8.9 (2H, m).
Mass (M+) 262.

EXAMPLE 10

The following compound was prepared according to the similar manner to that of Example 9.
5-Amino-6-methyl-4-(3-nitrophenyl)-2-phenylpyrimidine.
mp: 179°–181° C.
IR (Nujol): 1630, 1538, 1350 cm$^{-1}$.
NMR (DMSO-d$_6$, δ): 2.54 (3H, s), 5.43 (2H, s), 7.3–7.6 (3H, s), 7.65–7.95 (1H, m), 8.1–8.4 (4H, m), 8.62 (1H, m)
Mass (M+) 306.

EXAMPLE 11

A mixture of 1.5 g of ethyl 4-(4-hydroxy-5-nitrophenyl)-6-methyl-2-phenyl-5-pyrimidinecarboxylate and 7.5 ml of acetic anhydride in 7 ml of tetrahydrofuran was stirred for 5 hours. The reaction mixture was evaporated in vacuo. The residue was chromatographed on silica gel eluting with a mixture of n-hexane and ethyl acetate (10:1). The fractions containing the desired product were combined and concentrated in vacuo. The crystalline residue was recrystallized from diethyl ether to give ethyl 4-(4-acetoxy-5-nitrophenyl)-6-methyl-2-phenyl-5-pyrimidinecarboxylate (0.23 g).
mp 147°–148° C.
IR (Nujol): 1780, 1725, 1620, 1585, 1535 cm$^{-1}$.
NMR (DMSO-d$_6$, δ): 1.1 (3H, t, J=7 Hz), 2.37 (3H, s), 2.67 (3H, s), 4.26 (2H, q, J=7 Hz), 7.46–7.73 (4H, m), 8.03–8.2 (1H, m), 8.33–8.53 (3H, m).
Mass 421.

EXAMPLE 12

To a solution of tetrahydrofuran (25 ml), methylmercaptan-diemthylformamide solution (methylmercaptan 66 g/DMF 306 g) (5 ml) and ethyl 4-(2-chloro-5-nitrophenyl)-6-methyl-2-phenyl-5-pyrimidinecarboxylate (2 g), sodium methylmercaptan (0.42 g) was added, stirred for 3 h at ambient temperature. The reaction mixture was evaporated in vacuo and the residue was dissolved in a mixture of water (50 ml) and ethyl acetate (100 ml). The organic layer was washed with a saturated aqueous solution of sodium chloride and dried over magnesium sulfate. The solvent was distilled off. The residue was chromatographed on silica gel, eluting with a mixture of n-hexane and ethyl acetate (10:1). The fractions containing the object compound were combined and concentrated in vacuo. The crystalline residue was recrystallized from diethyl ether to afford ethyl 6-methyl-4-(2-methylthio-5-nitrophenyl)-2-phenyl-5-pyrimidinecarboxylate (0.4 g).
mp 125°–126° C.
IR (Nujol): 1730, 1605, 1580, 1520 cm$^{-1}$.
NMR (DMSO-d$_6$, δ): 1.27 (3H, t, J=7 Hz), 2.53 (3H, s), 2.73 (3H, s), 4.12 (2H, q, J=7 Hz), 7.43–7.8 (4H, m), 8.07–8.6 (4H, m).
Mass 409.

EXAMPLE 13

To a mixture of ethyl 6-methyl-4-(2-methylthio-5-nitrophenyl)-2-phenyl-5-pyrimidinecarboxylate (2 g) and chloroform (10 ml), 3-chloroperoxybenzoic acid (1.26 g) in a mixture of chlorofrom (3 ml) and acetone (1 ml) was dropwise added at 4°–6° with stirring, which was continued under the same condition for 45 minutes. The reaction mixture was extracted with chloroform (100 ml), washed with aqueous solution of sodium iodide, sodium hydrogen sulfite, sodium hydrogen carbonate, and sodium chloride and dried over magnesium sulfate. The solvent was distilled off. The residue was chromatographed on silica gel, eluting with a mixture of n-hexane and ethyl acetate (10:1). The fractions containing the object compound were combined and concentrated in vacuo. The crystalline residue was recrystallized from isopropyl ether to afford ethyl 6-methyl-4-(2-methylsulfinyl-5-nitrophenyl)-2-phenyl-5-pyrimidine carboxylate (1.3 g).
mp 130°–132° C.
IR (Nujol): 1725, 1530 cm$^{-1}$.
NMR (DMSO-d$_6$, δ): 0.88 (3H, t, J=7 Hz), 2.68 (3H, s), 2.77 (3H, s), 4.08 (2H, q, J=7 Hz), 7.33–7.7 (3H, m), 8.17–8.77 (5H, m)
Mass 425.

EXAMPLE 14

A mixture of ethyl 6-methyl-4-(3-nitrophenyl)-2-phenyl-5-pyrimidinecarboxylate (2 g) and ethyleneglycol (8 ml) was stirred for 50 hours at 90°. The reaction mixture was poured into a mixture of water (50 ml), ethyl acetate (50 ml) and tetrahydrofuran (50 ml). The solvent was distilled off. The residue was chromatographed on silica gel, eluting with a mixture of n-hexane and ethyl acetate (10:1). The fractions containing the object compound were combined and concentrated in vacuo. The crystalline residue was recrystallized from diethyl ether to afford 2-hydroxyethyl 6-methyl-4-(3-nitrophenyl)-2-phenyl-5-pyrimidinecarboxylate.
mp 84°–86° C.
IR (Nujol): 1705, 1530 cm$^{-1}$.
NMR (DMSO-d$_6$, δ): 2.72 (3H, s), 3.58 (2H, t, J=5 Hz), 4.27 (2H, t, J=5 Hz), 4.8 (1H, t, J=5 Hz), 7.43–8.6 (9H, m).
Mass 379.

EXAMPLE 15

The following compounds were prepared according to the similar manners to that of Example 14.
(1) Ethyl 6-methyl-4-(3-nitrophenyl)-2-phenyl-5-pyrimidinecarboxylate.
mp: 97°–98° C.
IR (Nujol): 1720 cm$^{-1}$.
(2) Methyl 6-methyl-4-(3-nitrophenyl)-2-phenyl-5-pyrimidinecarboxylate.
mp: 128°–130° C.
IR (Nujol): 1725, 1590, 1270 cm$^{-1}$.
(3) Isopropyl 6-methyl-4-(3-nitrophenyl)-2-phenyl-5-pyrimidinecarboxylate.
IR (Nujol): 1715, 1590, 1353 cm$^{-1}$.

EXAMPLE 16

The mixture of 6-methyl-4-(3-nitrophenyl)-2-phenyl-5-pyrimidinecarboxylic acid (5 g), triethylamine (1.5 g) and diphenylphosphoyrylazide (4.1 g) in benzene was refluxed for 2 hours and 2-dimethylaminoethylamine (1.6 g) was added. After continuing the reflux for 2 hours, the reaction mixture was poured into a mixture of Diethylether (100 ml) and saturated sodium hydrogen carbonate (50 ml). The separated organic layer was dried over magnesium sulfate and evaporated in vacuo. The residual substance was column-chromatographed on alumina. The eluted active fraction with chloroform was concentrated in vacuo and added 0.1 mole hydrochloric acid in isopropyl ether. The resulted crystalline was collected and washed with diethyl ether, dried to give 5-[3-(2-dimethylaminoethyl)ureido]-6-methyl-4-(3-nitrophenyl)-2-phenylpyrimidine hydrochloride (0.98 g).

mp 83°–84° C.

IR (Nujol): 1700, 1620, 1600, 740 cm$^{-1}$.

NMR (DMSO-d$_6$, δ): 2.57 (3H, s), 2.67 (3H, s), 2.72 (3H, s), 2.8–3.2 (2H, m), 3.15–3.50 (2H, m), 7.0 (1H, br), 7.3–7.6 (3H, m), 7.65–7.95 (1H, m), 8.1–8.5 (4H, m), 10.65 (1H, br).

EXAMPLE 17

The mixture of 5-acetyl-6-methyl-4-(4-nitrophenyl)-2-phenyl-pyrimidine (1.5 g) and sodium borohydride (170 mg) in methanol (15 ml) and tetrahydrofuran (20 ml) was stirred for 2 hours at 5°–7° C. with ice cooling. The mixture was extracted with chloroform (100 ml) and 10% aqueous hydrochloric acid (50 ml). The separated organic layer was washed successively with saturated sodium hydrogen carbonate, saturated aqueous sodium chloride, dried over magnesium sulfate and evaporated in vacuo. The residue is recrystallized from ether to give 5-(1-hydroxyethyl)-6-methyl-4-(4-nitrophenyl)-2-phenylpyrimidine (0.3 g).

mp 146°–148° C.

IR (Nujol): 1608, 1550, 1353, 700 cm$^{-1}$.

NMR (DMSO-d$_6$, δ): 1.45 (3H, d, J=7 Hz), 2.86 (3H, s), 4.90 (1H, m), 5.41 (1H, d, J=2 Hz), 7.3–7.6 (3H, m), 7.83 (2H, dd, J=9 Hz, 2 Hz), 8.37 (2H, dd, J=9 Hz, 2 Hz), 8.2–8.5 (2H, m).

Mass (M+) 335.

EXAMPLE 18

To a solution of ethyl 1,6-dihydro-4-methyl-2-phenyl-6-(3-trifluoromethylphenyl)-5-pyrimidinecarboxylate (12 g) in ethyl acetate (240 ml) was added activated manganese dioxide (48 g) and the mixture was refluxed for 2.5 hours with stirring vigorously. After allowing to cool, manganese dioxide was filtered off. The filtrate was evaporated in vacuo and the residual precipitate was recrystallized from pet ether. The crystal was filtered off and dried in vacuo to give ethyl 6-methyl-2-phenyl-4-(3-trifluoromethylphenyl)-5-pyrimidinecarboxylate (0.45 g).

mp: 59°–60° C.

IR (Nujol): 1735, 1550 cm$^{-1}$.

NMR (DMSO-d$_6$, δ): 1.05 (3H, t, J=7 Hz), 2.65 (3H, s), 4.22 (2H, q, J=7 Hz), 7.33–7.67 (3H, m), 7.7–8.1 (4H, m), 8.3–8.6 (2H, m).

Mass: 386.

EXAMPLE 19

The following compounds were prepared according to the similar manners to that of Example 1, 2 or 18.

(1) 6-Methyl-4-(3-nitrophenyl)-2-phenyl-5-pyrimidinecarboxamide.

mp: 231–232° C.

IR (Nujol): 3325, 1665 cm$^{-1}$.

NMR (DMSO-d$_6$, δ): 2.67 (3H, s), 7.3–8.8 (11H, m).

Mass: 334 (M+).

(2) Ethyl 6-methyl-4-(3-nitrophenyl)-2-(3-pyridyl)-5-pyrimidinecarboxylate.

mp: 63°–64° C.

IR (Nujol): 1735, 1585, 1535 cm$^{-1}$.

NMR (DMSO-d$_6$, δ): 1.1 (3H, t, J=7 Hz), 2.66 (3H, s), 4.26 (2H, q, J=7 Hz), 7.53–8.9 (7H, m), 9.62 (1H, m).

Mass: 364.

(3) 5-Acetyl-4-(4-hydroxy-3-nitrophenyl)-6-methyl-2-phenylpyrimidine.

mp: 154°–155° C.

IR (Nujol): 1695, 1625, 1580 cm$^{-1}$.

NMR (DMSO-d$_6$, δ): 2.27 (3H, s), 2.52 (3H, s), 7.23 (1H, d, J=8 Hz), 7.33–7.63 (3H, m), 7.78 (1H, dd, J=2, 8 Hz), 8.15 (1H, d, J=2 Hz), 8.3–8.5 (2H, m).

Mass: 349.

(4) Ethyl 4-(3-hydroxy-4-nitrophenyl)-6-methyl-2-phenyl-5-pyrimidinecarboxylate.

mp: 109° C.

IR (Nujol): 1723, 1630, 1590, 1382 cm$^{-1}$.

NMR (DMSO-d$_6$, δ): 1.12 (3H, t, J=7 Hz), 2.7 (3H, s), 4.28 (2H, q, J=7 Hz), 7.23 (1H, dd, J=2, 8 Hz), 7.42–7.73 (4H, m), 8.03 (1H, d, J=8 Hz), 8.37–8.63 (2H, m).

Mass: 379.

(5) 5-Acetyl-4-(4-chloro-3-nitrophenyl)-6-methyl-2-phenyl-pyrimidine.

mp: 139°–140° C.

IR (Nujol): 1700, 1605, 1570, 1535, 1240 cm$^{-1}$.

NMR (DMSO-d$_6$, δ): 2.33 (3H, s), 2.6 (3H, s), 7.43–7.67 (3H, m), 7.87–8.0 (2H, m), 8.33–8.57 (3H, m)

Mass: 367, 369.

(6) N-(2-Dimethylaminoethyl)-6-methyl-4-(3-nitrophenyl)-2-phenyl-5-pyrimidinecarboxamide.

mp: 122°–124° C.

IR (Nujol): 1630, 1565, 1530 cm$^{-1}$.

(7) N-(2-Diethylaminoethyl)-6-methyl-4-(3-nitrophenyl)-2-phenyl-5-pyrimidinecarboxamide.

mp: 109°–111° C.

IR (Nujol): 3200, 1625, 1530 cm$^{-1}$.

(8) N-(3-Dimethylaminopropyl)-6-methyl-4-(3-nitrophenyl)-2-phenyl-5-pyrimidinecarboxamide.

mp: 137°–139° C.

IR (Nujol): 1630, 1565, 1530 cm$^{-1}$.

(9) N-[2-(1-Pyrrolidinyl)ethyl]-6-methyl-4-(3-nitrophenyl)-2-phenyl-5-pyrimidinecarboxamide mp: 133° C.

IR (Nujol): 1630, 1565, 1530 cm$^{-1}$.

(10) N-[(1-Ethyl-2-pyrrolidinyl)methyl]-6-methyl-4-(3-nitrophenyl)-2-phenyl-5-pyrimidinecarboxamide mp: 88°–90° C.

IR (Nujol): 1630, 1565, 1530 cm$^{-1}$.

(11) N-(2-Dimethylaminoethyl)-6-methyl-4-(4-nitrophenyl)-2-phenyl-5-pyrimidinecarboxamide.

mp: 148°–149° C.

IR (Nujol): 3260, 1640 cm$^{-1}$.

(12) 6-Methyl-4-(4-nitrophenyl)-2-phenyl-5-pyrimidinecarboxylic acid.

mp: 247°–248° C. (dec.).

IR (Nujol): 1690, 1608, 1355 cm$^{-1}$.

(13) Ethyl 6-methyl-4-(2-methylsulfonyl-5-nitrophenyl)-2-phenyl-5-pyrimidinecarboxylate.

mp: 150°–151° C.

IR (Nujol): 1730, 1535, 1155 cm$^{-1}$.

(14) 6-Methyl-4-(3-nitrophenyl)-2-phenyl-5-pyrimidinecarbonitrile.

mp: 185°–187° C.

IR (Nujol): 2230, 1525, 1350 cm$^{-1}$.

(15) N-(2-Dimethylaminoethyl)-6-methyl-4-(3-nitrophenyl)-2-phenyl-5-pyrimidinecarboxamide fumarate.

mp: 200°–201° C.

IR (KBr): 1640, 1530 cm$^{-1}$.

(16) Ethyl 6-methyl-4-[2-(4-nitrobenzyloxy)phenyl]-2-phenyl-5-pyrimidinecarboxylate.
mp: 113°–114° C.
IR (Nujol): 1732, 1601, 1540, 1520.
NMR (DMSO-$d_6$, δ): 0.88 (3H, t, J=7 Hz), 2.7 (3H, s), 4.03 (2H, q, J=7 Hz), 5.25 (2H, s), 6.93–7.65 (9H, m), 7.9–8.55 (4H, m).
Mass: 469.

(17) 6-Methyl-4-(3-nitrophenyl)-N-[2-(1morpholino)ethyl]-2-phenyl-5-pyrimidinecarboxamide.
mp: 165°–167° C.
IR (Nujol): 3400, 1625, 1565, 1530, 1350 cm$^{-1}$.

(18) N-(2-Acetylaminoethyl)-6-methyl-4-(3-nitrophenyl)-2-phenyl-5-pyrimidinecarboxamide.
mp: 199°–201° C.
IR (Nujol): 3300, 1640, 1590, 1540 cm$^{-1}$.

(19) 6-Methyl-5-(4-methylpiperazin-1-ylcarbonyl)-4-(3-nitrophenyl)-2-phenylpyrimideine.
mp: 153°–155° C.
IR (Nujol): 1634, 1530, 1345 cm$^{-1}$.

(20) 6-Methyl-5-(4-methylpiperazin-1-ylcarbonyl)-4-(3-nitrophenyl)-2-phenylpyrimidine fumarate.
mp: 245°–246° C.
IR (Nujol): 1715, 1645, 1530 cm$^{-1}$.

(21) N-[3-(1-Ethyl)piperidinyl]-6-methyl-4-(3-nitrophenyl)-2-phenyl-5-pyrimidinecarboxamide.
mp: 146°–148° C.
IR (Nujol): 3290, 1635, 1525, 1350 cm$^{-1}$.

(22) N-(2-Trimethylammonioethyl)-6-methyl-4-(3-nitrophenyl)-2-phenyl-5-pyrimidinecarboxamide iodide.
mp: 228°–230° C.
IR (Nujol): 3390, 1670, 1585, 1525, 1350 cm$^{-1}$.

(23) 5-[3-(1-Ethylpiperidin-3-yl)ureido]-6-methyl-4-(3-nitrophenyl)-2-phenylpyrimidine.
mp: 206°–208° C.
IR (Nujol): 1625, 1575, 1530, 1352 cm$^{-1}$.

(24) 6-Methyl-5-[(4-methylpiperazin-1-yl)carbonylamino]-4-(3-nitrophenyl)-2-phenylpyrimidine.
mp: 221°–223° C.
IR (Nujol): 3300, 1630, 1555, 1530, 1350 cm$^{-1}$.

(25) N-(2-Hydroxyethyl)-6-(3-nitrophenyl)-2-phenyl-5-pyrimidinecarboxaminde.
mp: 190°–192° C.
IR (Nujol): 3300, 1630, 1550, 1520, 1355 cm$^{-1}$.
NMR (DMSO-$d_6$, δ): 2.65 (3H, s), 3.3–3.5 (4H, m), 4.5–4.75 (1H, m), 7.50–8.0 (4H, m), 8.3–8.85 (6H, m).

(26) N-(2-Chloroethyl)-6-methyl-4-(3-nitrophenyl)-2-phenyl-5-pyrimidinecarboxamide.
mp: 199°–200° C.
IR (Nujol): 3300, 1640, 1590, 1530 cm$^{-1}$.

(27) 6-Methyl-4-(3-nitrophenyl)-2-phenyl-N-[2-(4-thiomorpholino)ethyl]-5-pyrimidinecarboxamide.
mp: 168°–169° C.
IR (Nujol): 3210, 1620, 1565, 1530, 1350 cm$^{-1}$.

(28) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.

(29) 5-Hydroxymethyl-6-methyl-2-phenyl-4-(3-nitrophenyl)pyrimidine.
mp: 177°–178° C.
IR (Nujol): 1590, 1360, 1025 cm$^{-1}$.

(30) 5-Bromomethyl-6-methyl-2-phenyl-4-(3-nitrophenyl)pyrimidine.
mp: 163°–164° C.
IR (Nujol): 1550, 1530, 1350 cm$^{-1}$.

(31) 5-Cyanomethyl-6-methyl-2-phenyl-4-(3-nitrophenyl)pyrimidine.
mp: 219°–221° C.
IR (Nujol): 1535, 1350 cm$^{-1}$.

(32) Ethyl 6-methyl-4-(3-nitrophenyl)-2-phenyl-5-pyrimidinylacetate.
mp: 106°–108° C.
IR (Nujol): 1733, 1535 cm$^{-1}$.

(33) 6-Methyl-4-(3-nitrophenyl)-2-phenyl-5-pyrimidinylacetic acid.
mp: 222°–224° C. (dec.).
IR (Nujol): 1700, 1530 cm$^{-1}$.

(34) N-(2-Dimethylaminoethyl)-[6-methyl-4-(3-nitrophenyl)-2-phenyl-5-pyrimidinyl]acetoamide
mp: 185°–187° C.
IR (Nujol): 3300, 1650, 1530 cm$^{-1}$.

(35) Methyl 6-ethyl-4-(3-nitrophenyl)-2-phenyl-5-pyrimidinecarboxylate.
mp: 107°–110° C.
IR (Nujol): 2950, 1725, 1541 cm$^{-1}$.
NMR (DMSO-$d_6$, δ): 1.41 (3H, t, J=7 Hz), 2.97 (2H, q, J=7 Hz), 3.83 (3H, s), 7.43–7.80 (3H, m), 7.80–8.66 (6H, m).
Mass: 363.

(36) 6-Ethyl-4-(3-nitrophenyl)-2-phenyl-5-pyrimidinecarboxylic acid.
mp: 184°–185° C.
IR (Nujol): 1720, 1540, 1350 cm$^{-1}$.

(37) N-(2-Dimethylaminoethyl)-6-ethyl-4-(3-nitrophenyl)-2-phenyl-5-pyrimidinecarboxamide.
mp: 106°–109° C.
IR (Nujol): 3200, 1630, 1530, 1350.

(38) 4-(3-Nitrophenyl)-2-phenyl-6-trifluoromethyl-5-pyrimidinecarboxylic acid.
mp: 313°–315° C. (dec.).
IR (Nujol): 1615, 1530 cm$^{-1}$.

(39) N-(2-Dimethylaminoethyl)-4-(3-nitrophenyl)-2-phenyl-6-trifluoromethyl-5-pyrimidinecarboxyamide.
mp: 174°–175° C.
IR (Nujol): 3300, 1645, 1575, 1541, 1540, 1355 cm$^{-1}$.

(40) Methyl 6-methyl-4-[2-(4-methylpiperazin-1-yl)-5-nitrophenyl]-2-phenyl-5-pyrimidinecarboxylate.
mp: 204°–205° C.
IR (Nujol): 1725, 1610, 1585, 1540, 1520 cm$^{-1}$.

(41) Ethyl 4-(2-chloro-5-nitrophenyl)-6-methyl-2-(3-pyridyl)-5-pyrimidinecarboxylate.
mp: 160°–162° C.
NMR (DMSO-$d_6$, δ): 0.93 (3H, t, J=7 Hz), 2.76 (3H, s), 4.11 (2H, q, J=7 Hz), 7.47–8.03 (2H, m), 8.25–8.90 (4H, m), 9.5 (1H, m).
Mass M/Z: 398, 400.

(42) Ethyl 6-methyl-4-(2-methylthio-5-nitrophenyl)-2-(3-pyridyl)-5-pyrimidinecarboxylate.
mp: 94°–97° C.
IR (Nujol): 1730, 1602, 1580, 1525, 1340 cm$^{-1}$.

(43) Ethyl 6-methyl-4-(2-methylthio-5-nitrophenyl)-2-[3-(1-methyl)pyridinium]-5-pyrimidinecarboxylate iodide.
mp: 176°–178° C.
IR (Nujol): 1710, 1640, 1602, 1580, 1540, 1512 cm$^{-1}$.

(44) 6-Methyl-4-(2-methylthio-5-nitrophenyl)-2-phenyl-5-pyrimidinecarboxylic acid.
mp: 200°–203° C.
IR (Nujol): 1735, 1695, 1605, 1585, 1520 cm$^{-1}$.

(45) N-(2-Dimethylaminoethyl)-6-methyl-4-(2-methylthio-5-nitrophenyl)-2-phenyl-5-pyrimidinecarboxamide.

mp: 166°–168° C.
IR (Nujol): 1665, 1600, 1575 cm$^{-1}$.
(46) Methyl 6-methyl-4-(2-methylthio-5-nitrophenyl)-2-phenyl-5-pyrimidinecarboxylate.
mp: 171°–173° C.
IR (Nujol): 1730, 1602, 1578, 1542, 1515 cm$^{-1}$.
(47) 5-[3-(2-Dimethylaminoethyl)ureido]-6-methyl-4-(2-methylthio-5-nitrophenyl)-2-phenylpyrimidine.
mp: 190°–192° C.
IR (Nujol): 3350, 3250, 1625, 1520, 1340 cm$^{-1}$.
(48) N-(2-Dimethylaminoethyl)-6-methyl-4-(4-nitrophenyl)-2-phenyl-5-pyrimidinecarboxamide fumarate.
mp: 188°–190° C.
IR (Nujol): 1715, 1665, 1638, 1585, 1545, 1520 cm$^{-1}$.
(49) 4-(4-Nitrophenyl)-2-phenyl-5-pyrimidinecarboxylic acid.
mp: 253°–255° C.
IR (Nujol): 1701, 1565, 1525, 1355 cm$^{-1}$.
(50) N-(2-Dimethylaminoethyl)-4-(4-nitrophenyl)-2-phenyl-5-pyrimidinecarboxamide.
mp: 180°–182° C.
IR (Nujol): 3300, 1640, 1565, 1535, 1520, 1355 cm$^{-1}$.
(51) 5-(4-Methylpiperazin-1-ylcarbonyl)-4-(4-nitrophenyl)-2-phenylpyrimidine.
mp: 165°–166° C.
IR (Nujol): 1630, 1570, 1535, 1355 cm$^{-1}$.
(52) 5-Formyl-6-methyl-4-(3-nitrophenyl)-2-phenyl-5-pyrimidine.
mp: 154°–155° C.
IR (Nujol): 1700, 1535 cm$^{-1}$.
(53) N-(2-Dimethylaminoethyl)-6-methyl-4-(5-nitrothiophen-2-yl)-2-phenyl-5-pyrimidinecarboxamide fumarate.
mp: 205°–206° C.
IR (Nujol): 1705, 1660, 1335 cm$^{-1}$.
(54) Ethyl 4-(4-nitrophenyl)-2-phenyl-5-pyrimidinecarboxylate.
mp: 138°–140° C.
IR (Nujol): 1731, 1570, 1530, 1355, 1295 cm$^{-1}$.
(55) Ethyl 4-(3-nitrophenyl)-2-phenyl-6-trifluoromethyl-5-pyrimidinecarboxylate.
mp: 93°–95° C.
IR (Nujol): 1730, 1590, 1568, 1545, 1215, 1148 cm$^{-1}$.
NMR (DMSO-d$_6$, δ): 1.16 (3H, t, J=7 Hz), 4.31 (2H, q, J=7 Hz), 7.5–7.73 (3H, s), 7.80–8.60 (6H, m).
Mass: 417.
(56) Methyl 4-(2-chloro-5-nitrophenyl)-6-methyl-2-phenyl-5-pyrimidinecarboxylate.
mp: 171°–174° C.
IR (Nujol): 1725, 1550, 1535, 1350, 1285 cm$^{-1}$.
NMR (DMSO-d$_6$, δ): 2.77 (3H, s), 3.65 (3H, s), 7.4–8.55 (8H, m).
Mass (M/Z): 383, 385 (M+).
(57) 6-Methyl-5-(4-methylpiperazin-1-ylcarbonyl)-2-phenyl-4-(3-trifluoromethylphenyl)pyrimidine.
mp: 124°–125° C.
IR (Nujol): 1628, 1545, 1535 cm$^{-1}$.
NMR (CDCl$_3$, δ): 1.2–1.9 (2H, m), 2.0–2.5 (2H, m), 2.1 (3H, s), 2.6 (3H, s), 2.66–3.3 (2H, m), 3.66 (2H, t, J=6 Hz), 7.3–7.8 (5H, m), 7.9–8.6 (4H, m).
Mass (M/Z): 440 (M+).
(58) Methyl 6-methyl-4-(3-hydroxyphenyl)-2-phenyl-5-pyrimidinecarboxylate.
(59) Methyl 2-(4-chlorophenyl)-6-methyl-4-(3-nitrophenyl)-5-pyrimidinecarboxylate.
mp: 105°–107° C.
IR (Nujol): 1725, 1530, 1350 cm$^{-1}$.
NMR (CDCl$_3$, δ): 2.68 (3H, s), 3.8 (3H, s), 7.4, 8.47 (total 4H, ABq, J=9 Hz), 7.6–8.65 (4H, m).
Mass (M/Z): 383, 385 (M+).
(60) Ethyl 6-diethoxymethyl-4-(3-nitrophenyl)-2-phenyl-5-pyrimidinecarboxylate.
mp: 84°–86° C.
IR (Nujol): 1730, 1535, 1355 cm$^{-1}$.
NMR (DMSO-d$_6$, δ): 1.13 (3H, t, J=7 Hz), 1.23 (6H, t, J=7 Hz), 3.69 (2H, q, J=7 Hz), 3.74 (2H, q, J=7 Hz), 4.20 (2H, q, J=7 Hz), 5.70 (1H, s), 7.45–7.65 (3H, m), 7.84 (1H, dd, J=9 Hz, 9 Hz), 8.15 (1H, ddd, J=9 Hz, 2 Hz, 2 Hz), 8.3–8.6 (4H, m).
(61) 6-Methyl-5-(4-methylpiperazin-1-ylcarbonyl)-4-(2-nitrophenyl)-2-phenylpyrimidine.
mp: 114°–115° C.
IR (Nujol): 1620, 1545, 1525, 1360 cm$^{-1}$.
NMR (CDCl$_3$, δ): 1.4–2.0 (2H, m), 2.1 (3H, s), 2.1–2.5 (2H, m), 2.65 (3H, s), 3.25 (2H, t, J=6 Hz), 3.4–3.9 (2H, m), 7.3–7.5 (3H, m), 7.5–8.0 (4H, m), 8.2–8.4 (2H, m)
Mass (M/Z): 417 (M+).
(62) 6-Methyl-5-(4-methylpiperazin-1-ylcarbonyl)-4-(4-nitrophenyl)-2-phenylpyrimidine.
mp: 257°–258° C.
IR (Nujol): 1632, 1530, 1350, 1295, 1270 cm$^{-1}$.
NMR (CDCl$_3$, δ): 1.4–1.9 (2H, m), 2.0–2.4 (2H, m), 2.13 (3H, s), 2.65 (3H, s), 2.7–3.2 (2H, m), 3.7 (2H, q, J=5 Hz), 7.3–7.6 (3H, m), 8.03–8.33 (total 4H, ABq, J=9 Hz), 8.4–8.6 (2H, m)
Mass (M/Z): 417 (M+).

EXAMPLE 20

To a mixture of 6-methyl-4-(3-nitrophenyl)-2-phenyl-5-pyrimidinecarboxylic acid (9 g), dichloromethane (72 ml) and N,N-dimethylformamide (20 ml), thionyl chloride (2.1 ml) was added at 7° C. under ice cooling. After stirring for 1.5 hours at the same condition, 2-dimethylaminoethylamine (5.9 g) was added and stirred for 2 hours. The reaction mixture was adjusted to pH=8.5 by saturated potassium carbonate and extracted with chloroform. The organic layer was washed with water and brine and dried over magnesium sulfate. The solvent was distilled off to give a residue, which was chromatographed on alumina eluting with a mixture of n-hexane and ethyl acetate (5:1). The fractions containing the desired product were combined and concentrated in vacuo. The crystalline residue was recrystallized from diethyl ether to afford N-(2-dimethylaminoethyl)-6-methyl-4-(3-nitrophenyl)-2-phenyl-5-pyrimidinecarboxamide.
mp: 122°–124° C.
IR (Nujol): 1630, 1565, 1530 cm$^{-1}$.
NMR (CDCl$_3$, δ): 2.01 (6H, s), 2.26 (2H, t, J=6 Hz), 2.71 (3H, s), 3.38 (2H, m), 6.35 (1H, br.), 7.38–7.73 (4H, m), 8.13–8.60 (4H, m), 8.75–8.83 (1H, m).
Mass: 405.

EXAMPLE 21

To a mixture of 6-methyl-4-(3-nitrophenyl)-2-phenyl-5-pyrimidinecarboxylic acid (5 g), dichloromethane (45 ml) and N,N-dimethylformamide (11 ml), thionyl chloride (2.1 g) was added at 7° C. under ice cooling. After stirring for 1.5 hours at the same condition, to a solution of N-methylpiperazine (3.7 g) in dichloromethane (37 ml), the reaction mixture was added under ice cooling and stirred for 2 hours. The reaction mixture was adjusted to pH=8.5 by saturated potassium carbonate and extracted with chloroform. The organic layer was washed with water and brine and dried over magnesium sulfate. The solvent was distilled off to give a residue, which was chromatographed on alumina eluting with a chloroform. The fractions containing the desired product were combined and concentrated in vacuo. The crystalline residue was recrystallized from diethyl ether to afford 6-methyl-5-(4-methylpiperazin-1-ylcarbonyl)-4-(3-nitrophenyl)-2-phenyl-pyrimidine (3.5 g).
mp: 153°–155° C.
IR (Nujol): 1634, 1530, 1345 cm$^{-1}$.
NMR (CDCl$_3$, δ): 1.60–2.10 (2H, m), 2.23 (3H, s), 2.45 (2H, t, J=6 Hz), 2.70 (3H, s), 2.86–3.30 (2H, m), 3.80 (2H, t, J=6 Hz), 7.35–7.80 (4H, m), 8.15–8.85 (5H, m).
Mass 417.

EXAMPLE 22

The following compounds were prepared according to the similar manner to that of Example 20 or 21.
(1) N-(2-Diethylaminoethyl)-6-methyl-4-(3-nitrophenyl)-2-phenyl-5-pyrimidinecarboxamide.
mp: 109°–111° C.
IR (Nujol): 3200, 1625, 1530 cm$^{-1}$.
NMR (CDCl$_3$, δ): 0.79 (6H, t, J=7 Hz), 2.33 (4H, q, J=7 Hz), 2.40 (2H, t, J=6 Hz), 3.37 (2H, q-like J=6 Hz), 6.45 (1H, br.), 7.35–7.72 (4H, m), 8.15–8.4 (2H, m), 8.4–8.6 (2H, m), 8.80 (1H, m).
Mass: 433 (M+).
(2) N-(3-Dimethylaminopropyl)-6-methyl-4-(3-nitrophenyl)-2-phenyl-5-pyrimidinecarboxamide.
mp: 137°–139° C.
IR (Nujol): 1630, 1565, 1530 cm$^{-1}$.
NMR (CDCl$_3$, δ): 1.55 (2H, m), 1.96 (6H, s), 2.1–2.3 (2H, m), 2.71 (3H, s), 3.45 (2H, m), 7.40–7.83 (5H, m), 8.2–8.63 (4H, m), 8.86 (1H, m).
Mass: 419.
(3) N-[2-(1-Pyrrolidinyl)ethyl]-6-methyl-4-(3-nitrophenyl)-2-phenylpyrimidinecarboxamide.
mp: 133° C.
IR (Nujol): 1630, 1565, 1530 cm$^{-1}$.
NMR (CDCl$_3$, δ): 1.46–1.70 (4H, m), 2.1–2.35 (4H, m), 2.35–2.55 (2H, m), 2.70 (3H, s), 3.23–3.50 (2H, m), 6.36 (1H, br.), 7.36–7.73 (4H, m), 8.15–8.60 (4H, m), 8.73–8.83 (1H, m).
(4) N-[(1-Ethyl-2-pyrrolidinyl)methyl]-6-methyl-4-(3-nitrophenyl)-2-phenyl-5-pyrimidinecarboxamide.
mp: 88°–90° C.
IR (Nujol): 1630, 1565, 1530 cm$^{-1}$.
NMR (CDCl$_3$, δ): 0.85 (3H, t, J=7 Hz), 1.4–2.6 (8H, m), 2.7 (3H, s), 2.85–3.73 (3H, m), 6.35 (1H, br.), 7.36–7.80 (4H, m), 8.15–8.65 (4H, m), 8.70–8.85 (1H, m).
(5) N-(2-Dimethylaminoethyl)-6-methyl-4-(4-nitrophenyl)-2-phenyl-5-pyrimidinecarboxamide.
mp: 148°–149° C.
IR (Nujol): 3260, 1640 cm$^{-1}$.
NMR (CDCl$_3$, δ): 1.98 (6H, s), 2.22 (2H, t, J=6 Hz), 3.35 (2H, q-like, J=6 Hz), 6.30 (1H, br.), 7.4–7.6 (3H, m), 8.07, 8.30 (4H, ABq, J=9 Hz), 8.4–8.6 (2H, m).
Mass: 405 (M+).
(6) N-(2-Dimethylaminoethyl)-6-methyl-4-(3-nitrophenyl)-2-phenyl-5-pyrimidinecarboxamide fumarate.
mp: 200°–201° C.
IR (KBr): 1640, 1530 cm$^{-1}$.
(7) 6-Methyl-4-(3-nitrophenyl)-N-[2-(1-morpholino)ethyl]-2-phenyl-5-pyrimidinecarboxamide.
mp: 165°–167° C.
IR (Nujol): 3400, 1625, 1565, 1530, 1350 cm$^{-1}$.
NMR (CDCl$_3$, δ): 2.15–2.53 (6H, m), 2.70 (3H, s), 3.25–3.70 (6H, m), 6.15–6.50 (1H, m), 7.33–7.80 (4H, m), 8.10–8.90 (5H, m).
Mass: 447.
(8) N-(2-Acetylaminoethyl)-6-methyl-4-(3-nitrophenyl)-2-phenyl-5-pyrimidinecarboxamide.
mp: 199°–201° C.
IR (Nujol): 3300, 1640, 1590, 1540 cm$^{-1}$.
NMR (DMSO-d$_6$, δ): 1.75 (3H, s), 2.61 (3H, s), 2.87–3.40 (4H, m), 7.43–7.63 (3H, m), 7.72 (1H, br.), 7.85 (1H, d, J=7 Hz), 8.15–8.80 (6H, m).
Mass: 419.
(9) 6-Methyl-5-(4-methylpiperazin-1-ylcarbonyl)-4-(3-nitrophenyl)-2-phenylpyrimidine fumarate.
mp: 245°–246° C.
IR (Nujol): 1715, 1645, 1530 cm$^{-1}$.
(10) N-[3-(1-Ethyl)piperidinyl]-6-methyl-4-(3-nitrophenyl)-2-phenyl-5-pyrimidinecarboxamide.
mp: 146°–148° C.
IR (Nujol): 3290, 1635, 1525, 1350 cm$^{-1}$.
NMR (CDCl$_3$, δ): 0.85 (3H, t, J=7 Hz), 1.1–2.5 (8H, m), 2.23 (2H, q, J=7 Hz), 2.70 (3H, s) 4.1–4.33 (1H, m), 6.3–6.6 (1H, m), 7.35–7.73 (4H, m), 8.15–8.83 (5H, m).
Mass (M/Z): 444 (M−1).
(11) N-(2-Trimethylammonioethyl)-6-methyl-4-(3-nitrophenyl)-2-phenyl-5-pyrimidinecarboxamide iodide.
mp: 228°–230° C.
IR (Nujol): 3390, 1670, 1585, 1525, 1350 cm$^{-1}$.
(12) N-(2-Hydroxyethyl)-6-methyl-4-(3-nitrophenyl)-2-phenyl-5-pyrimidinecarboxamide.
mp: 190°–192° C.
IR (Nujol): 3300, 1630, 1550, 1520, 1355 cm$^{-1}$.
(13) N-(2-Chloroethyl)-6-methyl-4-(3-nitrophenyl)-2-phenyl-5-pyrimidinecarboxamide.
mp: 199°–200° C.
IR (Nujol): 3300, 1640, 1590, 1530 cm$^{-1}$.
(14) 6-Methyl-4-(3-nitrophenyl)-2-phenyl-N-[2-(4-thiomorpholino)ethyl]-5-pyrimidinecarboxamide.
mp: 168°–169° C.
IR (Nujol): 3210, 1620, 1565, 1530, 1350 cm$^{-1}$.
(15) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.
(16) N-(2-Dimethylaminoethyl)-[6-methyl-4-(3-nitrophenyl)-2-phenyl-5-pyrimidinyl]acetoamide.
mp: 185°–187° C.
IR (Nujol): 3300, 1650, 1530 cm$^{-1}$.
NMR (CDCl$_3$, δ): 2.19 (6H, s), 2.39 (2H, t, J=6 Hz), 2.67 (3H, s), 3.38 (2H, q-like J=6 Hz), 3.57 (2H, s), 6.20 (1H, t, J=6 Hz), 7.35–7.55 (3H, m), 7.60 (1H, dd, J=8 Hz, 8 Hz), 8.05 (1H, ddd, J=8 Hz, 2 Hz, 2 Hz), 8.2–8.6 (4H, m).
Mass (M/Z): 419 (M+).
(17) N-(2-Dimethylaminoethyl)-6-ethyl-4-(3-nitrophenyl)-2-phenyl-5-pyrimidinecarboxamide.
mp: 106°–109° C.
IR (Nujol): 3200, 1630, 1530, 1350 cm$^{-1}$.
NMR (CDCl$_3$, δ): 1.45 (3H, t, J=7 Hz), 2.01 (6H, s), 2.25 (2H, t, J=6 Hz), 3.0 (2H, q, J=7 Hz), 3.36 (2H, q-like, J=6 Hz), 6.37 (1H, br.), 7.35–7.75 (4H, m), 8.15–8.40 (2H, m), 8.40–8.65 (2H, m), 8.8 (1H, m).

Mass: 419.
(18) N-(2-Dimethylaminoethyl)-4-(3-nitrophenyl)-2-phenyl-6-trifluoromethyl-5-pyrimidinecarboxyamide.
mp: 174°–175° C.
IR (Nujol): 3300, 1645, 1575, 1541, 1540, 1355 cm$^{-1}$.
NMR (CDCl$_3$, δ): 2.07 (6H, s), 2.33 (2H, t, J=6 Hz), 3.37 (2H, t, d, J=6 Hz, 6 Hz), 6.61 (1H, t, J=6 Hz), 7.4–7.8 (4H, m), 8.16–8.63 (4H, m), 8.73–8.83 (1H, m).
Mass: 459.
(19) N-(2-Dimethylaminoethyl)-6-methyl-4-(2-methylthio-5-nitrophenyl)-2-phenyl-5-pyrimidinecarboxamide.
mp: 166°–168° C.
IR (Nujol): 1665, 1600, 1575 cm$^{-1}$.
NMR (CDCl$_3$, δ): 2.03–2.35 (2H, m), 2.08 (6H, s), 2.52 (3H, s), 2.74 (3H, s), 3.26 (2H, m), 6.4 (1H, br.), 7.3–7.6 (4H, m), 8.1–8.65 (4H, m).
Mass: 451.
(20) N-(2-Dimethylaminoethyl)-6-methyl-4-(4-nitrophenyl)-2-phenyl-5-pyrimidinecarboxamide fumarate.
mp: 188°–190° C.
IR (Nujol): 1715, 1665, 1638, 1585, 1545, 1520 cm$^{-1}$.
(21) N-(2-Dimethylaminoethyl)-4-(4-nitrophenyl)-2-phenyl-5-pyrimidinecarboxamide.
mp: 180°–182° C.
IR (Nujol): 3300, 1640, 1565, 1535, 1520, 1355 cm$^{-1}$.
NMR (CDCl$_3$, δ): 2.1 (6H, s), 2.33 (2H, t, J=5 Hz), 3.42 (2H, q-like, J=5 Hz), 6.43 (1H, br.) 7.3–7.7 (3H, m), 7.85–8.6 (6H, m), 8.95 (1H, s).
Mass: 391.
(22) 5-(4-Methylpiperazin-1-ylcarbonyl)-4-(4-nitrophenyl)-2-phenylpyrimidine.
mp: 165°–166° C.
IR (Nujol): 1630, 1570, 1535, 1355 cm$^{-1}$.
NMR (CDCl$_3$, δ): 1.7–2.1 (2H, m), 2.16 (3H, s), 2.16–2.50 (2H, m), 2.8–3.15 (2H, m), 3.55–3.90 (2H, m), 7.3–7.7 (3H, m), 7.9–8.6 (6H, m), 8.82 (1H, s).
Mass: 403.
(23) N-(2-Dimethylaminoethyl)-6-methyl-4-(5-nitrothiophen-2-yl)-2-phenyl-5-pyrimidinecarboxamide fumarate.
mp: 205°–206° C.
IR (Nujol): 1705, 1660, 1335 cm$^{-1}$.
(24) 2-(4-Chlorophenyl)-6-methyl-5-(4-methylpiperazin-1-ylcarbonyl)-4-(3-nitrophenyl)pyrimidine.
mp: 136°–137° C.
IR (Nujol): 1632, 1585, 1550, 1535, 1355 cm$^{-1}$.
NMR (CDCl$_3$, δ): 1.53–1.9 (2H, m), 2.15 (3H, s), 2.2–2.5 (2H, m), 2.61 (3H, s), 2.76–3.1 (2H, m), 3.56–3.9 (2H, m), 7.3–8.8 (4H, m), 7.4–8.46 (total 4H, ABq, J=8 Hz).
Mass (M/Z): 451, 453 (M+).
(25) 5-(4-Methylpiperazin-1-ylcarbonyl)-4-(4-nitrophenyl)-2-(4-pyridyl)pyrimidine.
mp: 175°–176° C.
IR (Nujol): 1622, 1575, 1530, 1355 cm$^{-1}$.
NMR (CDCl$_3$, δ): 1.8–2.06 (2H, m), 2.16 (3H, s), 2.25–2.50 (2H, m), 2.85–3.05 (2H, m), 3.6–3.85 (2H, m), 8.05 (2H, dd, J=2, 9 Hz), 8.32 (2H, dd, J=2, 9 Hz), 8.35 (2H, dd, J=2, 5 Hz), 8.76 (2H, dd, J=2, 5 Hz), 8.89 (1H, s).
Mass (M/Z): 404 (M+).
(26) 2-(4-Chlorophenyl)-5-(4-methylpiperazin-1-ylcarbonyl)-4-(4-nitrophenyl)pyrimidine.
mp: 146°–147° C.
IR (Nujol): 1639, 1560, 1348 cm$^{-1}$.
NMR (CDCl$_3$, δ): 1.7–2.05 (2H, m), 2.14 (3H, s), 2.2–2.5 (2H, m), 2.8–3.2 (2H, m), 3.6–3.85 (2H, m), 7.47, 8.51 (total 4H, ABq, J=8 Hz), 8.06, 8.37 (total 4H, ABq, J=8 Hz), 8.86 (1H, s).
Mass (M/Z): 437, 439 (M+).
(27) 5-(4-Methylpiperazin-1-ylcarbonyl)-4-(3-nitrohenyl)-2-phenylpyrimidine.
mp: 177°–179° C.
IR (Nujol): 1625, 1585, 1555, 1525, 1350 cm$^{-1}$.
NMR (CDCl$_3$, δ): 2.37 (2H, t, J=5 Hz), 1.8–2.15 (2H, m), 2.2 (3H, s), 3.1 (2H, t, J=6 Hz), 3.76 (2H, t, J=5 Hz), 7.4–7.9 (4H, m), 8.1–8.8 (5H, m), 8.83 (1H, s).
Mass (M/Z): 463 (M+).
(28) 2-(4-Chlorophenyl)-5-(4-methylpiperazin-1-ylcarbonyl)-4-(3-nitrophenyl)pyrimidine.
mp: 182°–184° C.
IR (Nujol): 1628, 1550, 1520, 1350 cm$^{-1}$.
NMR (CDCl$_3$, δ): 1.7–2.6 (4H, m), 2.2 (3H, s), 2.9–3.3 (2H, m), 3.75 (2H, t, J=5 Hz), 7.46, 8.5 (total 4H, ABq, J=8 Hz), 7.76–8.8 (4H, m), 8.83 (1H, s).
Mass (M/Z): 437, 439 (M+).
(29) 6-Methyl-4-(3-nitrophenyl)-2-phenyl-5-(piperazin-1-ylcarbonyl)pyrimidine.
mp: 171°–172° C.
IR (Nujol): 3300, 1615, 1530, 1345 cm$^{-1}$.
NMR (CDCl$_3$, δ): 2.0–3.26 (10H, m), 3.7 (2H, t, J=5 Hz), 7.3–7.8 (4H, m), 8.16–8.83 (5H, m).
Mass (M/Z): 403 (M+).
(30) 2-(4-Chlorophenyl)-N-(2-dimethylaminoethyl)-4-(4-nitrophenyl)-5-pyrimidinecarboxamide.
mp: 192°–193° C.
IR (Nujol): 3300, 1638, 1565, 1525, 1350 cm$^{-1}$.
NMR (CDCl$_3$, δ): 2.31 (2H, t, J=6 Hz), 2.05 (6H, s), 3.39 (2H, t, d, J=6 Hz), 6.36 (1H, br), 7.45, 8.35 (total 4H, ABq, J=9 Hz), 7.98, 8.49 (total 4H, ABq, J=9 Hz), 9.0 (1H, s).
Mass (M/Z): 423, 425 (M+).
(31) N-(2-Dimethylaminoethyl)-4-(4-nitrophenyl)-2-(4-pyridyl)-5-pyrimidinecarboxamide.
mp: 186°–187° C.
IR (Nujol): 3280, 1640, 1600, 1565, 1528, 1350 cm$^{-1}$.
NMR (CDCl$_3$, δ): 2.06 (6H, s), 2.33 (2H, t, J=5 Hz), 3.4 (2H, q, J=5 Hz), 6.45 (1H, br), 8.05, 8.4 (total 4H, ABq, J=9 Hz), 8.3 (2H, dd, J=2, 5 Hz), 8.8 (2H, dd, J=2, 5 Hz), 9.1 (1H, s).
Mass (M/Z): 391 (M−1).
(32) 2-(4-Chlorophenyl)-N-(2-dimethylaminoethyl)-6-methyl-4-(3-nitrophenyl)-5-pyrimidinecarboxamide.
mp: 137°–138° C.
IR (Nujol): 3250, 1640, 1525, 1355 cm$^{-1}$.
NMR (CDCl$_3$, δ): 2.03 (6H, s), 2.2–2.46 (2H, m), 2.7 (3H, s), 3.37 (2H, q, J=7 Hz), 6.4 (1H, br), 7.4, 8.45 (total 4H, ABq, J=2 Hz), 7.55–7.8 (1H, m), 8.1–8.9 (3H, m).
Mass (M/Z): 437, 439 (M+).
(33) N-(2-Dimethylaminoethyl)-4-(3-nitrophenyl)-2-phenyl-5-pyrimidinecarboxamide.
mp: 165°–167° C.
IR (Nujol): 3300, 1630, 1520, 1355 cm$^{-1}$.
NMR (CDCl$_3$, δ): 2.1 (6H, s), 2.36 (2H, t, J=5 Hz), 3.43 (2H, dt, J=5 Hz), 6.5 (1H, t, J=5 Hz), 7.4–7.8 (4H, m), 8.05–8.9 (5H, m), 9.0 (1H, s).
Mass (M/Z): 391 (M+).
(34) 6-Methyl-4-(3-nitrophenyl)-2-phenyl-5-[4-(3,4,5-trimethoxybenzyl)piperazin-1-ylcarbonyl]pyrimidine
IR (Nujol): 1630, 1592, 1523, 1350 cm$^{-1}$.

NMR (CDCl$_3$, δ): 1.6–2.5 (4H, m), 2.64 (3H, s), 2.75–3.2 (2H, m), 3.29 (2H, s), 3.45–3.7 (2H, m), 3.8 (9H, s), 6.42 (2H, s), 7.35–7.75 (4H, m), 8.1–8.8 (5H, m).
Mass (M/Z): 583 (M+).
(35) 4-(3-Difluoromethoxyphenyl)-6-methyl-5-(4-methylpiperazin-1-ylcarbonyl)-2-phenylpyrimidine.
mp: 82°–84° C.
IR (Nujol): 1624, 1540 cm$^{-1}$.
NMR (CDCl$_3$, δ): 1.2–1.65 (2H, m), 2.0–2.42 (2H, m), 2.13 (3H, s), 2.63 (3H, s), 2.75–3.1 (2H, m), 3.7 (2H, t, J=6 Hz), 6.56 (1H, t, J=82 Hz), 7.1–7.83 (7H, m), 8.4–8.62 (2H, m).
Mass (M/Z): 438 (M+).
(36) N-(2-Dimethylaminoethyl)-6-methyl-4-(3-nitrophenyl)-2-(4-pyridyl)-5-pyrimidinecarboxamide.
mp: 130°–133° C.
IR (Nujol): 1640, 1530, 1355 cm$^{-1}$.
NMR (CDCl$_3$, δ): 2.06 (6H, s), 2.3 (2H, t, J=5 Hz), 2.7 (3H, s), 3.4 (2H, d, t, J=5 Hz), 6.83 (1H, br), 7.46–8.83 (8H, m).
Mass (M/Z): 406 (M+).
(37) 6-Methyl-5-(4-methylpiperazin-1-ylcarbonyl)-4-(3-nitrophenyl)-2-(4-pyridyl)pyrimidine.
mp: 161°–162° C.
IR (Nujol): 1625, 1530, 1350 cm$^{-1}$.
NMR (CDCl$_3$, δ): 1.5–2.1 (2H, m), 2.16 (3H, s), 2.2–2.5 (2H, m), 2.7 (3H, s), 2.8–3.25 (2H, m), 3.74 (2H, t, J=5 Hz), 7.4–8.9 (4H, m), 8.31, 8.8 (total 4H, ABq, J=7 Hz).
Mass (M/Z): 418 (M+).
(38) N-Methyl-N-(2-hydroxyethyl)-6-methyl-4-(3-nitrophenyl)-2-phenyl-5-pyrimidinecarboxamide.
NMR (CDCl$_3$, δ): 2.65 (3H, s), 2.76 (3H, s), 3.30–4.0 (4H, m), 7.40–7.83 (4H, m), 8.15–8.90 (5H, m).
Mass (M/Z): 392 (M+).

EXAMPLE 23

To a suspension of lithium aluminum hydride (12.24 g) in a mixture of dry tetrahydrofuran (180 ml) and diethyl ether (360 ml) was dropwise added a solution of methyl 6-methyl-2-phenyl-4-(3-nitrophenyl)-5-pyrimidinecarboxylate in dry tetrahydrofuran (180 ml) under cooling at −50°~−40° C. The excess lithium aluminum hydride was decomposed by a careful addition to ice water. The separated organic layer was washed with 15% sulfuric acid (400 ml) and extracted with ethyl acetate (1 l). The organic layer was washed with saturated aqueous sodium bicarbonate and aqueous sodium chloride successively and concentrated in vacuo. The residue was recrystallized from diethyl ether to give 5-hydroxymethyl-6-methyl-2-phenyl-4-(3-nitrophenyl)-pyrimidine (30 g).
mp: 177°–178° C.
IR (Nujol): 1590, 1360, 1025 cm$^{-1}$.
NMR (DMSO-d$_6$, δ): 2.77 (3H, s), 4.50 (2H, d, J=4 Hz), 5.50 (1H, t, J=4 Hz), 7.3–7.67 (3H, m), 7.80 (1H, dd, J=8 Hz, 8 Hz), 8.1–8.6 (4H, m), 8.67 (1H, dd, J=2 Hz, 2 Hz).
Mass: 321 (M+).

EXAMPLE 24

A suspension of ethyl 6-methyl-2-phenyl-4-(4-nitrophenyl)-5-pyrimidinecarboxylate (39 g) and aqueous sodium hydroxide (5.19 g in 10 ml H$_2$O) in ethanol (390 ml) and water (195 ml) was refluxed for 10 hours. After evaporating the solvent, the residue was dissolved in a suspension of water (200 ml) and chloroform (200 ml) under stirring. The separated aqueous layer was adjusted to pH 3.0 with 10% aqueous HCl. The resulting precipitate was collected by filtration, washed with water and dried in vacuo to give 6-methyl-2-phenyl-4-(4-nitrophenyl)-5-pyrimidinecarboxylic acid (14.3 g).
mp: 247°–248° C. (dec.).
IR (Nujol): 1690, 1608, 1355 cm$^{-1}$.
NMR (TFA, δ): 3.20 (3H, s), 7.6–8.0 (3H, m), 8.17, 8.50 (4H, ABq, J=9 Hz), 8.2–8.5 (2H, m).

EXAMPLE 25

The following compounds were prepared according to the similar manner to that of Example 5 or 24.
(1) 6-Methyl-4-(3-nitrophenyl)-2-phenyl-5-pyrimidinylacetic acid.
mp: 222°–224° C. (dec.).
IR (Nujol): 1700, 1530 cm$^{-1}$.
NMR (TFA, δ): 3.10 (3H, s), 4.15 (2H, s), 7.5–8.8 (9H, m).
(2) 6-Ethyl-4-(3-nitrophenyl)-2-phenyl-5-pyrimidinecarboxylic acid.
mp: 184°–185° C.
IR (Nujol): 1720, 1540, 1350 cm$^{-1}$.
NMR (DMSO-d$_6$, δ): 1.39 (3H, t, J=7 Hz), 3.0 (2H, q, J=7 Hz), 7.45–8.70 (9H, m).
Mass: 349.
(3) 4-(3-Nitrophenyl)-2-phenyl-6-trifluoromethyl-5-pyrimidinecarboxylic acid.
mp: 313°–315° C. (dec.).
IR (Nujol): 1615, 1530 cm$^{-1}$.
NMR (DMSO-d$_6$, δ): 7.4–8.0 (4H, m), 8.25 (4H, m), 8.96–9.1 (1H, m).
Mass: 389.
(4) 6-Methyl-4-(2-methylthio-5-nitrophenyl)-2-phenyl-5-pyrimidinecarboxylic acid.
mp: 200°–203° C.
IR (Nujol): 1735, 1695, 1605, 1585, 1520 cm$^{-1}$.
NMR (DMSO-d$_6$, δ): 2.53 (3H, s), 2.70 (3H, s), 7.3–7.8 (4H, m), 8.1–8.7 (4H, m).
(5) 4-(4-Nitrophenyl)-2-phenyl-5-pyrimidinecarboxylic acid.
mp: 253°–255° C.
IR (Nujol): 1701, 1565, 1525, 1355 cm$^{-1}$.
NMR (DMSO-d$_6$, δ): 7.4–7.73 (3H, m), 7.80–8.65 (6H, m), 9.3 (1H, s).
Mass: 321.
(6) 6-Methyl-4-(3-nitrophenyl)-2-(4-pyridyl)-5-pyrimidinecarboxylic acid.
mp: 292° C. (dec.).
IR (Nujol): 1615, 1530, 1350 cm$^{-1}$.
NMR (TFA, δ): 3.01 (3H, s), 7.6–9.4 (8H, m)
Mass (M/Z): 336 (M+).
(7) 4-(4-Nitrophenyl)-2-(4-pyridyl)-5-pyrimidinecarboxylic acid.
mp: 350° C. (dec.).
IR (Nujol): 1720, 1615, 1510, 1350 cm$^{-1}$.
NMR (TFA, δ): 7.95, 8.46 (4H, ABq, J=9 Hz), 9.0, 9.26 (4H, ABq, J=7 Hz), 9.7 (1H, s).
Mass (M/Z): 322 (M+).
(8) 2-(4-Chlorophenyl)-4-(4-nitrophenyl)-5-pyrimidinecarboxylic acid.
mp: 310° C. (dec.).
IR (Nujol): 1715, 1622, 1530, 1355 cm$^{-1}$.
NMR (DMSO-d$_6$, δ): 7.61, 8.38 (4H, ABq, J=9 Hz), 8.03, 8.5 (4H, ABq, J=9 Hz), 9.15 (1H, s).
Mass (M/Z): 355 (M+).
(9) 2-(4-Chlorophenyl)-6-methyl-4-(3-nitrophenyl)-5-pyrimidinecarboxylic acid.

mp: 205°–206° C.
IR (Nujol): 1695, 1525, 1355 cm$^{-1}$.
NMR (DMSO-d$_6$, δ): 2.66 (3H, s), 7.54, 8.42 (total 4H, ABq, J=9 Hz), 7.7–8.6 (4H, m).
Mass (M/Z): 369, 371 (M+).
(10) 2-(4-Chlorophenyl)-4-(3-nitrophenyl)-5-pyrimidinecarboxylic acid.
mp: 268°–270° C.
IR (Nujol): 1740, 1705, 1525, 1350 cm$^{-1}$.
NMR (DMSO-d$_6$, δ): 7.5–8.6 (8H, m), 9.26 (1H, s).
Mass (M/Z): 355 (M+).
(11) 4-(3-Nitrophenyl)-2-phenyl-5-pyrimidinecarboxylic acid.
mp: 195° C. (fused), 210° C. (clarified).
IR (Nujol): 1705, 1560, 1525, 1350 cm$^{-1}$.
NMR (DMSO-d$_6$, δ): 7.4–8.6 (9H, m), 9.3 (1H, s).
Mass (M/Z): 321 (M+).
(12) 4-(3-Difluoromethoxyphenyl)-6-methyl-2-phenyl-5-pyrimidinecarboxylic acid.
mp: 194°–195° C.
IR (Nujol): 1713, 1555, 1235 cm$^{-1}$.
NMR (DMSO-d$_6$, δ): 2.64 (3H, s), 7.32 (1H, t, J=75 Hz), 7.3–7.75 (7H, m), 8.3–8.6 (2H, m).
Mass (M/Z): 356 (M+).

EXAMPLE 26

To a solution of methyl mercaptan-DMF solution (methylmercaptan 66 g/DMF 306 g) (3.8 ml) and methyl 4-(2-chloro-5-nitrophenyl)-6-methyl-2-phenyl-5-pyrimidinecarboxylate (1.5 g) in tetrahydrofuran (25 ml) was added and the mixture was stirred for 3 hours at ambient temperature. The reaction mixture was evaporated in vacuo and the residue was dissolved in a mixture of water (50 ml) and ethyl acetate (100 ml). The organic layer was washed with a saturated aqueous solution of sodium chloride and dried over magnesium sulfate. The solvent was distilled off to give a residue, which was chromatographed on silicagel eluting with a mixture of n-hexane and ethyl acetate (10:1). The fractions containing the desired product were combined and concentrated in vacuo. The crystalline residue was recrystallized from n-hexane to afford methyl 6-methyl-4-(2-methylthio-5-nitrophenyl)-2-phenyl-5-pyrimidinecarboxylate (0.2 g).
mp: 171°–173° C.
IR (Nujol): 1730, 1602, 1578, 1542, 1515 cm$^{-1}$.
NMR (CDCl$_3$, δ): 2.50 (3H, s), 2.76 (3H, s), 3.68 (3H, s), 7.4–7.55 (4H, m), 8.1–8.56 (4H, m).
Mass (M/Z): 395 (M+).

EXAMPLE 27

The following compounds were prepared according to the similar manner to that of Example 12 or 26.
(1) Ethyl 6-methyl-4-(2-methylthio-5-nitrophenyl)-2-(3-pyridyl)-5-pyrimidinecarboxylate.
mp: 94°–97° C.
IR (Nujol): 1730, 1602, 1580, 1525, 1340 cm$^{-1}$.
NMR (CDCl$_3$, δ): 1.06 (3H, t, J=7 Hz), 2.51 (3H, s), 2.79 (3H, s), 4.17 (2H, q, J=7 Hz), 7.26–7.50 (2H, m), 8.13 (1H, d, J=3 Hz), 8.26 (1H, dd, J=3, 7 Hz), 8.67–8.82 (2H, m), 9.65 (1H, br.).
Mass: 409.
(2) Ethyl 6-methyl-4-(2-methylthio-5-nitrophenyl)-2-[3-(1-methyl)pyridinium]-5-pyrimidinecarboxylate iodide.
mp: 176°–178° C.
IR (Nujol): 1710, 1640, 1602, 1580, 1540, 1512 cm$^{-1}$.
(3) 6-Methyl-4-(2-methylthio-5-nitrophenyl)-2-phenyl-5-pyrimidinecarboxylic acid.
mp: 200°–203° C.
IR (Nujol): 1735, 1695, 1605, 1585, 1520 cm$^{-1}$.
(4) N-(2-Dimethylaminoethyl)-6-methyl-4-(2-methylthio-5-nitrophenyl)-2-phenyl-5-pyrimidinecarboxamide.
mp: 166°–168° C.
IR (Nujol): 1665, 1600, 1575 cm$^{-1}$.
(5) 5-[3-(2-Dimethylaminoethyl)ureido]-6-methyl-4-(2-methylthio-5-nitrophenyl)-2-phenylpyrimidine.
mp: 190°–192° C.
IR (Nujol): 3350, 3250, 1625, 1520, 1340 cm$^{-1}$.

EXAMPLE 28

To a mixture of ethyl 6-methyl-4-(2-methylthio-5-nitrophenyl)-2-phenyl-5-pyrimidinecarboxylate (2 g) and chloroform (10 ml), 3-chloroperoxybenzoic acid (2.1 g) in a mixture of chloroform (3 ml) and acetone (1 ml) were dropwise added at 4°–6° with stirring, which was continued under the same condition for 1 hours. The reaction mixture was extracted with chloroform (100 ml), washed successively with aqueous solutions of sodium iodide, sodium hydrogen sulfite, sodium hydrogen carbonate, and sodium chloride, and dried over magnesium sulfate. The solvent was distilled off. The residue was chromatographed on silica gel eluting with a mixture of n-hexane and ethyl acetate (10:1) The fractions containing the desired product were combined and concentrated in vacuo. The crystalline residue was recrystallized from diisopropyl ether to afford ethyl 6-methyl-4-(2-methylsulfonyl-5-nitrophenyl)-2-phenyl-5-pyrimidinecarboxylate (0.6 g).
mp: 150°–151° C.
IR (Nujol): 1730, 1535, 1155 cm$^{-1}$.
NMR (DMSO-d$_6$, δ): 0.88 (3H, t, J=7 Hz), 2.82, (3H, s), 3.37 (3H, s), 4.1 (2H, q, J=7 Hz), 7.52–7.77 (3H, m), 8.3–8.67 (5H, m).
Mass: 441.

EXAMPLE 29

A mixture of 6-methyl-4-(2-methylthio-5-nitrophenyl)-2-phenyl-5-pyrimidinecarboxylic acid (12.5 g), triethylamine (4.57 ml) and diphenylphosphorylazide (7.07 ml) in benzene (125 ml) was refluxed for 2 hours and to the reaction mixture was added 2-dimethylaminoethylamine (3.47 g). After the reflux was continued for 2 hours, the reaction mixture was poured into a mixture of a diethyl ether (100 ml) and saturated sodium hydrogen carbonate. The separated organic layer was dried over magnesium sulfate and evaporated in vacuo. The residue was chromatographed on alumina eluting with chloroform. The fractions containing the desired product were combined and concentrated in vacuo. The residue was recrystallized from diethyl ether to afford 5-[3-(2-dimethylaminoethyl)ureido]-6-methyl-4-(2-methylthio-5-nitrophenyl)-2-phenylpyrimidine.
mp: 190°–192° C.
IR (Nujol): 3350, 3250, 1625, 1520, 1340 cm$^{-1}$.
NMR (CDCl$_3$, δ): 2.15 (6H, s), 2.28–2.43 (2H, t, J=6 Hz), 2.50 (3H, s), 2.65 (3H, s), 3.15 (2H, t, d, J=6 Hz, J=6 Hz), 5.16 (1H, br.) 7.26–7.53 (4H, m), 7.76 (1H, br.), 8.1–8.53 (4H, m).
Mass (M/Z): 466 (M+).

EXAMPLE 30

The following compounds were prepared according to the similar manner to that of Example 29.
(1) 5-[3-(1-Ethylpiperidin-3-yl)ureido]-6-methyl-4-(3-nitrophenyl)-2-phenylpyrimidine.
mp: 206°–208° C.
IR (Nujol): 1625, 1575, 1530, 1352 cm$^{-1}$.
NMR (CDCl$_3$, δ): 1.09 (3H, t, J=7 Hz), 1.1–2.4 (10H, m), 2.56 (3H, s), 3.86 (1H, br.), 5.5–5.75 (1H, m), 6.73 (1H, s), 7.3–7.7 (4H, m), 8.05–8.70 (5H, m).
Mass: 332 (M-128).
(2) 6-Methyl-5-[(4-methylpiperazin-1-yl)-carbonylamino]-4-(3-nitrophenyl)-2-pheylpyrimidine.
mp: 221°–223° C.
IR (Nujol): 3300, 1630, 1555, 1530, 1350 cm$^{-1}$.
NMR (CDCl$_3$, δ): 2.16–2.50 (4H, m), 2.3 (3H, s), 3.3–3.6 (4H, m), 6.01 (1H, s), 7.4–7.76 (4H, m), 8.0–8.7 (5H, m).
Mass M/Z: 432 (M+).

EXAMPLE 31

A mixture of 6-methyl-4-(3-nitrophenyl)-2-phenyl-5-pyrimidinecarboxamide (10 g), sodium chloride (8 g) and phosphorous oxychloride (3.3 g) in 1,2-dichloroethane (50 ml) was refluxed for 10 hours. After removal of the sodium chloride, the reaction mixture was poured into a mixture of dichloromethane (200 ml) and aqueous saturated hydrogen carbonate solution (100 ml). The separated organic layer was dried over magnesium sulfate and evaporated in vacuo. The residue was crystallized from diethyl ether, collected, washed with diethyl ether and dried to give 6-methyl-4-(3-nitrophenyl)-2-phenyl-5-pyrimidinecarbonitrile (6.3 g).
mp: 185°–187° C.
IR (Nujol): 2230, 1525, 1350 cm$^{-1}$.
NMR (CDCl$_3$, δ): 2.90 (3H, s), 7.4–7.9 (4H, m), 8.3–8.7 (4H, m), 9.97 (1H, m).
Mass: 316 (M+).

EXAMPLE 32

To the solution of N-(2-dimethylaminoethyl)-6-methyl-4-(3-nitrophenyl)-2-phenyl-5-pyrimidinecarboxamide (4 g) in ethyl alcohol (10 ml), the solution of fumaric acid (1.15 g) in hot ethyl alcohol (10 ml) was added. The precipitate was filtered off to afford N-(2-dimethylaminoethyl)-6-methyl-4-(3-nitrophenyl)-2-phenyl-5-pyrimidinecarboxamide fumarate.
mp: 200°–201° C.
IR (KBr): 1640, 1530 cm$^{-1}$.
NMR (DMSO-d$_6$, δ): 2.2 (6H, s), 2.38 (2H, t, J=6 Hz), 2.61 (3H, s), 3.31 (2H, m), 6.53 (2H, s), 7.4–7.95 (4H, m), 8.2–8.86 (6H, m).

EXAMPLE 33

The following compounds were prepared according to the similar manner to that of Example 32.
(1) 6-Methyl-5-(4-methylpiperazine)carbonyl-4-(3-nitrophenyl)-2-phenylpyrimidine fumarate.
mp: 245°–246° C.
IR (Nujol): 1715, 1645, 1530 cm$^{-1}$.
NMR (DMSO-d$_6$, δ): 0.95–1.60 (2H, m), 2.0–2.5 (2H, m), 2.03 (3H, s), 2.56 (3H, s), 2.9–3.7 (4H, m), 6.65 (2H, m), 7.4–7.65 (3H, m), 7.75–8.0 (1H, m), 8.15–8.70 (5H, m).
Mass: 417.

(2) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.
NMR (DMSO-d$_6$, δ): 2.3 (2H, t, J=6 Hz), 2.4–2.56 (8H, m), 2.62 (3H, s), 3.26 (2H, t, d, J=6 Hz, 6 Hz), 6.61 (2H, s), 7.4–7.93 (4H, m), 8.2–8.7 (6H, m).
(3) N-(2-Dimethylaminoethyl)-6-methyl-4-(4-nitrophenyl)-2-phenyl-5-pyrimidinecarboxamide fumarate.
mp: 188°–190° C.
IR (Nujol): 1715, 1665, 1638, 1585, 1545, 1520 cm$^{-1}$.
NMR (DMSO-d$_6$, δ): 2.21 (6H, s), 2.25–2.50 (2H, m), 3.31 (2H, m), 6.55 (2H, s), 7.45–7.65 (3H, m), 8.0–8.55 (6H, m), 8.7 (1H, m).
(4) N-(2-Dimethylaminoethyl)-6-methyl-4-(5-nitrothiophen-2-yl)-2-phenyl-5-pyrimidinecarboxamide fumarate.
mp: 205°–206° C.
IR (Nujol): 1705, 1660, 1335 cm$^{-1}$.

EXAMPLE 34

To a solution of N-(2-hydroxyethyl)-6-methyl-4-(3-nitrophenyl)-2-phenyl-5-pyrimidinecarboxyamide (5 g) in a mixture of chloroform (45 ml) and dimethylformamide (10 ml), was dropped thionyl chloride (0.96 ml) in chloroform (4 ml) under ice-cooling and the mixture was refluxed for 4 hours. After evaporating the solvent, the residue was dissolved in a suspension of water (100 ml) and chloroform (200 ml) under stirring. The separated aqueous layer was adjusted to pH 8.5 with saturated aqueous potassium carbonate and evaporated. The resulting precipitate was collected by filtration and washed with diethyl ether to give N-(2-chloroethyl)-6-methyl-4-(3-nitrophenyl)-2-phenyl-5-pyrimidinecarboxamide (1.5 g).
mp: 199°–200° C.
IR (Nujol): 3300, 1640, 1590, 1530 cm$^{-1}$.
NMR (CDCl$_3$, δ): 2.66 (3H, s), 5.96–6.3 (1H, br.), 3.4–3.7 (4H, m), 7.3–7.75 (4H, m), 8.06–8.80 (5H, m).
Mass: 396, 398.

EXAMPLE 35

The following compound was prepared according to the similar manner to that of Example 34.
(1) 5-Bromomethyl-6-methyl-2-phenyl-4-(3-nitrophenyl)pyrimidine.
mp: 163°–164° C.
IR (Nujol): 1550, 1530, 1350 cm$^{-1}$.
NMR (CDCl$_3$, δ): 2.80 (3H, s), 4.47 (2H, s), 7.35–7.55 (3H, m), 7.73 (1H, dd, J=8 Hz, 8 Hz), 8.17 (1H, ddd, J=8 Hz, 2 Hz, 2 Hz), 8.3–8.6 (4H, m), 8.80 (1H, dd, J=2 Hz, 2 Hz).
Mass M/Z: 383, 385 (M+).

EXAMPLE 36

A mixture of N-(2-chloroethyl)-6-methyl-4-(3-nitrophenyl)-2-phenyl-5-pyrimidinecarboxamide (2 g), thiomorpholine (1.52 ml) and sodium-iodide (0.076 g) in isopropylalcohol (20 ml) was refluxed for 7 hours. The reaction mixture was poured into an ethyl acetate (200 ml) and water (100 ml). The separated organic layer was washed with water and brine, dried over magnesium sulfate and evaporated in vacuo. The residue was column chromatographed on alumina eluting with chloroform. The fractions containing the desired product were combined and concentrated in vacuo. The residue was recrystallized from diethyl ether to afford 6-methyl-4-(3-nitrophenyl)-2-phenyl-N-[2-(4-thiomorpholino)ethyl]-5-pyrimidinecarboxamide (0.85 g).
mp: 168°–169° C.
IR (Nujol): 3210, 1620, 1565, 1530, 1350 cm$^{-1}$.
NMR (CDCl$_3$, δ): 2.34 (2H, t, J=6 Hz), 2.47 (8H, s), 2.70 (3H, s), 3.40 (2H, t, d, J=6 Hz, 6 Hz), 6.17 (1H, t, J=6 Hz), 7.40–7.73 (4H, m), 8.15–8.83 (5H, m).
Mass (M/Z): 463 (M+).

EXAMPLE 37

The following compounds were prepared according to the similar manner to that of Example 36.
(1) 6-Methyl-4-(3-nitrophenyl)-N-[2-(1-morpholino)ethyl]-2-phenyl-5-pyrimidinecarboxamide.
mp: 165°–167° C.
IR (Nujol): 3400, 1625, 1565, 1530, 1350 cm$^{-1}$.
(2) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.
NMR (DMSO-d$_6$, δ): 2.3 (2H, t, J=6 Hz), 2.4–2.56 (8H, m), 2.62 (3H, s), 3.26 (2H, t, d, J=6 Hz, 6 Hz), 6.61 (2H, s), 7.4–7.93 (4H, m), 8.2–8.7 (6H, m).
(3) N-(2-Dimethylaminoethyl)-[6-methyl-4-(3-nitrophenyl)-2-phenyl-5-pyrimidinyl]acetoamide.
mp: 185°–187° C.
IR (Nujol): 3300, 1650, 1530.
(4) N-(2-Dimethylaminoethyl)-6-ethyl-4-(3-nitrophenyl)-2-phenyl-5-pyrimidinecarboxamide.
mp: 106°–109° C.
IR (Nujol): 3200, 1630, 1530, 1350 cm$^{-1}$.
(5) N-(2-Dimethylaminoethyl)-4-(3-nitrophenyl)-2-phenyl-6-trifluoromethyl-5-pyrimidinecarboxamide.
mp: 174°–175° C.
IR (Nujol): 3300, 1645, 1575, 1541, 1540, 1355 cm$^{-1}$.
(6) N-(2-Dimethylaminoethyl)-6-methyl-4-(2-methylthio-5-nitrophenyl)-2-phenyl-5-pyrimidinecarboxamide.
mp: 166°–168° C.
IR (Nujol): 1665, 1600, 1575 cm$^{-1}$.
(7) 5-[3-(2-Dimethylaminoethyl)ureido]-6-methyl-4-(2-methylthio-5-nitrophenyl)-2-phenylpyrimidine.
mp: 190°–192° C.
IR (Nujol): 3350, 3250, 1625, 1520, 1340 cm$^{-1}$.
(8) N-(2-Dimethylaminoethyl)-6-methyl-4-(4-nitrophenyl)-2-phenyl-5-pyrimidinecarboxamide fumarate.
mp: 188°–190° C.
IR (Nujol): 1715, 1665, 1638, 1585, 1545, 1520 cm$^{-1}$.
(9) N-(2-Dimethylaminoethyl)-4-(4-nitrophenyl)-2-phenyl-5-pyrimidinecarboxamide.
mp: 180°–182°.
IR (Nujol): 3300, 1640, 1565, 1535, 1520, 1355 cm$^{-1}$.
(10) N-(2-Dimethylaminoethyl)-6-methyl-4-(3-nitrophenyl)-2-phenyl-5-pyrimidinecarboxamide.
IR (Nujol): 1630, 1565, 1530 cm$^{-1}$.
(11) N-(2-Dimethylaminoethyl)-6-methyl-4-(5-nitrothiophen-2-yl)-2-phenyl-5-pyrimidinecarboxamide fumarate.
mp: 205°–206° C.
IR (Nujol): 1705, 1660, 1335 cm$^{-1}$.
(12) N-(2-Dimethylaminoethyl)-6-methyl-4-(4-nitrophenyl)-2-phenyl-5-pyrimidinecarboxamide.
mp: 148°–149° C.
IR (Nujol): 3260, 1640 cm$^{-1}$.
(13) N-(2-Dimethylaminoethyl)-6-methyl-4-(3-nitrophenyl)-2-phenyl-5-pyrimidinecarboxamide fumarate.
mp: 200°–201° C.
IR (KBr): 1640, 1530 cm$^{-1}$.
(14) N-(2-Diethylaminoethyl)-6-methyl-4-(3-nitrophenyl)-2-phenyl-5-pyrimidinecarboxamide.
mp: 109°–111° C.
IR (Nujol): 3200, 1625, 1530 cm$^{-1}$.
(15) N-(3-Dimethylaminopropyl)-6-methyl-4-(3-nitrophenyl)-2-phenyl-5-pyrimidinecarboxamide.
mp: 137°–139° C.
IR (Nujol): 1630, 1565, 1530 cm$^{-1}$.
(16) N-[2-(1-Pyrrolidinyl)ethyl]-6-methyl-4-(3-nitrophenyl)-2-phenylpyrimidinecarboxamide.
mp: 133° C.
IR (Nujol): 1630, 1565, 1530 cm$^{-1}$.
(17) 6-Methyl-N-[2-(4-methylpiperazin-1-yl)ethyl]-4-(3-nitrophenyl)-2-phenylpyrimidinecarboxamide.
mp: 93°–95° C.
IR (Nujol): 3200, 1630, 1350 cm$^{-1}$.
NMR (CDCl$_3$, δ): 2.21 (3H, s), 2.26 (8H, s), 2.3–2.5 (2H, t, J=6 Hz), 2.73 (3H, s), 3.4 (2H, q, J=6 Hz), 6.3 (1H, br), 7.35–7.73 (4H, m), 8.1–8.83 (5H, m).
Mass (M/Z): 460 (M+).
(18) 6-Methyl-4-(3-nitrophenyl)-2-phenyl-N-(2-piperidinoethyl)-5-pyrimidinecarboxamide.
mp: 119°–120° C.
IR (Nujol): 1622, 1565, 1530, 1353 cm$^{-1}$.
NMR (CDCl$_3$, δ): 1.35 (6H, s), 2.0–2.25 (4H, m), 2.3 (2H, t, J=6 Hz), 2.71 (3H, s), 3.4 (2H, q, J=6 Hz), 6.43 (1H, br), 7.3–7.75 (4H, m), 8.1–8.9 (5H, m).
Mass (M/Z): 445 (M+).

EXAMPLE 38

To a solution of 5-hydroxymethyl-6-methyl-4-(3-nitrophenyl)-2-phenylpyrimidine (0.3 g) in ethyl acetate (10 ml) was added activated manganese dioxide (2.4 g) and the mixture was refluxed for 2 hours under stirring vigorously. After allowing to stand to room temperature, manganese dioxide was filtered off. The filtrate was evaporated in vacuo, and the residual precipitate was recrystallized from diethyl ether to give 5-formyl-6-methyl-4-(3-nitrophenyl)-2-phenyl-5-pyrimidine (0.15 g).
mp: 154°–155° C.
IR (Nujol): 1700, 1535 cm$^{-1}$.
NMR (CDCl$_3$, δ): 2.97 (3H, s), 7.5–8.8 (9H, m), 10.13 (1H, s).
Mass (M/Z): 319 (M+).

EXAMPLE 39

To a solution of sodium cyanide (4.8 g) in water (50 ml) was added a suspension of 5-bromomethyl-6-methyl-2-phenyl-4-(3-nitrophenyl)pyrimidine (30 g) in a mixture of ethanol (180 ml) and tetrahydrofuran (180 ml), and the mixture was refluxed for 2 hours. The reaction mixture was poured into a mixture of ice-water (200 ml) and diethyl ether (200 ml). The precipitate was filtered, washed with water, dried in vacuo to give 5-cyanomethyl-6-methyl-2-phenyl-4-(3-nitrophenyl)-pyrimidine (22.5 g).
mp: 219°–221° C.
IR (Nujol): 1535, 1350 cm$^{-1}$.
NMR (CF$_3$COOD, δ): 3.25 (3H, s), 4.28 (2H, s), 7.5–9.0 (9H, m).
Mass M/Z: 330 (M+).

EXAMPLE 40

A solution of N-(2-dimethylaminoethyl)-6-methyl-4-(3-nitrophenyl)-2-phenyl-5-pyrimidinecarboxamide (1 g) and methyl iodide (10.46 ml) in ethyl acetate (2 ml) was stirred for 5 days at room temperature. The reaction mixture was evaporated and the residue was recrystallized from ethyl alcohol to afford N-(2-trimethylammonioethyl)-6-methyl-4-(3-nitrophenyl)-2-phenyl-5-pyrimidinecarboxamide iodide (0.95 g).

mp: 228°–230° C.

IR (Nujol): 3390, 1670, 1585, 1525, 1350 cm$^{-1}$.

NMR (DMSO-$d_6$, $\delta$): 2.63 (3H, s), 3.08 (9H, s), 3.30–3.70 (4H, m), 7.45–8.0 (4H, m), 8.16–8.63 (4H, m), 8.95 (1H, br.).

EXAMPLE 41

A mixture of 5-cyanomethyl-6-methyl-4-(3-nitrophenyl)-2-phenylpyrimidine (5 g), conc. sulfuric acid (12 g) and ethanol (50 ml) was gently refluxed for 72 hours. The reaction mixture was poured into a suspension of chloroform (200 ml) and water (100 ml), and then adjusted to pH 8.5 with 10% aqueous sodium carbonate solution. The separated organic layer was washed with saturated aqueous sodium chloride solution, dried over magnesium sulfate and evaporated in vacuo. The residual substance was recrystallized from diethyl ether-n-hexane to give ethyl 6-methyl-4-(3-nitrophenyl)-2-phenyl-5-pyrimidinylacetate (3.7 g).

mp: 106°–108° C.

IR (Nujol): 1733, 1535 cm$^{-1}$.

NMR (CDCl$_3$, $\delta$): 1.27 (3H, t, J=7 Hz), 2.67 (3H, s), 3.64 (2H, s), 4.21 (2H, q, J=7 Hz), 7.3–7.5 (3H, m), 7.60 (1H, dd, J=8 Hz, 8 Hz), 7.92 (1H, ddd, J=8 Hz, 2 Hz, 2 Hz), 8.15–8.6 (4H, m).

Mass (M/Z): 377.

EXAMPLE 42

A mixture of methyl 6-methyl-4-(2-chloro-5-nitrophenyl)-2-phenyl-5-pyrimidinecarboxylate (0.5 g) and N-methylpiperazine (0.65 g) in N,N-dimethylformamide (5 ml) was stirred at 100° C. for 1.5 hours. The reaction mixture was evaporated and extracted with ethyl acetate (30 ml). The extract was washed with water (20 ml×3) and dried over magnesium sulfate. The solvent was distilled off to give a crystalline residue, which was recrystallized from a mixture of ethyl acetate and diisopropyl ether to afford methyl 6-methyl-4-[2-(4-methylpyperazin-1-yl)-5-nitrophenyl]-2-phenyl-5-pyrimidinecarboxylate (0.3 g).

mp: 204°–205° C.

IR (Nujol): 1725, 1610, 1585, 1540, 1520 cm$^{-1}$.

NMR (DMSO-$d_6$, $\delta$): 2.11 (3H, s), 2.15–2.36 (4H, m), 2.73 (3H, s), 2.80–3.0 (4H, m), 3.56 (3H, s), 7.23 (1H, d, J=9 Hz), 7.4–7.65 (3H, m), 8.17 (1H, d, J=3 Hz), 8.27 (1H, dd, J=3, 9 Hz), 8.4–8.6 (2H, m).

Mass: 447.

EXAMPLE 43

A mixture of ethyl 6-methyl-4-(2-methylthio-5-nitrophenyl)-2-(3-pyridyl)-5-pyrimidinecarboxylate (1 g) and methyl iodide (0.46 ml) in ethyl acetate (2 ml) was stand for 2 days at room temperature. The reaction mixture was evaporated and the residue was recrystallized from a mixture of ethyl alcohol and tetrahydrofuran to afford ethyl 6-methyl-4-(2-methylthio-5-nitrophenyl)-2-[3-(1-melthyl)pyridinium]-5-pyrimidinecarboxylate iodide.

mp: 176°–178° C.

IR (Nujol): 1710, 1640, 1602, 1580, 1540, 1512 cm$^{-1}$.

NMR (CDCl$_3$, $\delta$): 1.1 (3H, t, J=7 Hz), 2.55 (3H, s), 2.83 (3H, s), 4.23 (2H, q, J=7 Hz), 4.83 (3H, s), 7.45 (1H, d, J=9 Hz), 8.12 (1H, d, J=3 Hz), 8.3 (1H, dd, J=3, 9 Hz), 8.2–8.4 (1H, m), 9.3–9.9 (3H, m).

EXAMPLE 44

A mixture of N-(2-dimethylaminoethyl)-2-(5-nitrothienylidene)acetoacetamide (2.1 g), n-butanol (30 ml), triethylamine (0.68 g), benzamidine by hydrochloride (1.06 g) was refluxed for 1.5 hours. After evaporating the solvent, the residue was dissolved in a suspension of water (100 ml) and chloroform (100 ml). The separated organic layer was evaporated in vacuo. The residue was subjected to column chromatography on alumina (100 g) and eluted with chloroform. The fractions containing the object compound were combined and concentrated under reduced pressure. The residue and fumaric acid (0.06 g) was dissolved in ethanol. The separated crystal was filtered and dried in vacuo to give N-(2-dimethylaminoethyl)-6-methyl-4-(5-nitrothiophen-2-yl)-2-phenyl-5-pyrimidinecarboxamide fumarate (0.06 g).

mp: 205°–206° C.

IR (Nujol): 1705, 1660, 1335 cm$^{-1}$.

NMR (CDCl$_3$, $\delta$): 2.37 (6H, s), 2.59 (3H, s), 2.67 (2H, t, J=6 Hz), 3.52 (2H, t, d, J=6 Hz, 6 Hz), 6.52 (2H, s), 7.45–7.7 (3H, m), 7.75 (1H, d, J=5 Hz), 8.11 (1H, d, J=5 Hz), 8.25–8.55 (2H, m), 9.08 (1H, t, J=6 Hz)

EXAMPLE 45

The following compounds are prepared according to the similar manner to that of Example 44.

(1) 6-Methyl-4-(3-nitrophenyl)-2-phenyl-5-pyrimidinecarboxamide.

mp: 231°–232° C.

IR (Nujol): 3325, 1665 cm$^{-1}$.

NMR (DMSO-$d_6$, $\delta$): 2.67 (3H, s), 7.3–8.8 (11H, m).

Mass: 334 (M+).

(2) Ethyl 6-methyl-4-(3-nitrophenyl)-2-(3-pyridyl)-5-pyrimidinecarboxylate.

mp: 63°–64° C.

IR (Nujol): 1735, 1585, 1535 cm$^{-1}$.

NMR (DMSO-$d_6$, $\delta$): 1.1 (3H, t, J=7 Hz), 2.66 (3H, s), 4.26 (2H, q, J=7 Hz), 7.53–8.9 (7H, m), 9.62 (1H, m).

Mass: 364.

(3) 5-Acetyl-4-(4-hydroxy-3-nitrophenyl)-6-methyl-2-phenylpyrimidine.

mp: 154°–155° C.

IR (Nujol): 1695, 1625, 1580 cm$^{-1}$.

NMR (DMSO-$d_6$, $\delta$): 2.27 (3H, s), 2.52 (3H, s), 7.23 (1H, d, J=8 Hz), 7.33–7.63 (3H, m), 7.78 (1H, dd, J=2, 8 Hz), 8.15 (1H, d, J=2 Hz), 8.3–8.5 (2H, m).

Mass: 349.

(4) Ethyl 4-(3-hydroxy-4-nitrophenyl)-6-methyl-2-phenyl-5-pyrimidinecarboxylate.

mp: 109° C.

IR (Nujol): 1725, 1630, 1590, 1382 cm$^{-1}$.

NMR (DMSO-$d_6$, $\delta$): 1.12 (3H, t, J=7 Hz), 2.7 (3H, s), 4.28 (2H, q, J=7 Hz), 7.23 (1H, dd, J=2, 8 Hz), 7.42–7.73 (4H, m), 8.03 (1H, d, J=8 Hz), 8.37–8.63 (2H, m).

Mass: 379.

(5) 5-Acetyl-4-(4-chloro-3-nitrophenyl)-6-methyl-2-phenyl-pyrimidine.

mp: 139°–140° C.

IR (Nujol): 1700, 1605, 1570, 1535, 1240 cm$^{-1}$.

NMR (DMSO-d$_6$, δ): 2.33 (3H, s), 2.6 (3H, s), 7.43–7.67 (3H, m), 7.87–8.0 (2H, m), 8.33–8.57 (3H, m).
Mass: 367, 369.

(6) N-(2-Dimethylaminoethyl)-6-methyl-4-(3-nitrophenyl)-2-phenyl-5-pyrimidinecarboxamide.
mp: 122°–124° C.
IR (Nujol): 1630, 1565, 1530 cm$^{-1}$.

(7) N-(2-Diethylaminoethyl)-6-methyl-4-(3-nitrophenyl)-2-phenyl-5-pyrimidinecarboxamide.
mp: 109°–111° C.
IR (Nujol): 3200, 1625, 1530 cm$^{-1}$.

(8) N-(3-Dimethylaminopropyl)-6-methyl-4-(3-nitrophenyl)-2-phenyl-5-pyrimidinecarboxamide.
mp: 137°–139° C.
IR (Nujol): 1630, 1565, 1530 cm$^{-1}$.

(9) N-[2-(1-Pyrrolidinyl)ethyl]-6-methyl-4-(3-nitrophenyl)-2-phenyl-5-pyrimidinecarboxamide.
mp: 133° C.
IR (Nujol): 1630, 1565, 1530 cm$^{-1}$.

(10) N-[(1-Ethyl-2-pyrrolidinyl)methyl]-6-methyl-4-(3-nitrophenyl)-2-phenyl-5-pyrimidinecarboxamide.
mp: 88°–90° C.
IR (Nujol): 1630, 1565, 1530 cm$^{-1}$.

(11) N-(2-Dimethylaminoethyl)-6-methyl-4-(4-nitrophenyl)-2-phenyl-5-pyrimidinecarboxamide.
mp: 148°–149° C.
IR (Nujol): 3260, 1640 cm$^{-1}$.

(12) 6-Methyl-4-(4-nitrophenyl)-2-phenyl-5-pyrimidinecarboxylic acid.
mp: 247°–248° C. (dec.).
IR (Nujol): 1690, 1608, 1355 cm$^{-1}$.

(13) Ethyl 6-methyl-4-(2-methylsulfonyl-5-nitrophenyl)-2-phenyl-5-pyrimidinecarboxylate.
mp: 150°–151° C.
IR (Nujol): 1730, 1535, 1155 cm$^{-1}$.

(14) 6-Methyl-4-(3-nitrophenyl)-2-phenyl-5-pyrimidinecarbonitrile.
mp: 185°–187° C.
IR (Nujol): 2230, 1525, 1350 cm$^{-1}$.

(15) N-(2-Dimethylaminoethyl)-6-methyl-4-(3-nitrophenyl)-2-phenyl-5-pyrimidinecarboxamide fumarate.
mp: 200°–201° C.
IR (KBr): 1640, 1530 cm$^{-1}$.

(16) Ethyl 6-methyl-4-[2-(4-nitrobenzyloxy)-phenyl]-2-phenyl-5-pyrimidinecarboxylate.
mp: 113°–114° C.
IR (Nujol): 1732, 1601, 1540, 1520.
NMR (DMSO-d$_6$, δ): 0.88 (3H, t, J=7 Hz), 2.7 (3H, s), 4.03 (2H, q, J=7 Hz), 5.25 (2H, s), 6.93–7.65 (9H, m), 7.9–8.55 (4H, m)
Mass: 469.

(17) 6-Methyl-4-(3-nitrophenyl)-N-[2-(1-morpholino)ethyl]-2-phenyl-5-pyrimidinecarboxamide.
mp: 165°–167° C.
IR (Nujol): 3400, 1625, 1565, 1530, 1350 cm$^{-1}$.

(18) N-(2-Acetylaminoethyl)-6-methyl-4-(3-nitrophenyl)-2-phenyl-5-pyrimidinecarboxamide.
mp: 199°–201° C.
IR (Nujol): 3300, 1640, 1590, 1540 cm$^{-1}$.

(19) 6-Methyl-5-(4-methylpiperazin-1-ylcarbonyl)-4-(3-nitrophenyl)-2-phenylpyrimidine.
mp: 153°–155° C.
IR (Nujol): 1634, 1530, 1345 cm$^{-1}$.

(20) 6-Methyl-5-(4-methylpiperazin-1-ylcarbonyl)-4-(3-nitrophenyl)-2-phenylpyrimidine fumarate.
mp: 245°–246° C.
IR (Nujol): 1715, 1645, 1530 cm$^{-1}$.

(21) N-[3-(1-Ethyl)piperidinyl]-6-methyl-4-(3-nitrophenyl)-2-phenyl-5-pyrimidinecarboxamide
mp: 146°–148° C.
IR (Nujol): 3290, 1635, 1525, 1350 cm$^{-1}$.

(22) N-(2-Trimethylammonioethyl)-6-methyl-4-(3-nitrophenyl)-2-phenyl-5-pyrimidinecarboxamide iodide.
mp: 228°–230° C.
IR (Nujol): 3390, 1670, 1585, 1525, 1350 cm$^{-1}$.

(23) 5-[3-(1-Ethylpiperidin-3-yl)ureido]-6-methyl-4-(3-nitrophenyl)-2-phenylpyrimidine.
mp: 206°–208° C.
IR (Nujol): 1625, 1575, 1530, 1352 cm$^{-1}$.

(24) 6-Methyl-5-[(4-methylpiperazin-1-yl)-carbonylamino]-4-(3-nitrophenyl)-2-phenylpyrimidine.
mp: 221°–223° C.
IR (Nujol): 3300, 1630, 1555, 1530, 1350 cm$^{-1}$.

(25) N-(2-Hydroxyethyl)-6-methyl-4-(3-nitrophenyl)-2-phenyl-5-pyrimidinecarboxamide.
mp: 190°–192° C.
IR (Nujol): 3300, 1630, 1550, 1520, 1355 cm$^{-1}$.
NMR (DMSO-d$_6$, δ): 2.65 (3H, s), 3.3–3.5 (4H, m), 4.5–4.75 (1H, m), 7.50–8.0 (4H, m), 8.3–8.85 (6H, m).

(26) N-(2-Chloroethyl)-6-methyl-4-(3-nitrophenyl)-2-phenyl-5-pyrimidinecarboxamide.
mp: 199°–200° C.
IR (Nujol): 3300, 1640, 1590, 1530 cm$^{-1}$.

(27) 6-Methyl-4-(3-nitrophenyl)-2-phenyl-N-[2-(4-thiomorpholino)ethyl]-5-pyrimidinecarboxamide
mp: 168°–169° C.
IR (Nujol): 3210, 1620, 1565, 1530, 1350 cm$^{-1}$.

(28) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.

(29) 5-Hydroxymethyl-6-methyl-2-phenyl-4-(3-nitrophenyl)pyrimidine.
mp: 177°–178° C.
IR (Nujol): 1590, 1360, 1025 cm$^{-1}$.

(30) 5-Bromomethyl-6-methyl-2-phenyl-4-(3-nitrophenyl)pyrimidine.
mp: 163°–164° C.
IR (Nujol): 1550, 1530, 1350 cm$^{-1}$.

(31) 5-Cyanomethyl-6-methyl-2-phenyl-4-(3-nitrophenyl)pyrimidine.
mp: 219°–221° C.
IR (Nujol): 1535, 1350 cm$^{-1}$.

(32) Ethyl 6-methyl-4-(3-nitrophenyl)-2-phenyl-5-pyrimidinylacetate.
mp: 106°–108° C.
IR (Nujol): 1733, 1535 cm$^{-1}$.

(33) 6-Methyl-4-(3-nitrophenyl)-2-phenyl-5-pyrimidinylacetic acid.
mp: 222°–224° C. (dec.).
IR (Nujol): 1700, 1530 cm$^{-1}$.

(34) N-(2-Dimethylaminoethyl)-[6-methyl-4-(3-nitrophenyl)-2-phenyl-5-pyrimidinyl]acetoamide.
mp: 185°–187° C.
IR (Nujol): 3300, 1650, 1530 cm$^{-1}$.

(35) Methyl 6-ethyl-4-(3-nitrophenyl)-2-phenyl-5-pyrimidinecarboxylate.
mp: 107°–110° C.
IR (Nujol): 2950, 1725, 1541 cm$^{-1}$.

NMR (DMSO-d$_6$, δ): 1.41 (3H, t, J=7 Hz), 2.97 (2H, q, J=7 Hz), 3.83 (3H, s), 7.43-7.80 (3H, m), 7.80-8.66 (6, m).
Mass: 363.

(36) 6-Ethyl-4-(3-nitrophenyl)-2-phenyl-5-pyrimidinecarboxylic acid.
mp: 184°-185° C.
IR (Nujol): 1720, 1540, 1350 cm$^{-1}$.

(37) N-(2-Dimethylaminoethyl)-6-ethyl-4-(3-nitrophenyl)-2-phenyl-5-pyrimidinecarboxamide.
mp: 106°-109° C.
IR (Nujol): 3200, 1630, 1530, 1350.

(38) 4-(3-Nitrophenyl)-2-phenyl-6-trifluoromethyl-5-pyrimidinecarboxylic acid.
mp: 313°-315° C. (dec.).
IR (Nujol): 1615, 1530 cm$^{-1}$.

(39) N-(2-Dimethylaminoethyl)-4-(3-nitrophenyl)-2-phenyl-6-trifluoromethyl-5-pyrimidinecarboxyamide.
mp: 174°-175° C.
IR (Nujol): 3300, 1645, 1575, 1541, 1540, 1355 cm$^{-1}$.

(40) Methyl 6-methyl-4-[2-(4-methylpiperazin-1-yl)-5-nitrophenyl]-2-phenyl-5-pyrimidinecarboxylate.
mp: 204°-205° C.
IR (Nujol): 1725, 1610, 1585, 1540, 1520 cm$^{-1}$.

(41) Ethyl 4-(2-chloro-5-nitrophenyl)-6-methyl-2-(3-pyridyl)-5-pyrimidinecarboxylate.
mp: 160°-162° C.
NMR (DMSO-d$_6$, δ): 0.93 (3H, t, J=7 Hz), 2.76 (3H, s), 4.11 (2H, q, J=7 Hz), 7.47-8.03 (2H, m), 8.25-8.90 (4H, m), 9.5 (1H, m)
Mass M/Z: 398,400.

(42) Ethyl 6-methyl-4-(2-methylthio-5-nitrophenyl)-2-(3-pyridyl)-5-pyrimidinecarboxylate.
mp: 94°-97° C.
IR (Nujol): 1730, 1602, 1580, 1525, 1340 cm$^{-1}$.

(43) Ethyl 6-methyl-4-(2-methylthio-5-nitrophenyl)-2-[3-(1-methyl)pyridinium]-5-pyrimidinecarboxylate iodide
mp: 176°-178° C.
IR (Nujol): 1710, 1640, 1602, 1580, 1540, 1512 cm$^{-1}$.

(44) 6-Methyl-4-(2-methylthio-5-nitrophenyl)-2-phenyl-5-pyrimidinecarboxylic acid.
mp: 200°-203° C.
IR (Nujol): 1735, 1695, 1605, 1585, 1520 cm$^{-1}$.

(45) N-(2-Dimethylaminoethyl)-6-methyl-4-(2-methylthio-5-nitrophenyl)-2-phenyl-5-pyrimidinecarboxamide
mp: 166°-168° C.
IR (Nujol): 1665, 1600, 1575 cm$^{-1}$.

(46) Methyl 6-methyl-4-(2-methylthio-5-nitrophenyl)-2-phenyl-5-pyrimidinecarboxylate.
mp: 171°-173° C.
IR (Nujol): 1730, 1602, 1578, 1542, 1515 cm$^{-1}$.

(47) 5-[3-(2-Dimethylaminoethyl)ureido]-b 6-methyl-4-(2-methylthio-5-nitrophenyl)-2-phenylpyrimidine.
mp: 190°-192° C.
IR (Nujol): 3350, 3250, 1625, 1520, 1340 cm$^{-1}$.

(48) N-(2-Dimethylaminoethyl)-6-methyl-4-(4-nitrophenyl)-2-phenyl-5-pyrimidinecarboxamide fumarate.
mp: 188°-190° C.
IR (Nujol): 1715, 1665, 1638, 1585, 1545, 1520 cm$^{-1}$.

(49) 4-(4-Nitrophenyl)-2-phenyl-5-pyrimidinecarboxylic acid.
mp: 253°-255° C.
IR (Nujol): 1701, 1565, 1525, 1355 cm$^{-1}$.

(50) N-(2-Dimethylaminoethyl)-4-(4-nitrophenyl)-2-phenyl-5-pyrimidinecarboxamide.
mp: 180°-182° C.
IR (Nujol): 3300, 1640, 1565, 1535, 1520, 1355 cm$^{-1}$.

(51) 5-(4-Methylpiperazin-1-ylcarbonyl)-4-(4-nitrophenyl)-2-phenylpyrimidine.
mp: 165°-166° C.
IR (Nujol): 1630, 1570, 1535, 1355 cm$^{-1}$.

(52) 5-Formyl-6-methyl-4-(3-nitrophenyl)-2-phenyl-5-pyrimidine.
mp: 154°-155° C.
IR (Nujol): 1700, 1535 cm$^{-1}$.

(53) N-(2-Dimethylaminoethyl)-6-methyl-4-(5-nitrothiophen-2-yl)-2-phenyl-5-pyrimidinecarboxamide fumarate.
mp: 205°-206° C.
IR (Nujol): 1705, 1660, 1335 cm$^{-1}$.

(54) Ethyl 4-(4-nitrophenyl)-2-phenyl-5-pyrimidinecarboxylate.
mp: 138°-140° C.
IR (Nujol): 1731, 1570, 1530, 1355, 1295 cm$^{-1}$.

(55) Ethyl 4-(3-nitrophenyl)-2-phenyl-6-trifluoromethyl-5-pyrimidinecarboxylate.
mp: 93°-95° C.
IR (Nujol): 1730, 1590, 1568, 1545, 1215, 1148 cm$^{-1}$.
NMR (DMSO-d$_6$, δ): 1.16 (3H, t, J=7 Hz), 4.31 (2H, q, J=7 Hz), 7.5-7.73 (3H, s), 7.80-8.60 (6H, m).
Mass: 417.

(56) Methyl 4-(2-chloro-5-nitrophenyl)-6-methyl-2-phenyl-5-pyrimidinecarboxylate.
mp: 171°-174° C.
IR (Nujol): 1725, 1550, 1535, 1350, 1285 cm$^{-1}$.
NMR (DMSO-d$_6$, δ): 2.77 (3H, s), 3.65 (3H, s), 7.4-8.55 (8H, m)
Mass (M/Z): 383, 385 (M$^+$).

(57) 6-Methyl-5-(4-methylpiperazin-1-ylcarbonyl)-2-phenyl-4-(3-trifluoromethylphenyl)pyrimidine.
mp: 124°-125° C.
IR (Nujol): 1628, 1545, 1535 cm$^{-1}$.
NMR (CDCl$_3$, δ): 1.2-1.9 (2H, m), 2.0-2.5 (2H, m), 2.1 (3H, s), 2.6 (3H, s), 2.66-3.3 (2H, m), 3.66 (2H, t, J=6 Hz), 7.3-7.8 (5H, m), 7.9-8.6 (4H, m).
Mass (M/Z): 440 (M$^+$).

(58) Methyl 6-methyl-4-(3-hydroxyphenyl)-2-phenyl-5-pyrimidinecarboxylate.

(59) Methyl 2-(4-chlorophenyl)-6-methyl-4-(3-nitrophenyl)-5-pyrimidinecarboxylate.
mp: 105°-107° C.
IR (Nujol): 1725, 1530, 1350 cm$^{-1}$.
NMR (CDCl$_3$, δ): 2.68 (3H, s), 3.8 (3H, s), 7.4, 8.47 (total 4H, ABq, J=9 Hz), 7.6-8.65 (4H, m).
Mass (M/Z): 383, 385 (M$^+$).

(60) Ethyl 6-diethoxymethyl-4-(3-nitrophenyl)-2-phenyl-5-pyrimidinecarboxylate.
mp: 84°-86° C.
IR (Nujol): 1730, 1535, 1355 cm$^{-1}$.
NMR (DMSO-d$_6$, δ): 1.13 (3H, t, J=7 Hz), 1.23 (6H, t, J=7 Hz), 3.69 (2H, q, J=7 Hz), 3.74 (2H, q, J=7 Hz), 4.20 (2H, q, J=7 Hz), 5.70 (1H, s), 7.45-7.65 (3H, m), 7.84 (1H, dd, J=9 Hz, 9 Hz), 8.15 (1H, ddd, J=9 Hz, 2 Hz, 2 Hz), 8.3-8.6 (4H, m).

(61) 6-Methyl-5-(4-methylpiperazin-1-ylcarbonyl)-4-(2-nitrophenyl)-2-phenylpyrimidine.
mp: 114°-115° C.
IR (Nujol): 1620, 1545, 1525, 1360 cm$^{-1}$.
NMR (CDCl$_3$, δ): 1.4-2.0 (2H, m), 2.1 (3H, s), 2.1-2.5 (2H, m), 2.65 (3H, s), 3.25 (2H, t, J=6 Hz), 3.4-3.9 (2H, m), 7.3-7.5 (3H, m) 7.5-8.0 (4H, m), 8.2-8.4 (2H, m).
Mass (M/Z): 417 (M$^+$).

(62) 6-Methyl-5-(4-methylpiperazin-1-ylcarbonyl)-4-(4-nitrophenyl)-2-phenylpyrimidine.
mp: 257°–258° C.
IR (Nujol): 1632, 1530, 1350, 1295, 1270 cm$^{-1}$.
NMR (CDCl$_3$, δ): 1.4–1.9 (2H, m), 2.0–2.4 (2H, m), 2.13 (3H, s), 2.65 (3H, s), 2.7–3.2 (2H, m), 3.7 (2H, q, J=5 Hz), 7.3–7.6 (3H, m), 8.03–8.33 (total 4H, ABq, J=9 Hz), 8.4–8.6 (2H, m).
Mass (M/Z): 417 (M+).

EXAMPLE 46

A mixture of ethyl 2-(4-nitrobenzoyl)-3-dimethylaminopropenoate (3 g), benzamidine hydrochloride (1.93 g) and triethylamine (2 ml) in n-butyl alcohol (30 ml) was refluxed for 30 min. The reaction mixture was poured into water (300 ml) and the precipitate was collected by filtration. The residue was recrystallized with diethyl ether to afford ethyl 4-(4-nitrophenyl)-2-phenyl-5-pyrimidinecarboxylate (3.1 g).
mp: 138°–140° C.
IR (Nujol): 1731, 1570, 1530, 1355, 1295 cm$^{-1}$.
NMR (DMSO-d$_6$, δ): 1.15 (3H, t, J=7 Hz), 4.2 (2H, q, J=7 Hz), 7.45–8.15 (5H, m), 8.2–8.7 (4H, m), 9.35 (1H, s).
Mass (M/Z): 349 (M+).

EXAMPLE 47

The following compounds are prepared according to the similar manner to that of Example 46.
(1) 6-Methyl-4-(3-nitrophenyl)-2-phenyl-5-pyrimidinecarboxamide.
mp: 231°–232° C.
IR (Nujol): 3325, 1665 cm$^{-1}$.
NMR (DMSO-d$_6$, δ): 2.67 (3H, s), 7.3–8.8 (11H, m).
Mass: 334 (M+).
(2) Ethyl 6-methyl-4-(3-nitrophenyl)-2-(3-pyridyl)-5-pyrimidinecarboxylate.
mp: 63°–64° C.
IR (Nujol): 1735, 1585, 1535 cm$^{-1}$.
NMR (DMSO-d$_6$, δ): 1.1 (3H, t, J=7 Hz), 2.66 (3H, s), 4.26 (2H, q, J=7 Hz), 7.53–8.9 (7H, m), 9.62 (1H, m).
Mass: 364.
(3) 5-Acetyl-4-(4-hydroxy-3-nitrophenyl)-6-methyl-2-phenylpyrimidine.
mp: 154°–155° C.
IR (Nujol): 1695, 1625, 1580 cm$^{-1}$.
NMR (DMSO-d$_6$, δ): 2.27 (3H, s), 2.52 (3H, s), 7.23 (1H, d, J=8 Hz), 7.33–7.63 (3H, m), 7.78 (1H, dd, J=2, 8 Hz), 8.15 (1H, d, J=2 Hz), 8.3–8.5 (2H, m).
Mass: 349.
(4) Ethyl 4-(3-hydroxy-4-nitrophenyl)-6-methyl-2-phenyl-5-pyrimidinecarboxylate.
mp: 109° C.
IR (Nujol): 1725, 1630, 1590, 1382 cm$^{-1}$.
NMR (DMSO-d$_6$, δ): 1.12 (3H, t, J=7 Hz), 2.7 (3H, s), 4.28 (2H, q, J=7 Hz), 7.23 (1H, dd, J=2, 8 Hz), 7.42–7.73 (4H, m), 8.03 (1H, d, J=8 Hz), 8.37–8.63 (2H, m).
Mass: 379.
(5) 5-Acetyl-4-(4-chloro-3-nitrophenyl)-6-methyl-2-phenyl-pyrimidine.
mp: 139°–140° C.
IR (Nujol): 1700, 1605, 1570, 1535, 1240 cm$^{-1}$.
NMR (DMSO-d$_6$, δ): 2.33 (3H, s), 2.6 (3H, s), 7.43–7.67 (3H, m), 7.87–8.0 (2H, m), 8.33–8.57 (3H, m).
Mass: 367, 369.
(6) N-(2-Dimethylaminoethyl)-6-methyl-4-(3-nitrophenyl)-2-phenyl-5-pyrimidinecarboxamide.
mp: 122°–124° C.
IR (Nujol): 1630, 1565, 1530 cm$^{-1}$.
(7) N-(2-Diethylaminoethyl)-6-methyl-4-(3-nitrophenyl)-2-phenyl-5-pyrimidinecarboxamide.
mp: 109°–111° C.
IR (Nujol): 3200, 1625, 1530 cm$^{-1}$.
(8) N-(3-Dimethylaminopropyl)-6-methyl-4-(3-nitrophenyl)-2-phenyl-5-pyrimidinecarboxamide.
mp: 137°–139° C.
IR (Nujol): 1630, 1565, 1530 cm$^{-1}$.
(9) N-[2-(1-Pyrrolidinyl)ethyl]-6-methyl-4-(3-nitrophenyl)-2-phenyl-5-pyrimidinecarboxamide.
mp: 133° C.
IR (Nujol): 1630, 1565, 1530 cm$^{-1}$.
(10) N-[(1-Ethyl-2-pyrrolidinyl)methyl]-6-methyl-4-(3-nitrophenyl)-2-phenyl-5-pyrimidinecarboxamide.
mp: 88°–90° C.
IR (Nujol): 1630, 1565, 1530 cm$^{-1}$.
(11) N-(2-Dimethylaminoethyl)-6-methyl-4-(4-nitrophenyl)-2-phenyl-5-pyrimidinecarboxamide.
mp: 148°–149° C.
IR (Nujol): 3260, 1640 cm$^{-1}$.
(12) 6-Methyl-4-(4-nitrophenyl)-2-phenyl-5-pyrimidinecarboxylic acid.
mp: 247°–248° C. (dec.).
IR (Nujol): 1690, 1608, 1355 cm$^{-1}$.
(13) Ethyl 6-methyl-4-(2-methylsulfonyl-5-nitrophenyl)-2-phenyl-5-pyrimidinecarboxylate.
mp: 150°–151° C.
IR (Nujol): 1730, 1535, 1155 cm$^{-1}$.
(14) 6-Methyl-4-(3-nitrophenyl)-2-phenyl-5-pyrimidinecarbonitrile.
mp: 185°–187° C.
IR (Nujol): 2230, 1525, 1350 cm$^{-1}$.
(15) N-(2-Dimethylaminoethyl)-6-methyl-4-(3-nitrophenyl)-2-phenyl-5-pyrimidinecarboxamide fumarate.
mp: 200°–201° C.
IR (KBr): 1640, 1530 cm$^{-1}$.
(16) Ethyl 6-methyl-4-[2-(4-nitrobenzyloxy)phenyl]-2-phenyl-5-pyrimidinecarboxylate.
mp: 113°–114° C.
IR (Nujol): 1732, 1601, 1540, 1520.
NMR (DMSO-d$_6$, δ): 0.88 (3H, t, J=7 Hz), 2.7 (3H, s), 4.03 (2H, q, J=7 Hz), 5.25 (2H, s), 6.93–7.65 (9H, m), 7.9–8.55 (4H, m).
Mass: 469.
(17) 6-Methyl-4-(3-nitrophenyl)-N-[2-(1-morpholino)ethyl]-2-phenyl-5-pyrimidinecarboxamide.
mp: 165°–167° C.
IR (Nujol): 3400, 1625, 1565, 1530, 1350 cm$^{-1}$.
(18) N-(2-Acetylaminoethyl)-6-methyl-4-(3-nitrophenyl)-2-phenyl-5-pyrimidinecarboxamide.
mp: 199°–201° C.
IR (Nujol): 3300, 1640, 1590, 1540 cm$^{-1}$.
(19) 6-Methyl-5-(4-methylpiperazin-1-ylcarbonyl)-4-(3-nitrophenyl)-2-phenylpyrimidine.
mp: 153°–155° C.
IR (Nujol): 1634, 1530, 1345 cm$^{-1}$.
(20) 6-Methyl-5-(4-methylpiperazin-1-ylcarbonyl)-4-(3-nitrophenyl)-2-phenylpyrimidine fumarate.
mp: 245°–246° C.
IR (Nujol): 1715, 1645, 1530 cm$^{-1}$.
(21) N-[3-(1-Ethyl)piperidinyl]-6-methyl-4-(3-nitrophenyl)-2-phenyl-5-pyrimidinecarboxamide.
mp: 146°–148° C.

IR (Nujol): 3290, 1635, 1525, 1350 cm$^{-1}$.
(22) N-(2-Trimethylammonioethyl)-6-methyl-4-(3-nitrophenyl)-2-phenyl-5-pyrimidinecarboxamide iodide.
mp: 228°–230° C.
IR (Nujol): 3390, 1670, 1585, 1525, 1350 cm$^{-1}$.
(23) 5-[3-(1-Ethylpiperidin-3-yl)ureido]-6-methyl-4-(3-nitrophenyl)-2-phenylpyrimidine.
mp: 206°–208° C.
IR (Nujol): 1625, 1575, 1530, 1352 cm$^{-1}$.
(24) 6-Methyl-5-[(4-methylpiperazin-1-yl)-carbonylamino]-4-(3-nitrophenyl)-2-phenylpyrimidine.
mp: 221°–223° C.
IR (Nujol): 3300, 1630, 1555, 1530, 1350 cm$^{-1}$.
(25) N-(2-Hydroxyethyl)-6-methyl-4-(3-nitrophenyl)-2-phenyl-5-pyrimidinecarboxamide.
mp: 190°–192° C.
IR (Nujol): 3300, 1630, 1550, 1520, 1355 cm$^{-1}$.
NMR (DMSO-d$_6$, δ): 2.65 (3H, s), 3.3–3.5 (4H, m), 4.5–4.75 (1H, m), 7.50–8.0 (4H, m), 8.3–8.85 (6H, m).
(26) N-(2-Chloroethyl)-6-methyl-4-(3-nitrophenyl)-2-phenyl-5-pyrimidinecarboxamide.
mp: 199°–200° C.
IR (Nujol): 3300, 1640, 1590, 1530 cm$^{-1}$.
(27) 6-Methyl-4-(3-nitrophenyl)-2-phenyl-N-[2-(4-thiomorpholino)ethyl]-5-pyrimidinecarboxamide
mp: 168°–169° C.
IR (Nujol): 3210, 1620, 1565, 1530, 1350 cm$^{-1}$.
(28) 6-Methyl-4-(3-nitrophenyl)-2-phenyl-N-[2-(4-thiomorpholino)ethyl]-5-pyrimidinecarboxamide fumarate.
mp: 193°–195° C.
IR (Nujol): 3300, 1670, 1585, 1540 cm$^{-1}$.
(29) 5-Hydroxymethyl-6-methyl-2-phenyl-4-(3-nitrophenyl)pyrimidine.
mp: 177°–178° C.
IR (Nujol): 1590, 1360, 1025 cm$^{-1}$.
(30) 5-Bromomethyl-6-methyl-2-phenyl-4-(3-nitropenyl)pyrimidine.
mp: 163°–164° C.
IR (Nujol): 1550, 1530, 1350 cm$^{-1}$.
(31) 5-Cyanomethyl-6-methyl-2-phenyl-4-(3-nitrophenyl)pyrimidine.
mp: 219°–221° C.
IR (Nujol): 1535, 1350 cm$^{-1}$.
(32) Ethyl 6-methyl-4-(3-nitrophenyl)-2-phenyl-5-pyrimidinylacetate.
mp: 106°–108° C.
IR (Nujol): 1733, 1535 cm$^{-1}$.
(33) 6-Methyl-4-(3-nitrophenyl)-2-phenyl-5-pyrimidinylacetic acid.
mp: 222°–224° C. (dec.).
IR (Nujol): 1700, 1530 cm$^{-1}$.
(34) N-(2-Dimethylaminoethyl)-[6-methyl-4-(3-nitrophenyl)-2-phenyl-5-pyrimidinyl]acetoamide.
mp: 185°–187° C.
IR (Nujol): 3300, 1650, 1530 cm$^-$.
(35) Methyl 6-ethyl-4-(3-nitrophenyl)-2-phenyl-5-pyrimidinecarboxylate.
mp: 107°–110° C.
IR (Nujol): 2950, 1725, 1541 cm$^{-1}$.
NMR (DMSO-d$_6$, δ): 1.41 (3H, t, J=7 Hz), 2.97 (2H, q, J=7 Hz), 3.83 (3H, s), 7.43–7.80 (3H, m), 7.80–8.66 (6H, m).
Mass: 363.
(36) 6-Ethyl-4-(3-nitrophenyl)-2-phenyl-5-pyrimidinecarboxylic acid.
mp: 184°–185° C.
IR (Nujol): 1720, 1540, 1350 cm$^{-1}$.
(37) N-(2-Dimethylaminoethyl)-6-ethyl-4-(3-nitrophenyl)-2-phenyl-5-pyrimidinecarboxamide.
mp: 106°–109° C.
IR (Nujol): 3200, 1630, 1530, 1350.
(38) 4-(3-Nitrophenyl)-2-phenyl-6-trifluoromethyl-5-pyrimidinecarboxylic acid.
mp: 313°–315° C. (dec.).
IR (Nujol): 1615, 1530 cm$^{-1}$.
(39) N-(2-Dimethylaminoethyl)-4-(3-nitrophenyl)-2-phenyl-6-trifluoromethyl-5-pyrimidinecarboxamide.
mp: 174°–175° C.
IR (Nujol): 3300, 1645, 1575, 1541, 1540, 1355 cm$^{-1}$.
(40) Methyl 6-methyl-4-[2-(4-methylpiperazin-1-yl)-5-nitrophenyl]-2-phenyl-5-pyrimidinecarboxylate.
mp: 204°–205° C.
IR (Nujol): 1725, 1610, 1585, 1540, 1520 cm$^{-1}$.
(41) Ethyl 4-(2-chloro-5-nitrophenyl)-6-methyl-2-(3-pyridyl)-5-pyrimidinecarboxylate.
mp: 160°–162° C.
NMR (DMSO-d$_6$, δ): 0.93 (3H, t, J=7 Hz), 2.76 (3H, s), 4.11 (2H, q, J=7 Hz), 7.47–8.03 (2H, m), 8.25–8.90 (4H, m), 9.5 (1H, m).
Mass M/Z: 398, 400.
(42) Ethyl 6-methyl-4-(2-methylthio-5-nitrophenyl)-2-(3-pyridyl)-5-pyrimidinecarboxylate.
mp: 94°–97° C.
IR (Nujol): 1730, 1602, 1580, 1525, 1340 cm$^{-1}$.
(43) Ethyl 6-methyl-4-(2-methylthio-5-nitrophenyl)-2-[3-(1-methyl)pyridinium]-5-pyrimidinecarboxylate iodide.
mp: 176°–178° C.
IR (Nujol): 1710, 1640, 1602, 1580, 1540, 1512 cm$^{-1}$.
(44) 6-Methyl-4-(2-methylthio-5-nitrophenyl)-2-phenyl-5-pyrimidinecarboxylic acid.
mp: 200°–203° C.
IR (Nujol): 1735, 1695, 1605, 1585, 1520 cm$^{-1}$.
(45) N-(2-Dimethylaminoethyl)-6-methyl-4-(2-methylthio-5-nitrophenyl)-2-phenyl-5-pyrimidinecarboxamide.
mp: 166°–168° C.
IR (Nujol): 1665, 1600, 1575 cm$^{-1}$.
(46) Methyl 6-methyl-4-(2-methylthio-5-nitrophenyl)-2-phenyl-5-pyrimidinecarboxylate.
mp: 171°–173° C.
IR (Nujol): 1730, 1602, 1578, 1542, 1515 cm$^{-1}$.
(47) 5-[3-(2-Dimethylaminoethyl)ureido]-6-methyl-4-(2-methylthio-5-nitrophenyl)-2-phenylpyrimidine.
mp: 190°–192° C.
IR (Nujol): 3350, 3250, 1625, 1520, 1340 cm$^{-1}$.
(48) N-(2-Dimethylaminoethyl)-6-methyl-4-(4-nitrophenyl)-2-phenyl-5-pyrimidinecarboxamide fumarate.
mp: 188°–190° C.
IR (Nujol): 1715, 1665, 1638, 1585, 1545, 1520 cm$^{-1}$.
(49) 4-(4-Nitrophenyl)-2-phenyl-5-pyrimidinecarboxylic acid.
mp: 253°–255° C.
IR (Nujol): 1701, 1565, 1525, 1355 cm$^{-1}$.
(50) N-(2-Dimethylaminoethyl)-4-(4-nitrophenyl)-2-phenyl-5-pyrimidinecarboxamide.
mp: 180°–182° C.
IR (Nujol): 3300, 1640, 1565, 1535, 1520, 1355 cm$^{-1}$.
(51) 5-(4-Methylpiperazin-1-ylcarbonyl)-4-(4-nitrophenyl)-2-phenylpyrimidine.
mp: 165°–166° C.

IR (Nujol): 1630, 1570, 1535, 1355 cm$^{-1}$.
(52) 5-Formyl-6-methyl-4-(3-nitrophenyl)-2-phenyl-5-pyrimidine.
mp: 154°-155° C.
IR (Nujol): 1700, 1535 cm$^{-1}$.
(53) N-(2-Dimethylaminoethyl)-6-methyl-4-(5-nitrothiophen-2-yl)-2-phenyl-5-pyrimidinecarboxamide fumarate.
mp: 205°-206° C.
IR (Nujol): 1705, 1660, 1335 cm$^{-1}$.
(54) Ethyl 4-(4-nitrophenyl)-2-phenyl-5-pyrimidinecarboxylate.
mp: 138°-140° C.
IR (Nujol): 1731, 1570, 1530, 1355, 1295 cm$^{-1}$.
(55) Ethyl 4-(3-nitrophenyl)-2-phenyl-6-trifluoromethyl-5-pyrimidinecarboxylate.
mp: 93°-95° C.
IR (Nujol): 1730, 1590, 1568, 1545, 1215, 1148 cm$^{-1}$.
NMR (DMSO-d$_6$, δ): 1.16 (3H, t, J=7 Hz), 4.31 (2H, q, J=7 Hz), 7.5-7.73 (3H, s), 7.80-8.60 (6H, m).
Mass: 417.
(56) Methyl 4-(2-chloro-5-nitrophenyl)-6-methyl-2-phenyl-5-pyrimidinecarboxylate.
mp: 171°-174° C.
IR (Nujol): 1725, 1550, 1535, 1350, 1285 cm$^{-1}$.
NMR (DMSO-d$_6$, δ): 2.77 (3H, s), 3.65 (3H, s), 7.4-8.55 (8H, m).
Mass (M/Z): 383, 385 (M+).
(57) 6-Methyl-5-(4-methylpiperazin-1-ylcarbonyl)-2-phenyl-4-(3-trifluoromethylphenyl)pyrimidine.
mp: 124°-125° C.
IR (Nujol): 1628, 1545, 1535 cm$^{-1}$.
NMR (CDCl$_3$, δ): 1.2-1.9 (2H, m), 2.0-2.5 (2H, m), 2.1 (3H, s), 2.6 (3H, s), 2.66-3.3 (2H, m), 3.66 (2H, t, J=6 Hz), 7.3-7.8 (5H, m), 7.9-8.6 (4H, m).
Mass (M/Z): 440 (M+).
(58) Methyl 6-methyl-4-(3-hydroxyphenyl)-2-phenyl-5-pyrimidinecarboxylate.
(59) Methyl 2-(4-chlorophenyl)-6-methyl-4-(3-nitrophenyl)-5-pyrimidinecarboxylate.
mp: 105°-107° C.
IR (Nujol): 1725, 1530, 1350 cm$^{-1}$.
NMR (CDCl$_3$, δ): 2.68 (3H, s), 3.8 (3H, s), 7.4, 8.47 (total 4H, ABq, J=9 Hz), 7.6-8.65 (4H, m).
Mass (M/Z): 383, 385 (M+).
(60) Ethyl 6-diethoxymethyl-4-(3-nitrophenyl)-2-phenyl-5-pyrimidinecarboxylate.
mp: 84°-86° C.
IR (Nujol): 1730, 1535, 1355 cm$^{-1}$.
NMR (DMSO-d$_6$, δ): 1.13 (3H, t, J=7 Hz), 1.23 (6H, t, J=7 Hz), 3.69 (2H, q, J=7 Hz), 3.74 (2H, q, J=7 Hz), 4.20 (2H, q, J=7 Hz), 5.70 (1H, s), 7.45-7.65 (3H, m), 7.84 (1H, dd, J=9 Hz, 9 Hz), 8.15 (1H, ddd, J=9 Hz, 2 Hz, 2 Hz), 8.3-8.6 (4H, m).
(61) 6-Methyl-5-(4-methylpiperazin-1-ylcarbonyl)-4-(2-nitrophenyl)-2-phenylpyrimidine.
mp: 114°-115° C.
IR (Nujol): 1620, 1545, 1525, 1360 cm$^{-1}$.
NMR (CDCl$_3$, δ): 1.4-2.0 (2H, m), 2.1 (3H, s), 2.1-2.5 (2H, m), 2.65 (3H, s), 3.25 (2H, t, J=6 Hz), 3.4-3.9 (2H, m), 7.3-7.5 (3H, m), 7.5-8.0 (4H, m), 8.2-8.4 (2H, m)
Mass (M/Z): 417 (M+).
(62) 6-Methyl-5-(4-methylpiperazin-1-ylcarbonyl)-4-(4-nitrophenyl)-2-phenylpyrimidine.
mp: 257°-258° C.
IR (Nujol): 1632, 1530, 1350, 1295, 1270 cm$^{-1}$.
NMR (CDCl$_3$, δ): 1.4-1.9 (2H, m), 2.0-2.4 (2H, m), 2.13 (3H, s), 2.65 (3H, s), 2.7-3.2 (2H, m), 3.7 (2H, q, J=5 Hz), 7.3-7.6 (3H, m), 8.03-8.33 (total 4H, ABq, J=9 Hz), 8.4-8.6 (2H, m).
Mass (M/Z): 417 (M+).
(63) Ethyl 2-(4-chlorophenyl)-4-(4-nitrophenyl)-5-pyrimidinecarboxylate.
mp: 184°-185° C.
IR (Nujol): 1734, 1600, 1582, 1535, 1360 cm$^{-1}$.
NMR (CDCl$_3$, δ): 1.22 (3H, t, J=8 Hz), 4.28 (2H, q, J=8 Hz), 7.43, 8.33 (4H, ABq, J=8 Hz), 7.75, 8.47 (4H, ABq, J=9 Hz), 9.24 (1H, s)
Mass (M/Z): 383, 385 (M+).
(64) Ethyl 4-(4-nitrophenyl)-2-(4-pyridyl)-5-pyrimidinecarboxylate.
mp: 164°-165° C.
IR (Nujol): 1718, 1600, 1578, 1558, 1352 cm$^{-1}$.
NMR (DMSO-d$_6$, δ): 1.16 (3H, t, J=7 Hz), 4.26 (2H, q, J=7 Hz), 7.95, 8.40 (totao 4H, ABq, J=9 Hz), 8.35 (2H, dd, J=2, 5 Hz), 8.82 (2H, dd, J=2, 5 Hz), 9.4 (1H, s).
Mass (M/Z): 350 (M+).
(65) 5-Acetyl-2,4-di-(4-pyridyl)pyrimidine.
mp: 172°-174° C.
IR (Nujol): 1690, 1600, 1573, 1560, 1545, 1515 cm$^{-1}$.
NMR (DMSO-d$_6$, δ): 2.56 (3H, s), 7.62 (2H, dd, J=2, 5 Hz), 8.28 (2H, dd, J=2, 5 Hz), 8.52-8.94 (4H, m), 9.33 (1H, s)
(66) Ethyl 2-(4-chlorophenyl)-4-(3-nitrophenyl)-5-pyrimidinecarboxylate.
mp: 179°-180° C.
IR (Nujol): 1720, 1525, 1360 cm$^{-1}$.
NMR (DMSO-d$_6$, δ): 1.13 (3H, t, J=6 Hz), 4.22 (2H, q, J=6 Hz), 7.56, 8.45 (total 4H, ABq, J=9 Hz), 7.6-8.4 (4H, m), 9.27 (1H, s)
Mass (M/Z): 383, 385 (M+).

EXAMPLE 48

A mixture of 4-(4-hydroxy-3-nitrophenyl)-6-methyl-5-(4-methylpiperazin-1-ylcarbonyl)-2-phenylpyrimidine (0.8 g) and 10% Palladium on carbon (0.2 g) in methanol (30 ml) was hydrogenated at room temperature under atmospheric pressure. After removal of the catalyst by filtration, the filtrate was evaporated under reduced pressure. The residue was subjected to column chromatography on silica gel (100 g) and eluted with a mixture of chloroform and methanol (30:1). The fractions containing the object compound were combined and concentrated under reduced pressure. The residue was recrystallized from diethyl ether to give 4-(3-amino-4-hydroxyphenyl)-6-methyl-5-(4-methylpiperazin-1-ylcarbonyl)-2-phenylpyrimidine (0.2 g).
mp: 129°-131° C.
IR (Nujol): 1633, 1293 cm$^{-1}$.
NMR (DMSO-d$_6$, δ): 1.3-1.7 (1H, m), 2.03 (3H, s), 2.47 (3H, s), 1.8-3.8 (10H, m), 6.73 (1H, d, J=9 Hz), 6.93 (1H, dd, J=9 Hz, 2 Hz), 7.21 (1H, d, J=2 Hz), 7.3-7.6 (3H, m), 8.3-8.55 (2H, m).
Mass (M/Z): 403 (M+).

EXAMPLE 49

The following compound was prepared according to the similar manner to that of Example 48.
(1) 4-(3-Aminophenyl)-6-methyl-5-(4-methylpiperazin-1-ylcarbonyl)-2-phenylpyrimidine.
IR (Nujol): 1632, 1605, 1535 cm$^{-1}$.
NMR (DMSO-d$_6$, δ): 2.5 (3H, s), 2.55 (3H, s), 2.6-4.0 (10H, m), 6.6-7.65 (7H, m), 8.3-8.6 (2H, m)

Mass (M/Z): 387 (M+).

EXAMPLE 50

A mixture of 6-methyl-4-(3-nitrophenyl)-2-phenyl-5-pyrimidinecarboxamide (5 g), formalin (37%, 1.35 ml), N-methylpiperazine (2.25 g), ethanol (50 ml) and 1,2-dichloroethane (25 ml) was refluxed for 6 hours. After evaporating the solvent in vacuo, the residue was chromatographed on alumina (200 ml) and eluted with chloroform. The fractions containing the object compound were combined and concentrated under reduced pressure. The residue was recrystallized from diethyl ether to give 6-methyl-N-(4-methylpiperazin-1-ylmethyl)-4-(3-nitrophenyl)-2-phenyl-5-pyrimidinecarboxamide (1.90 g).

mp: 129°–131° C.
IR (Nujol): 3275, 1633 cm$^{-1}$.
NMR (CDCl$_3$, δ): 2.19 (3H, s), 2.1–2.55 (8H, m), 2.67 (3H, s), 4.08 (2H, d, J=6 Hz), 6.25 (1H, t, J=6 Hz), 7.3–7.55 (3H, m), 7.56 (1H, dd, J=9 Hz, 9 Hz), 8.0–8.55 (4H, m), 8.67 (1H, dd, J=2 Hz, 2 Hz).
Mass (M/Z): 446 (M+).

EXAMPLE 51

The following compounds were prepared according to the similar manner to that of Example 50.

(1) 6-Methyl-4-(3-nitrophenyl)-2-phenyl-N-(thiomorpholinomethyl)-5-pyrimidinecarboxamide.
mp: 184°–186° C.
IR (Nujol): 3210, 1633 cm$^{-1}$.
NMR (CDCl$_3$, δ): 2.49 (8H, s), 2.67 (3H, s), 4.12 (2H, d, J=6 Hz), 6.21 (1H, t, J=6 Hz), 7.3–7.8 (4H, m), 8.0–8.8 (5H, m)
Mass (M/Z): 449 (M+).

(2) N-(Dimethylaminomethyl)-6-methyl-4-(3-nitrophenyl)-2-phenyl-5-pyrimidinecarboxamide.
mp: 128°–130° C.
IR (Nujol): 3250, 1640 cm$^{-1}$.
NMR (CDCl$_3$, δ): 2.10 (6H, s), 2.67 (3H, s), 4.02 (2H, d, J=6 Hz), 6.37 (1H, t, J=6 Hz), 7.3–7.7 (4H, s), 8.05–8.8 (5H, m)
Mass (M/Z): 391 (M+).

EXAMPLE 52

To a mixture of methyl 6-methyl-4-(3-hydroxyphenyl)-2-phenyl-5-pyrimidinecarboxylate (8 g), 1,4-dioxane (200 ml) and ethanol (40 ml), a gas of chlorodifluoromethane was bubbled for 30 minutes at 5° C. To the mixture was dropwise added 4N sodium hydroxide (37 ml) for 5 minutes. The reaction mixture was stirred for 3 hours at ambient temperature and evaporated in vacuo. The residue was subjected to a column chromatography on silica gel and eluted with a 2:5 mixture of ethyl acetate and n-hexane. The fractions containing the desired product were combined and concentrated in vacuo. The residue was recrystallized from n-hexane to afford methyl 4-[3-(difluoromethoxy)phenyl]-6-methyl-2-phenyl-5-pyrimidinecarboxylate (2.3 g).

mp: 62°–63° C.
IR (Nujol): 1725, 1545 cm$^{-1}$.
NMR (CDCl$_3$, δ): 2.67 (3H, s), 3.77 (3H, s), 6.56 (1H, t, J=72 Hz), 7.2–7.8 (7H, m), 8.4–8.7 (2H, m)
Mass (M/Z): 370 (M+).

EXAMPLE 53

The following compounds are prepared according to the similar manner to that of Example 52.

(1) Ethyl 4-[2-(4-chlorobenzyloxy)phenyl]-6-methyl-2-phenyl-5-pyrimidinecarboxylate.
mp: 112°–113° C.

(2) Ethyl 4-[2-(4-chlorobenzyloxy)-5-nitrophenyl]-2-phenyl-6-methyl-5-pyrimidinecarboxylate.
mp: 156°–158° C.

(3) Ethyl 4-[2-(4-chlorobenzyloxy)-3-nitrophenyl]-2-phenyl-6-methyl-5-pyrimidinecarboxylate.
mp: 104°–105° C.

(4) Ethyl-4-[2-(4-chlorobenzyloxy)phenyl]-2,6-dimethyl-5-pyrimidinecarboxylate.
mp: 103°–105° C.

(5) Ethyl 4-(3-methoxyphenyl)-6-methyl-2-phenyl-5-pyrimidinecarboxylate.
mp: 53°–55° C.

EXAMPLE 54

A mixture of 5-acetyl-6-methyl-4-(3-nitrophenyl)-2-phenylpyrimidine (1.5 g), tetrahydrofuran (70 ml), sodium hypobromite (70 ml) was stirred for 2 hours at ambient temperature. To the mixture was added an aqueous sodium bisulfite solution. The mixture was washed with diethyl ether (100 ml) and the aqueous solution was acidified to pH 3.0 with 10% hydrochloric acid. The resultant crystals were collected by filtration to give 0.80 g of 6-methyl-4-(3-nitrophenyl)-2-phenyl-5-pyrimidinecarboxylic acid.

mp: 208°–209° C.
IR (Nujol): 1715, 1530, 1360 cm$^{-1}$.

What is claimed is:

1. Pyrimidine derivatives of the formula:

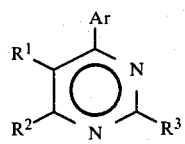

wherein

Ar is aryl substituted with 1 to 3 substituent(s) selected from the group consisting of nitro, amino, cyano, carbamoyl, halo(lower)alkyl, lower alkoxy, halo(lower)alkoxy, lower alkanoyloxy, lower alkylthio, lower alkanesulfinyl, lower alkanesulfonyl, esterified carboxy, N-containing heterocyclic group which may have 1 to 3 substituent(s) selected from the group consisting of lower alkyl, hydroxy(lower)alkyl and lower alkoxy, and a group of the formula:

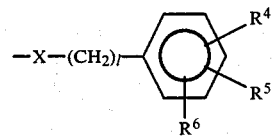

(in which X, l, R$^4$, R$^5$ and R$^6$ are each as defined in the below) or heterocyclic group containing one nitrogen and/or sulfur atom(s) and optionally substituted with nitro or halogen substituent(s);

R$^1$ is carboxy, esterified carboxy, lower alkanoyl, cyano, amino, carboxyamino, esterified carboxyamino, a group of the formula:

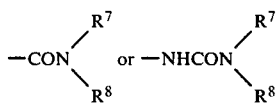

(in which $R^7$ and $R^8$ are each as defined in the below) or lower alkyl optionally substituted with 1 to 3 substituent(s) selected from the group consisting of hydroxy, halogen, cyano, carboxy, esterified carboxy and a group of the formula:

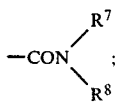

(in which $R^7$ and $R^8$ are each as defined in the below)

$R^2$ is hydrogen, aryl or lower alkyl optionally substituted with halogen, lower alkanoyloxy or lower alkoxy substituent(s); or $R^1$ and $R^2$ are taken together to form a lactone ring with the adjacent carbon atoms;

$R^3$ is lower alkyl, aryl optionally substituted with halogen or N-containing heterocyclic group which may have 1 to 3 substituent(s) selected from the group consisting of lower alkyl, hydroxy(lower)alkyl and lower alkoxy;

X is O or S;

l is an integer of 0, 1 to 6;

$R^4$, $R^5$ and $R^6$ are each hydrogen, nitro, lower alkyl, halogen or lower alkoxy;

$R^7$ and $R^8$ are each hydrogen, N-containing heterocyclic group which may have 1 to 3 substituent(s) selected from the group consisting of lower alkyl, hydroxy(lower)alkyl and lower alkoxy or lower alkyl optionally substituted with 1 to 3 substituent(s) selected from the group consisting of hydroxy, halogen, amino, lower alkanoylamino, mono- or di-(lower)alkylamino, tri(lower)alkylammonio and N-containing heterocyclic group which may have 1 to 3 substituent(s) selected from the group consisting of lower alkyl, hydroxy(lower)alkyl and lower alkoxy; or $R^7$ and $R^8$ are taken together to form N-containing heterocyclic group with the adjacent nitrogen atom, which may have 1 to 3 substituent(s) selected from the group consisting of lower alkyl, lower alkoxy, ar(lower)alkyl and lower alkoxy substituted ar(lower)alkyl; provided that the substituent(s) on the aryl group for Ar is not halogen when $R^2$ is hydrogen, and its pharmaceutically acceptable salts.

2. A compound as claimed in claim 1, wherein Ar is aryl substituted with nitro.

3. A compound as claimed in claim 2, wherein $R^2$ is lower alkyl.

4. A compound as claimed in claim 3, wherein $R^3$ is aryl.

5. A compound as claimed in claim 4, wherein $R^1$ is a group of the formula:

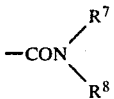

6. A compound as claimed in claim 5, wherein $R^7$ and $R^8$ are taken together to form 6-membered saturated N-containing heteromonocyclic group with the adjacent nitrogen atom, which may have 1 to 3 substituent(s) selected from the group consisting of lower alkyl, lower alkoxy, ar(lower)alkyl and lower alkoxy substituted ar(lower)alkyl.

7. A compound as claimed in claim 6, which is 6-methyl-5-(4-methylpiperazin-1-ylcarbonyl)-4-(3-nitrophenyl)-2-phenylpyrimidine.

8. A compound as claimed in claim 5, wherein, $R^7$ and $R^8$ are each hydrogen or lower alkyl substituted with 1 to 3 substituent(s) selected from the group consisting of mono- or di-(lower)alkylamino and saturated 6-membered N-containing heteromonocyclic group.

9. A compound as claimed in claim 8, wherein $R^7$ is hydrogen and $R^8$ is lower alkyl substituted with saturated 6-membered N-containing heteromonocyclic group.

10. A compound as claimed in claim 9, which is 6-methyl-4-(3-nitrophenyl)-2-phenyl-N-[2-(4-thiomorpholino)ethyl]-5-pyrimidinecarboxamide.

11. A compound as claimed in claim 8, wherein $R^7$ is hydrogen and $R^8$ is lower alkyl substituted with mono- or di-(lower)alkylamino.

12. A compound as claimed in claim 11, which is N-(2-dimethylaminoethyl)-6-methyl-4-(3-nitrophenyl)-2-phenyl-5-pyrimidinecarboxamide and its fumarate.

13. A compound as claimed in claim 4, wherein $R^1$ is a group of the formula:

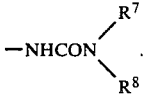

14. A pharmaceutical composition for treating cerebrovascular disease comprising, as an active ingredient, an effective amount of the compound of claim 1, in association with a non-toxic, pharmaceutically acceptable carrier or excipient.

15. A method for treating cerebrovascular disease which comprises administering to a subject in need of treatment an effective amount of a pyrimidine derivative of the formula:

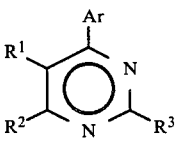

wherein

Ar is aryl substituted with 1 to 3 substituent(s) selected from the group consisting of nitro, amino, halogen, cyano, hydroxy, carbamoyl, halo(lower)alkyl, lower alkoxy, halo(lower)alkoxy, lower alkanoyloxy, lower alkylthio, lower alkanesulfinyl, lower alkanesulfonyl, esterified carboxy, N-containing heterocyclic group which may have 1 to 3 substituent(s) selected from the group consisting of lower alkyl, hydroxy(lower)alkyl and lower alkoxy, and a group of the formula:

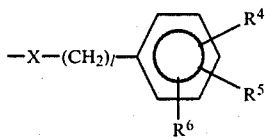

in which
X, l, $R^4$, $R^5$ and $R^6$ are each as defined in the below, or heterocyclic group containing one nitrogen and/or sulfur atom(s) and optionally substituted with nitro or halogen substituent(s);

$R^1$ is carboxy, esterified carboxy, lower alkanoyl, cyano, amino, carboxyamino, esterified carboxyamino, a group of the formula:

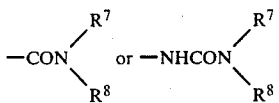

in which
$R^7$ and $R^8$ are each as defined in the below, or lower alkyl optionally substituted with 1 to 3 substituent(s) selected from the group consisting of hydroxy, halogen, cyano, carboxy, esterified carboxy and a group of the formula:

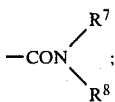

in which
$R^7$ and $R^8$ are each as defined in the below,
$R^2$ is hydrogen, aryl or lower alkyl optionally substituted with halogen, lower alkanoyloxy or lower alkoxy substituent(s); or
$R^1$ and $R^2$ are taken together to form a lactone ring with the adjacent carbon atoms;
$R^3$ is lower alkyl, aryl optionally substituted with halogen or N-containing heterocyclic group which may have 1 to 3 substituent(s) selected from the group consisting of lower alkyl, hydroxy(lower)alkyl and lower alkoxy;
X is O or S;
l is an integer of 0, 1 to 6;
$R^4$, $R^5$ and $R^6$ are each hydrogen, nitro, lower alkyl, halogen or lower alkoxy;
$R^7$ and $R^8$ are each hydrogen, N-containing heterocyclic group which may have 1 to 3 substituent(s) selected from the group consisting of lower alkyl, hydroxy(lower)alkyl and lower alkoxy or lower alkyl optionally substituted with 1 to 3 substituent(s) selected from the group consisting of hydroxy, halogen, amino, lower alkanoylamino, mono- or di-(lower)alkylamino, tri(lower)alkylammonio and N-containing heterocyclic group which may have 1 to 3 substituent(s) selected from the group consisting of lower alkyl, hydroxy(lower)alkyl and lower alkoxy; or
$R^7$ and $R^8$ are taken together to form N-containing heterocyclic group with the adjacent nitrogen atom, which may have 1 to 3 substituent(s) selected from the group consisting of lower alkyl, lower alkoxy, ar(lower)alkyl and lower alkoxy substituted ar(lower)alkyl; provided that the substituent(s) on the aryl group for Ar is not halogen when $R^2$ is hydrogen, and its pharmaceutically acceptable salts.

* * * * *